United States Patent [19]

Dhanoa et al.

[11] Patent Number: 5,254,682

[45] Date of Patent: Oct. 19, 1993

[54] CYCLIC RENIN INHIBITORS CONTAINING 3(S)-AMINO-4-CYCLOHEXYL-2(R)-HYDROXY-BUTANOIC ACID OR 4-CYCLO-HEXYL-(2R, 3S)-DIHYDROXYBUTANOIC ACID OR RELATED ANALOGS

[75] Inventors: Daljit S. Dhanoa, Tinton Falls; Arthur A. Patchett, Westfield; William J. Greenlee, Teaneck; William H. Parsons, Rahway; Thomas A. Halgren, Upper Montclair; Ann E. Weber, Scotch Plains; Lihu Yang, Woodbridge, all of N.J.

[73] Assignee: Merck & Co., Inc., Rahway, N.J.

[21] Appl. No.: 714,114

[22] Filed: Jun. 11, 1991

Related U.S. Application Data

[63] Continuation-in-part of Ser. No. 618,599, Nov. 30, 1990, abandoned, which is a continuation-in-part of Ser. No. 558,982, Jul. 27, 1990, abandoned, which is a continuation-in-part of Ser. No. 447,957, Dec. 8, 1989, abandoned.

[51] Int. Cl.$^5$ ............................................. C07D 225/00
[52] U.S. Cl. .................................. 540/451; 540/454; 540/460; 540/463
[58] Field of Search ............... 540/451, 454, 460, 463

[56] References Cited

U.S. PATENT DOCUMENTS

| | | | |
|---|---|---|---|
| 4,477,440 | 10/1984 | Boger et al. | 424/177 |
| 4,477,441 | 10/1984 | Boger et al. | 424/177 |
| 4,665,052 | 5/1987 | Boger et al. | 514/11 |
| 4,743,584 | 5/1988 | Boger et al. | 514/11 |
| 4,782,043 | 11/1988 | Boger et al. | 514/11 |
| 4,921,855 | 5/1990 | Hemmi et al. | 514/235.8 |

FOREIGN PATENT DOCUMENTS

| | | |
|---|---|---|
| 156318 | 10/1985 | European Pat. Off. |
| 283055 | 9/1988 | European Pat. Off. |
| 365992 | 5/1990 | European Pat. Off. |

OTHER PUBLICATIONS

Sham et al., *Renin Inhibitors. Design and Synthesis of a New Class of Conformationally Restricted Analogues of Angiotensinogen*, J. Med. Chem., 31, 284–295 (1988).

Burger, *Hypotensive Drugs*, Medicinal Chemistry pp. 565–581, 600–601 (1960).

Haber, et al., *Renin Inhibitors: A Search for Principles of Design*, Journal of Cardiovascular Pharmacology 10 (suppl. 7) 857–858 (1987).

Plattner et al., *Renin Hibitors*, J. Med. Chem. 31, pp. 2277–2288 (1988).

Denkewalter et al., Progress In Drug Research, 10, pp. 510–512 (1966).

Bolis et al., Renin Inhibitors, J. Med. Chem., 30, pp. 1729–1737 (1987).

"Feslk et al., *Structural Refinement of a Cyclic Peptide.*," Biochemistry 26, pp. 1851–1859 (1987).

*Primary Examiner*—Mukund J. Shah
*Assistant Examiner*—Y. N. Gupta
*Attorney, Agent, or Firm*—Mark R. Daniel; Joseph F. DiPrima

[57] ABSTRACT

Compounds of the formula:

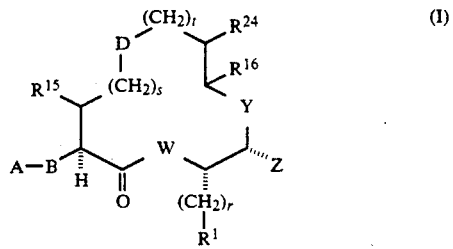

are disclosed. These compounds inhibit the angiotensinogen-cleaving action of the natural proteolytic enzyme, renin, and are useful in treating, preventing or managing renin-associated hypertension, hyperaldosteronism, congestive heart failure, and glaucoma.

15 Claims, No Drawings

CYCLIC RENIN INHIBITORS CONTAINING 3(S)-AMINO-4-CYCLOHEXYL-2(R)-HYDROXY-BUTANOIC ACID OR 4-CYCLO-HEXYL-(2R, 3S)-DIHYDROXYBUTANOIC ACID OR RELATED ANALOGS

CROSS-REFERENCE

This is a continuation-in-part application of U.S. Ser. No. 618,599 filed on Nov. 30, 1990 which is a continuation-in-part application of U.S. Ser. No. 558,982 filed on Jul. 27, 1990, which is a continuation-in-part application of U.S. Ser. No. 447,957 filed on Dec. 8, 1989 all now abandoned.

BACKGROUND OF THE INVENTION

1) Field of the Invention

The present invention is concerned with novel compounds I which inhibit the angiotensinogen-cleaving action of the natural proteolytic enzyme, renin, with pharmaceutical compositions containing the novel peptides of the present invention as active ingredients, with methods of treating, preventing or managing renin-associated hypertension, hyperaldosteronism, congestive heart failure and glaucoma with diagnostic methods which utilize the novel compounds I of the present invention, as well as processes therefor.

Renin is an endopeptidase (molecular weight about 40,000) produced and secreted by the juxtaglomerular cells of the kidney, which cleaves the naturally-occurring plasma glycoprotein, antiotensinogen, specifically at the 10, 11 peptide bond, i.e., between Leu 10 and Leu 11 in the equine substrate, as described by Skeggs et al, *J. Exper. Med.* 1957, 106, 439, or between the Leu 10 and Val 11 in the human renin substrate, as elucidated by Tewksbury et al., *Circulation* 59, 60, Supp. II: 132, October 1979. Renin cleaves angiotensinogen, its protein substrate, to split off the hemodynamically-inactive decapeptide, angiotensin I, which is converted in the lungs, kidney or other tissue by angiotensin-converting enzyme to the potent pressor octapeptide, angiotensin II. Angiotensin II is then believed to cause constriction of the arterioles and to stimulate release of the sodium-retaining hormone, aldosterone, from the adrenal gland and thereby cause a rise in extracellular fluid volume. Thus, the renin-angiotensin system plays an important role in normal cardiovascular homeostasis and in some forms of elevated blood pressure (hypertension).

Inhibitors of angiotensin I converting enzyme have proven useful in the modulation of the renin-angiotensin system. Consequently, specific inhibitors of the limiting enzymatic step that ultimately regulates angiotensin II production, the action of renin on its substrate, have also been sought as effective investigative tools, as well as therapeutic agents in the treatment of hypertension, congestive heart failure, and glaucoma.

Several cyclic renin inhibitor designs have been reported in the literature. In general, the aim of the studies reported was to use the conformational constraints imposed by the cyclic structures to help define the conformation of substrates and inhibitors as they bind to renin. None of these publications set forth possible advantages for inhibitors of this type or claim or establish any advantage for these cyclic inhibitors over their acyclic counterparts.

Early cyclic inhibitor designs used 18-membered or 20-membered rings to enclose a Pro-Phe beta-turn postulated to occur in bound substrate, and yielded inhibitors with moderate potency, comparable to that of acyclic analogs (C. L. Nakaie, M. C. F. Oliveira, L. Juliano, J. L. Pesquero and A. C. M. Paiva in Peptides, Structure and Function. Proceedings of the Eighth American Peptide Symposium, V. J. Hruby, and D. H. Rich, Eds., Pierce Chemical Co., Rockford, Ill., 1983, p. 595; C. R. Nakaie, J. L. Pesquero, M. C. F. Oliveira, L. Juliano and A. C. M. Paiva, in Peptides, Structure and Function. Proceedings of the Ninth American Peptide Symposium, C. M. Dever, V. J. Hruby and K. D. Kopple, Eds., Pierce Chemical Co., Rockford, Ill., 1985, p. 755).

Pairs of cysteine side-chains ($P_2$-$P_2'$ and $P_4$-$P_2'$ pairs) have been linked in high molecular weight cyclic inhibitor structures which are based on the $P_1$-$P_1'$ Phe-Phe sequence, statine, or a reduced peptide isostere. Only the cyclic inhibitors with a Phe-Phe sequence replacing the scissile bond of substrate show potency comparable to acyclic analogs (T. K. Sawyer, D. T. Pals, C. W. Smith, H. S. Saneii, D. E. Epps, D. J. Duchamp, J. B. Hester, R. E. TenBrink, D. J. Staples, A. E. deVaux, J. A. Affholter, G. F. Skala, W. M. Kati, J. A. Lawson, M. R. Schuette, B. V. Kamdar and D. E. Emmert in Peptides, Structure and Function. Proceedings of the Ninth American Peptide Symposium, C. M. Deber, V. J. Hruby and K. D. Kopple, Eds., Pierce Chemical Co., Rockford, Ill., 1985, p. 729).

Two cyclic inhibitor designs investigated by Boger et al., incorporated disulfides constructed from $P_2$ toward the carboxy terminus, and these had potency comparable to that of an acyclic analog. An amino-terminal cyclic disulfide inhibitor made by connecting $P_5$ and $P_2$ homocysteine sidechains encloses a Pro-Phe beta-turn. The optimal ring size for a $P_5$-$P_2$ cycle is found in the 16-membered ring inhibitor, and three other disulfide cycles with cysteine at either $P_5$ or $P_2$ (or both), were substantially less potent (J. Boger in Aspartic Proteinases and Their Inhibitors, V. Kostka, Ed., Walter de Gruyter, Berlin, 1985, p. 401; J. Boger in Proceedings of the Third SCI-RSC Medicinal Chemistry Symposium; Special Publication No. 55 of the Royal Society of Chemistry, R. W. Lambert, Ed., Burlington House, London W1V OBN, 1986, p. 271). Please see also U.S. Pat. Nos. 4,477,440 and 4,477,441.

A series of renin inhibitors in which the $P_1$ side-chain of a "reduced peptide" inhibitor is cyclized onto the alpha-nitrogen atom of alanine at $P_2$ has been reported (H. Sham, G. Bolis, H. H. Stein, S. W. Fesik, P. A. Marcotte, J. J. Plattner, C. A. Rempel and J. Greer, J. Med. Chem., 31, 284 (1988), but these have only moderate potency.

Although in some of the cases cited above, the ring-size of the cyclic element of the renin inhibitors cited above is similar to those of the cyclic renin inhibitors disclosed herein, the inhibitors of the present case are structurally distinct, and unlike other cyclic renin inhibitors have low molecular weight, show high in vitro potency against human renin, and are orally active.

DETAILED DESCRIPTION OF THE INVENTION AND PREFERRED EMBODIMENTS

In accordance with the present invention, there are provided novel compounds of the formula I:

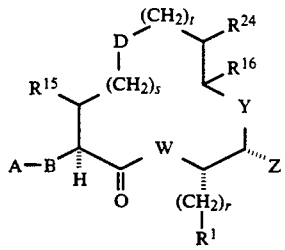

(I)

wherein:

A is hydrogen,

Het, where Het is a saturated or unsaturated 5 to 7-membered monocyclic or 7 to 10-membered bicyclic ring which contains at least one and up to two nitrogen atoms (optionally quaternized or in the N-oxide form), where Het may optionally be benzofused, where Het may optionally contain one additional ring atom chosen from among the list consisting of O or S, in sulfide, sulfoxide or sulfone form, where Het may optionally be substituted with one or two Het substituents independently selected from the group consisting of —OH, $C_1$-$C_4$-alkyl, —$CF_3$, —CN, $C_1$-$C_4$-alkoxy, $C_1$-$C_4$-alkoxy-$C_1$-$C_4$-alkoxy, halo, —$NH_2$, mono-or di-($C_1$-$C_4$-alkyl)amino, —$CO_2$H, —$CO_2$—$C_1$-$C_4$-alkyl, —$CONR^{2a}R^{2b}$, —$SO_3$H, $C_1$-$C_4$-alkyl-CO—, aryl (where aryl is unsubstituted or mono-, di-, or trisubstituted phenyl or naphthyl wherein the substitutent(s) is/are independently selected from the group consisting of $C_1$-$C_8$-alkyl, amino, phenyl-$C_1$-$C_4$-alkyl, mono- or di-$C_1$-$C_4$-alkyl amino, amino-$C_1$-$C_4$-alkyl, mono- or di-$C_1$-$C_4$-alkyl-amino-$C_1$-$C_4$-alkyl, guanidyl, guanidyl-$C_1$-$C_4$-alkyl, —OH, $C_1$-$C_4$-alkoxy, —$CONR^{2a}R^{2b}$, —$CO_2$H, —$CO_2$—$C_1$-$C_4$-alkyl, —$CF_3$, halo, $C_1$-$C_4$-alkyl-CO—, $C_1$-$C_4$-alkyl-CONH—, tri-($C_1$-$C_4$-alkyl)$N^+$ $X^-$, where $X^-$ is a counterion selected from the group consisting of single negatively charged ions, such as chloride, bromide, nitrate, perchlorate, benzoate, maleate, benzenesulfonate, methanesulfonate, tartrate, hemitartrate, and acetate) and mono- or disubstituted $C_1$-$C_4$-alkyl (where the substitutent(s) is/are independently selected from the group consisting of —$CO_2$H, —$CO_2$—$C_1$-$C_5$-alkyl, $C_1$-$C_5$-alkyl-CONH—, —OH, —$SO_3$H, $C_1$-$C_4$-alkyl-$SO_2$—, $C_1$-$C_4$-alkyl-SO—, —$SO_2$NHCO—$C_1$-$C_4$-alkyl, $C_1$-$C_5$-alkyl-OCONH— and aryl as defined above), where if one or both N are quaternized in Het, then each nitrogen atom may be quaternized with a Het substituent cited above selected from the group consisting of —$C_1$-$C_4$-alkyl, —$CF_3$, aryl and mono- or disubstituted $C_1$-$C_4$-alkyl with the corresponding counterion being $X^-$ as defined above, where Het may have in the alternative to the above Het substituents, a Het substituent selected from the group consisting of —$(CH_2)_q$— and —$(CH_2)_2O(CH_2)_2$— which forms a quaternary spirocyclic ring with the N atom wherein q is 3-to-6 and the counterion is $X^-$ as defined above, where Het may be substituted both with one Het substituent chosen from among those listed above and also with up to four Het substituents selected from the group consisting of $C_1$-$C_2$-alkyl substituents (for example where A is 3,3,5,5-tetramethyl-4-benzylpiperidin-4-yl), and Het-$C_1$-$C_4$-alkyl (where Het is as defined above without optional substitution and where the alkyl group is optionally substituted with one or two substituents independently selected from the group consisting of hydroxyl, —$CO_2$H, —$CO_2$—$C_1$-$C_4$-alkyl, —$SO_3$H, and aryl where aryl is as defined above), aryl, where aryl is defined above, $R^2$CO—, where $R^2$ is unsubstituted or mono- or disubstituted $C_1$-$C_4$-alkyl where the substituent(s) is/are selected from the group consisting of $C_1$-$C_4$-alkyl, —$SO_3$H, aryl or aryl-CO— (where aryl is as defined above), Het or Het-CO— (where Het is as defined above), $R^{2a}$O—, $R^{2a}$OCO—, $R^{2a}R^{2b}$N—, $R^{2a}R^{2b}$NCO—, $R^{2a}R^{2b}$NCONH—, $R^{2a}R^{2b}$N$SO_2$, ($R^{2a}$O)($R^{2b}$O)PO—, $R^{2c}$S—, $R^{2c}$SO—, $R^{2c}SO_2$—, $R^{2c}$CONH—, $R^{2c}$OCONH—, and —N($R^{17}R^{18}R^{19}$)+$X^-$ (where $R^{2a}$ and $R^{2b}$ are independently hydrogen, $C_1$-$C_4$-alkyl, aryl as defined above, Het as defined above, $R^{2c}$ is $C_1$-$C_4$-alkyl, aryl as defined above or Het as defined above, $R^{19}$ is $C_1$-$C_4$-alkyl, $R^{17}$ and $R^{18}$ are independently aryl as defined above, Het as defined above or $C_1$-$C_4$-alkyl optionally substituted with a substituent chosen from the group consisting of aryl as defined above, Het as defined above, —OH, —$NH_2$, —NH—$C_1$-$C_4$-alkyl, —N($C_1$-$C_4$-alkyl)$_2$, —$CO_2$H, —$CO_2$—$C_1$-$C_4$-alkyl, —$SO_3$H, —CO—NH—$SO_2$—$C_1$-$C_4$-alkyl, or —CO—NH—$SO_2$—aryl, and $X^-$ is as defined above), $R^2$— (where $R^2$ is as defined above), $R^2$OCO— (where $R^2$ is as defined above), $R^2SO_2$— (where $R^2$ is as defined above), Aryl-CO— (where aryl is as defined above), Het-CO— (where Het is as defined above), $R^{2a}R^{2b}$N—CO— (where $R^{2a}$ and $R^{2b}$ are as defined above),

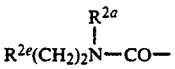

where $R^{2a}$ is as defined above and $R^{2e}$ is Het-CO where Het is as defined or Het $SO_2$—, $R^{2a}R^{2b}$N—$SO_2$— (where $R^{2a}$ and $R^{2b}$ are as defined above) and $C_1$-$C_4$-alkyl-($OCH_2CH_2$)$_x$OCO— (where x is 1 to 3);

B is

—$CH_2$—CH[$(CH_2)_r R^3$]CON($R^{11}$)—N-($A^1$)CH[$(CH_2)_r R^3$]CO—N($R^{11}$)—,

—O—CH[$(CH_2)_r R^3$]CO—N($R^{11}$)—, —N-($A^1$)CH[$(CH_2)_r R^3$]—CO—O—,

—O—CH[$(CH_2)_r R^3$]CO—O— or —N-($A^1$)CH[$(CH_2)_r R^3$]CH(OH)$CH_2$—, where r is 0-to-2, $A^1$ is hydrogen or $C_1$-$C_4$-alkyl, $R^3$ is hydrogen, $C_1$-$C_4$-alkyl, $C_3$-$C_7$-cycloalkyl, aryl as defined above, Het as defined above or 4-(morpholin-4-yl)ethoxy phenyl-, and $R^{11}$ is hydrogen or $C_1$-$C_4$-alkyl, A and B together may alternatively be:

G—$CH_2$CH[$(CH_2)_r R^3$]—Q—N($R^{11}$)—,

G—$CH_2$CH[$(CH_2)_r R^3$]—CO—O—, Het-S(O)$_m$—CH[$(CH_2)_r R^3$]CON($R^{11}$)—, (where r, $R^3$, $R^{11}$ and Het are as defined above and Q is —CO— or —SO₂—), $R^{2d}CON(R^{11})$—, $R^{2d}OCON(R^{11})$— or $R^{2d}SO_2N(R^{11})$—, $R^{2d}$—CO—O—, (where $R^{2d}$ is Het as defined above, aryl as defined above, or $C_1$-$C_4$-alkyl or $C_2$-$C_4$-alkenyl substituted with Het, Het-O—, aryl, or aryl-O—, each as defined above),

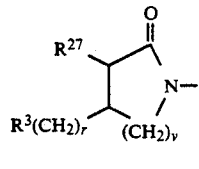

or

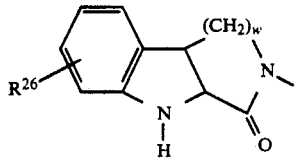

(where v is 1-to-3, w is 1 or 2, $R^3$ and r are as defined above, $R^{27}$ is hydrogen, $C_1$-$C_4$-alkyl or A—N(H)— where A is independently selected from the definitions of A as defined above and $R^{26}$ is $C_1$-$C_4$-alkyl, amino, mono- or di-$C_1$-$C_4$-alkylamino, —OH, $C_1$-$C_4$-alkoxy, —CO₂H, —CO₂—$C_1$-$C_4$-alkyl, —CONR$^{2a}$R$^{2b}$, —CF₃, halo, —NHCO—O—$C_1$-$C_4$-alkyl, —N($C_1$-$C_4$-alkyl)-CO—O—$C_1$-$C_4$-alkyl, —NHCO—$C_1$-$C_4$-alkyl or —N($C_1$-$C_4$-alkyl)CO—$C_1$-$C_4$-alkyl);

G is
$R^{20}$—S(O)$_m$— (where m is 0-to-2 and $R^{20}$ is $C_3$-$C_7$-cycloalkyl, aryl as defined above, Het as defined above or $C_1$-$C_6$-alkyl optionally substituted with one or two substituents chosen from the group consisting of $C_1$-$C_4$-alkoxy, —OH, —CO₂H, —CO₂—$C_1$-$C_4$-alkyl, —NH₂, —NH($C_1$-$C_4$-alkyl), —N($C_1$-$C_4$-alkyl)₂, and ($C_1$-$C_5$-alkyl)CO—O—), $R^{17}R^{18}NSO_2$— (where $R^{17}$ and $R^{18}$ are as defined above),

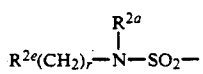

where r, $R^{2a}$ and $R^{2e}$ are as defined above, or

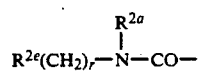

where r, $R^{2a}$ and $R^{2e}$ are as defined above; $R^{20}CO$— (where $R^{20}$ is as defined above), $R^{20}O$-CO— (where $R^{20}$ is as defined above) or —CH(OH)CH₂Het (where Het is defined above);
A and B together may be J—CH[(CH₂)$_r$—R³]—K—;
K is
 —CH₂—,
 —CH(OH)—,
 —CO—,
 —NH—,
 —O—,
 —S—,
 —SO—,
 —SO₂—,
 —NO—,
 —P(O)O—;

J is
 $R^{28}$—CO—(CH₂)$_d$ (where d is 0-to-4, $R^{28}$ is —OH, —O—$C_1$-$C_6$-alkyl, —NR$^{18}$R$^{18}$, Het), $R^{29}$—SO₂— (where $R^{29}$ is —$C_1$-$C_4$-alkyl, aryl, Het), $R^{30}$ (where $R^{30}$ is aryl, Het), —$C_1$-$C_4$-alkyl optionally substituted with aryl, Het, —CO₂H, —CO₂—$C_1$-$C_4$—, alkyl, —SO₂—$C_1$-$C_4$-alkyl, —SO₂Ar, —SO₂Het), $R^{30}$—NH—CO—, where $R^{30}$ is as defined above;

$R^1$ is
 $C_1$-$C_4$-alkyl, aryl as defined above, unsubstituted, di-, or trisubstituted $C_3$-$C_7$-cycloalkyl (where the substituents is/are selected from the group consisting of $C_1$-$C_4$-alkyl, trifluoromethyl, —OH, $C_1$-$C_4$-alkoxy, or halo) or a 5- or 6-membered ring saturated heterocycle containing one or two heteratoms selected from the group consisting of N, O or S, optionally substituted with one or two substituents (where the substituents is/are selected from among the group consisting of $C_1$-$C_4$-alkyl, $C_1$-$C_4$-alkoxy, halo, —NH₂, or —OH);

$R^{15}$ is
 $C_1$-$C_4$-alkyl, aryl as defined above, imidazol-4-yl, thiazol-4-yl or thiazol-5-yl;

D is
 a single bond or is
 —N(R²⁵)CO—
 —CO—N(R²⁵)—
 —NH—CO—NH—
 —NH—SO₂—NH—
 —SO₂—NH—
 —NH—SO₂—
 —CO—O—
 —O—CO—NH—
 —SO—
 —SO₂—
 —O—
 —S—
 —NH—CO—O—
 —CH=CH—
 —CO— or
 —CH(OH)—
 (where $R^{25}$ is —H or $C_1$-$C_4$-alkyl and asymmetrical groups are read clockwise into formula I from left to right);

s is 0-to-1;
t is 1-to-4;
W is N—$R^{23}$ or O (where $R^{23}$ is defined below);
$R^{16}$ is
 hydrogen or
 $C_1$-$C_4$-alkyl optionally substituted with a substituent chosen from among the group consisting of $C_1$-$C_4$-alkyl, $C_3$-$C_7$-cycloalkyl, aryl as defined above, Het as defined above, —OH, —SO₃H, —CO₂H, CO₂—$C_1$-$C_4$-alkyl, —CO—Het, —NR$^{17}$R$^{18}$, —NHR$^{18}$, —N(R$^{17}$R$^{18}$R$^{19}$)+X⁻ (where X⁻, $R^{17}$, $R^{18}$ and $R^{19}$ are defined above), —S(O)$_m$—R²¹ (where m is as defined above and $R^{21}$ is Het, aryl or $C_1$-$C_4$-alkyl the alkyl optionally substituted with a substituent chosen from among the group consisting of aryl, Het, —NH₂, —OH, —NH—$C_1$-$C_4$-alkyl or N($C_1$-$C_4$-alkyl)₂), —SO₂NH₂, —SO₂NR$^{17}$R$^{18}$ (where $R^{17}$ and $R^{18}$ are as defined above), —SO₂NHR$^{18}$ (where $R^{18}$ is as defined above) and —CH₂(OCH₂CH₂)$_x$—O—$C_1$-$C_4$-alkyl, (where x is as defined above);

Y is
—OCO—, —CH2CO— or —CH2CH(OH)— (where Y is inserted into formula I clockwise from left to right);

Z is
—NH2, —OH —OPO3H2, —OCOR22, —O—CO—OR22 (where R22 is 5-indanyl or C1-C6-alkyl optionally substituted with Ph, —SO3H, —CO2H, —PO3H2, —NH2, —NH(C1-C4-alkyl), —N(-C1-C4-alkyl)2, —N(C1-C4-alkyl)3+X− where X− is defined above), —OCHR22a—OCOR22b (where R22a and R22b are C1-C4-alkyl),

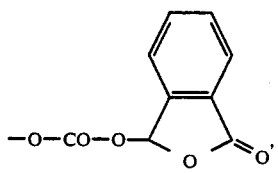

or —O—COCH2O—(CH2CH2O)x—C1-C4-alkyl
or —O—CO—O(CH2CH2O)x—C1-C4-alkyl
(where x is as defined above);

R23 is hydrogen or C1-C4-alkyl; and
R24 is hydrogen or C1-C4-alkyl.

Heterocyclic substituents in which nitrogen is the heteroatom are preferred, and of these, those containing a single nitrogen atom are preferred. Fully saturated heterocyclic substituents are also preferred. Thus, piperidine is a preferred heterocyclic substituent. Other preferred heterocyclic substituents are: pyrryl, pyrrolinyl, quinuclidinyl, isoquinuclidinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl and benzothienyl.

The term "halo" means fluoro, chloro, bromo and iodo.

Among the substituents for A, B, R1, R11, R15, R16, R23, R24, R25, Z and r preferred groups are recognized as follows. Preferred A are:

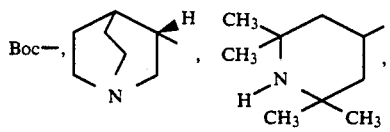

EtOC—, i-PrSO2—, CH3(OCH2CH2)3OCO—,

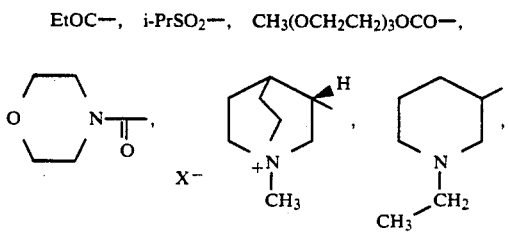

-continued

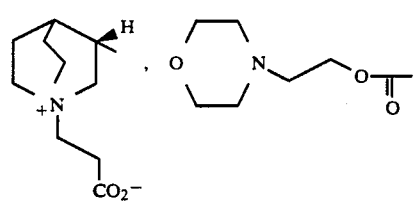

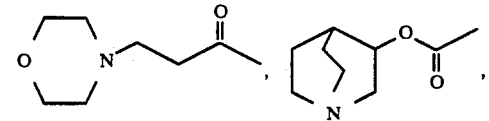

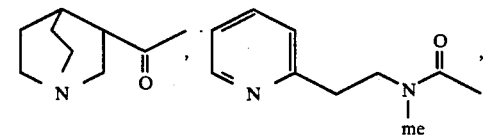

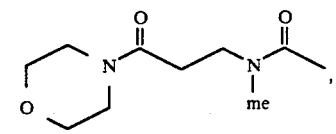

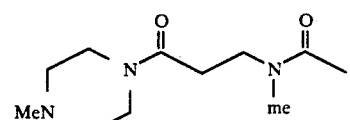

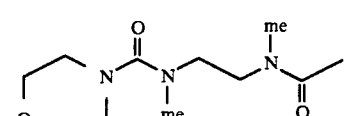

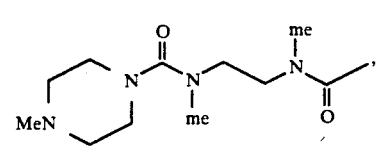

or

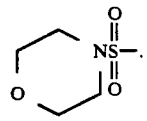

Preferred B are:

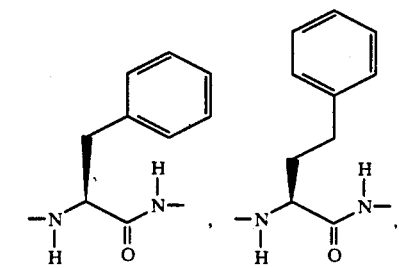

-continued
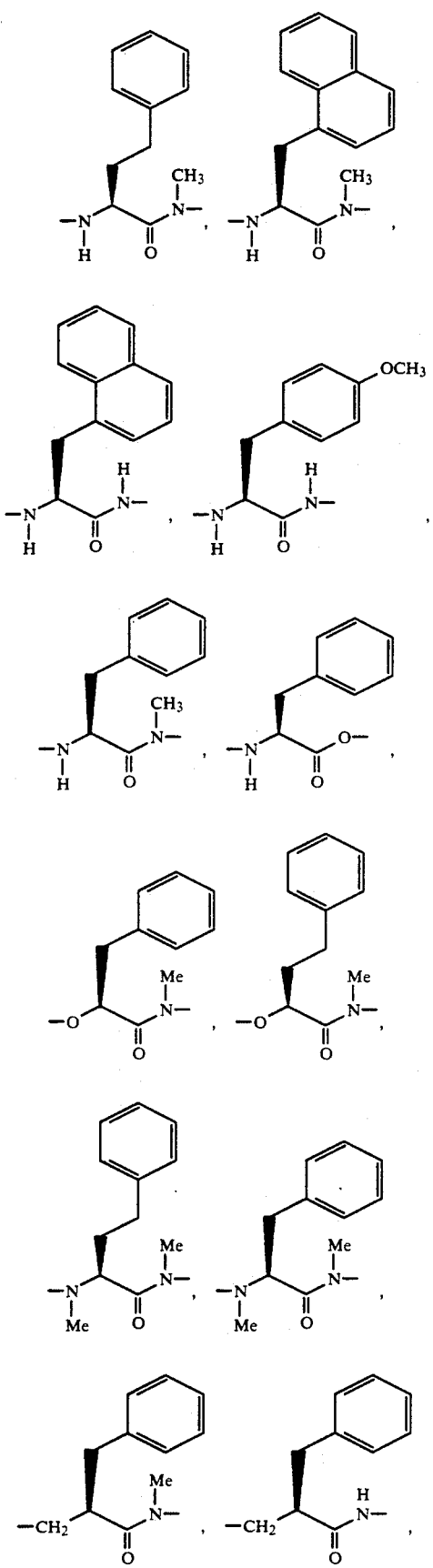
-continued
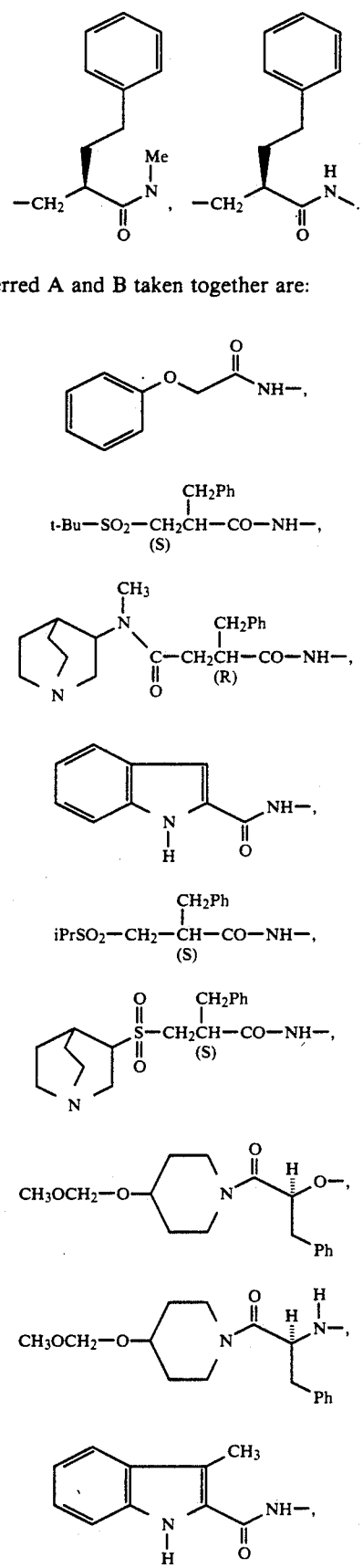
Preferred A and B taken together are:

-continued
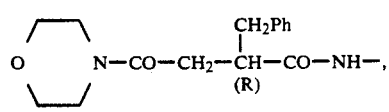
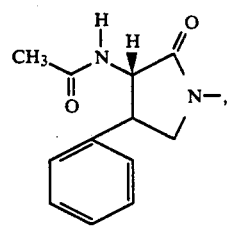
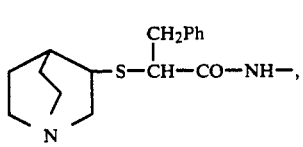
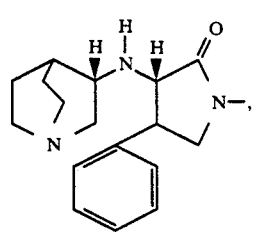
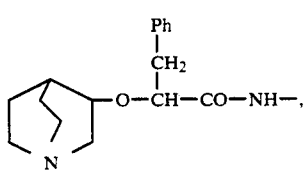
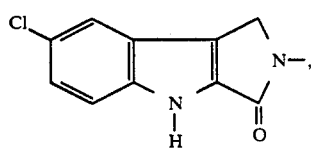
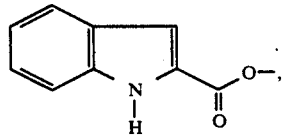
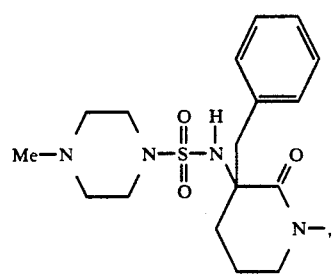
-continued
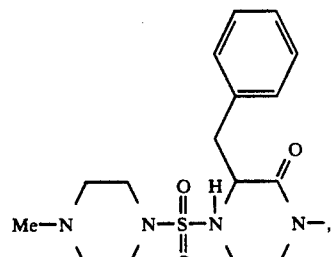
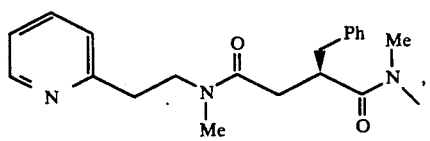
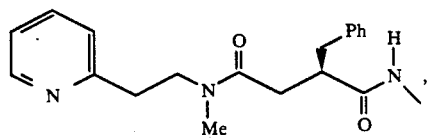
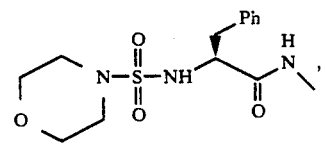
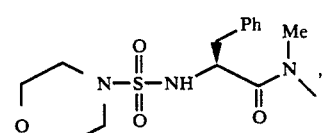
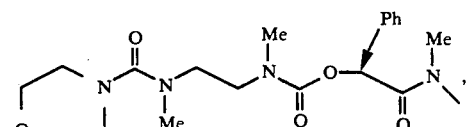
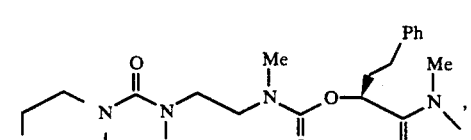
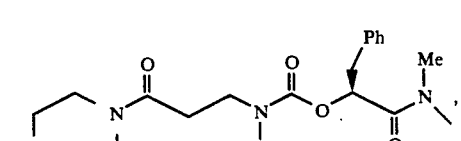
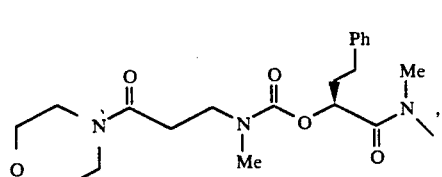

-continued

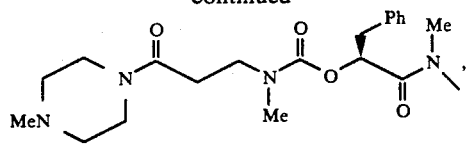

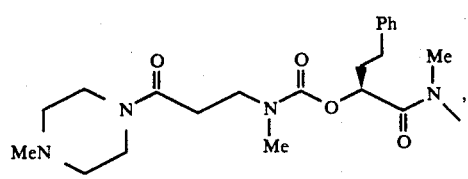

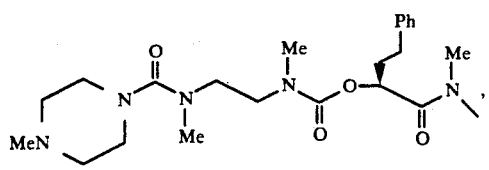

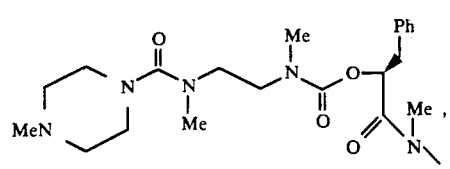

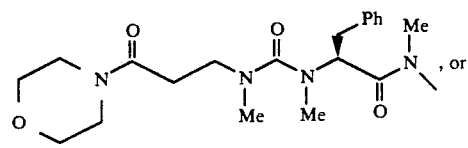, or

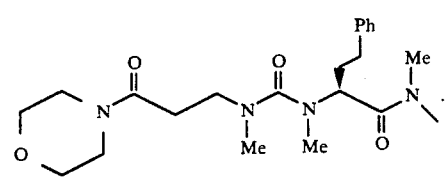

Preferred R$^{15}$ are —H, —CH$_3$, -i-Pr or -n-Pr.
Preferred R$^{16}$ are —H, n-butyl, -i-butyl, i-Pr,

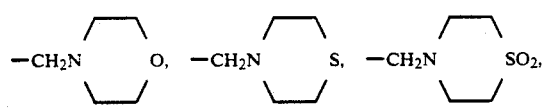

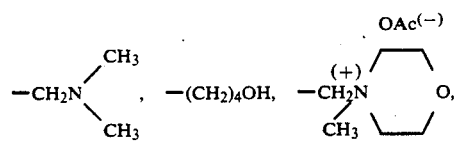

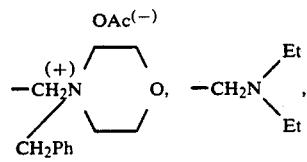

and 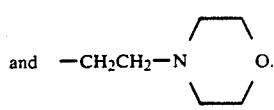

Preferred R$^{23}$ are —H or —CH$_3$;
R$^{24}$ are —H, —CH$_3$ or —Et;
R$^{25}$ are —H or —CH$_3$;
r is 1; and
Z are —OH, —OCO(CH$_2$)$_2$CO$_2$H, —OCOCH$_2$N(-C$_1$-C$_4$-alkyl)$_2$, —OCOCH$_2$NH$_2$, —O-COCH$_2$CH$_2$NH$_2$, —OCO(C$_1$-C$_4$-alkyl), —NH$_2$, —OCOCH(n-Bn)—NH$_2$, —OCOCH(i-Pr)NH$_2$, —O-PO$_3$H$_2$, —OCOCH$_2$CH$_2$PO$_3$H$_2$, and —O-CO—O(CH$_2$CH$_2$O)$_3$CH$_3$.

The preferred ring systems for the compounds of this invention include the following:

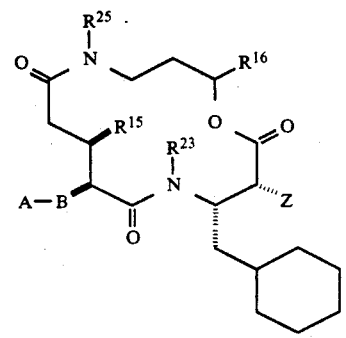

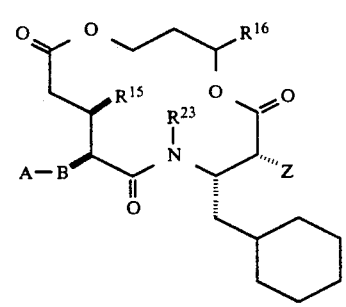

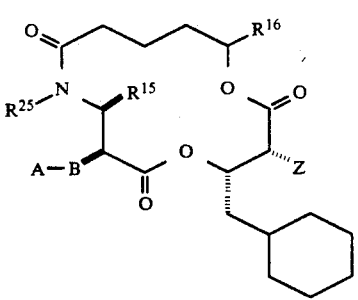

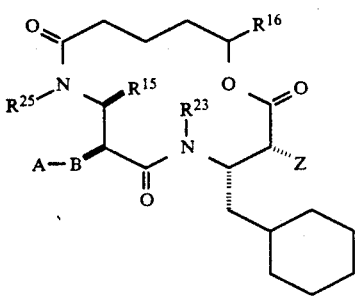

-continued
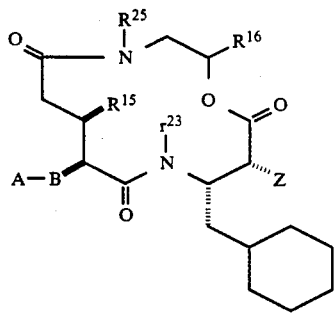
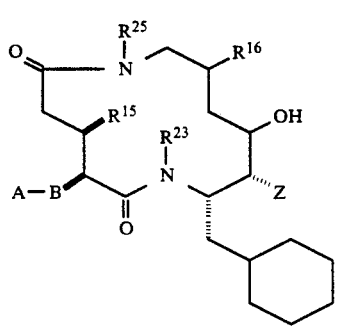
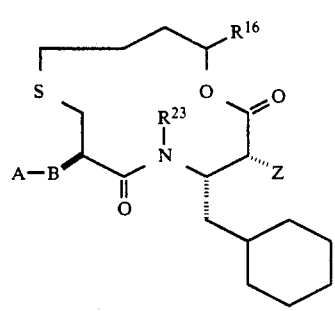
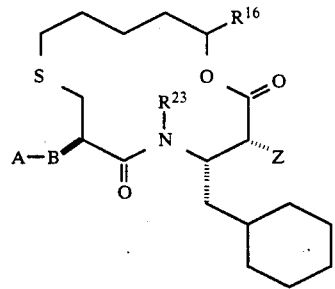
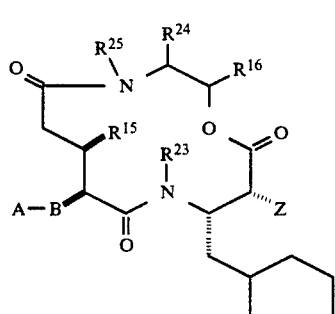
-continued
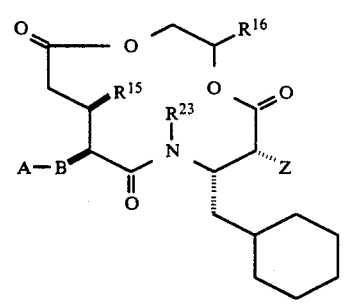
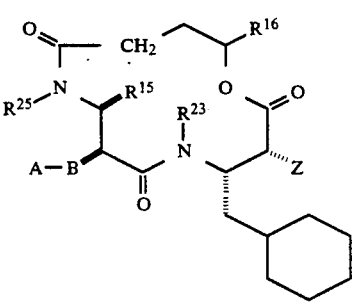
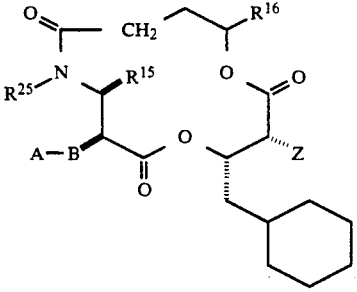
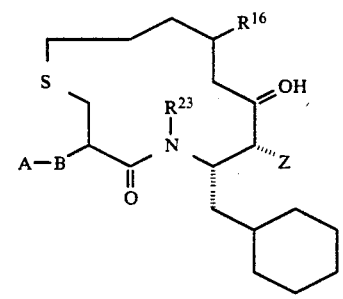
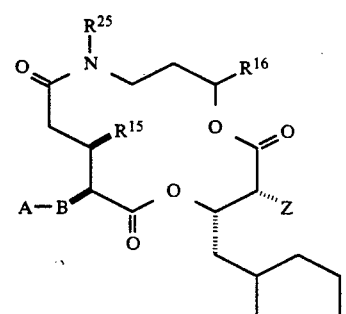

17
-continued

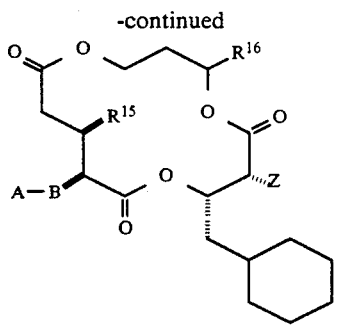

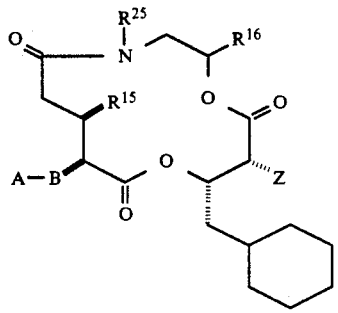

18
-continued

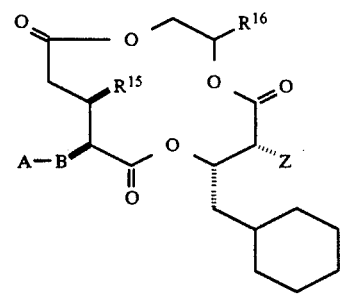

The preferred compounds of the present invention include the following: In cases where absolute configurations at the carbon atoms bearing substituents $R^{15}$, $R^{16}$ and $R^{24}$ are known, these are designated as "R" or "S". In cases where the absolute configuration has not been established, diastereomers are numbered (1 or 2). In these cases both diastereomers have activity against renin, but one diastereomer is more active than the other.

TABLE I

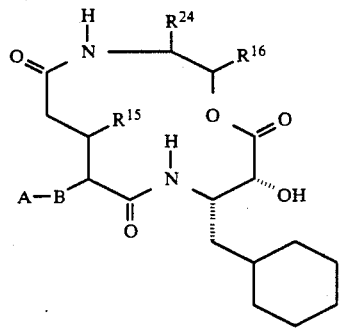

| A—B | $R^{24}$ (config) | $R^{15}$ (config) | $R^{16}$ (config) |
|---|---|---|---|
| BocPhe—NH— | Me(S) | H | H |
| tBuCH₂CONH(CH₂)₂COPhe—NH— | Me(S) | H | H |
| BocPhe—NH— | Me(R) | H | H |
| tBuCH₂CONH(CH₂)₂COPhe—NH— | Me(R) | H | H |
| BocPhe—NH— | Et(R) | H | H |
| tBuCH₂CONH(CH₂)₂COPhe—NH— | Et(R) | H | H |
| BocPhe—NH— | H | Me(1) | H |
| tBuCH₂CONH(CH₂)₂COPhe—NH— | H | Me(1) | H |
| tBuCH₂CONH(CH₂)₂COPhe—NH— | H | Me(2) | H |
| BocPhe—NH— | H | H | H |
| tBuCH₂CONH(CH₂)₂COPhe—NH— | H | H | H |
| (Z-piperidin-4-yl)-CH₂NHCOPhe—NH— | H | H | H |
| (piperidin-4-yl)CH₂NHCOPhe—NH— | H | H | H |
| Cbz—NH— | H | H | —CH₂N⟨morpholino⟩ O(1) |
| Cbz—NH— | H | H | —CH₂N⟨morpholino⟩ O(2) |

TABLE I-continued

[Structure shown: macrocyclic compound with substituents A—B, R15, R16, R24, OH, and cyclohexylmethyl group]

| A—B | R24 (config) | R15 (config) | R16 (config) |
|---|---|---|---|
| BocPhe—NH— | H | H | —CH$_2$N⟨morpholine⟩ O(1) |
| BocPhe—NH— | H | H | —CH$_2$N⟨morpholine⟩ O(2) |
| tBuCH$_2$CONH(CH$_2$)$_2$—COPhe—NH— | H | H | -n-Bu(1, 2) |
| BocPhe—NH— | H | H | -n-Bu(1) |
| BocPhe—NH— | H | H | -n-Bu(2) |
| [quinuclidinyl-NH-CH(CH$_2$Ph)-C(O)-NH-] | H | H | -n-Bu(1) |
| [quinuclidinyl-NH-CH(CH$_2$Ph)-C(O)-NH-] | H | H | -n-Bu(2) |
| [quinuclidinyl-NH-CH(CH$_2$NA)-C(O)-NH-] | H | H | -n-Bu(1) |
| BocPhe—NH— | H | H | n-Hex(1) |
| BocPhe—NH— | H | H | n-Hex(2) |
| BocPhe—NH— | H | H | n-Pent(1) |
| BocPhe—NH— | H | H | n-Pent(2) |
| BocPhe—NH— | H | H | —Et(1) |
| BocPhe—NH— | H | H | —Et(2) |
| Cbz—NH— | H | H | i-Bu(2) |
| BocPhe—NH— | H | H | i-Bu(1) |
| BocPhe—NH— | H | H | i-Bu(2) |
| [quinuclidinyl-NH-CH(CH$_2$Ph)-C(O)-NH-] | H | H | i-Bu(2) |
| BocPhe—NH— | H | H | 4-HO—Bu(1, 2) |
| BocPhe—NH— | H | H | neoPent(2) |

TABLE I-continued
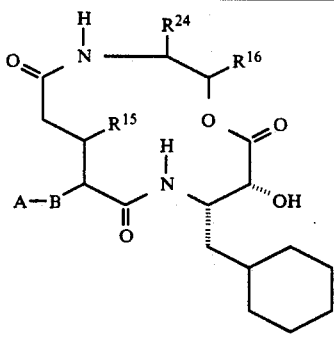
| A—B | R²⁴ (config) | R¹⁵ (config) | R¹⁶ (config) |
|---|---|---|---|
| 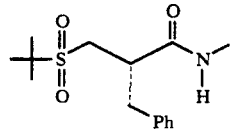 | H | H | 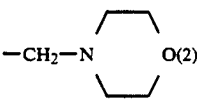 —CH₂—N⟨O(2)⟩ |
| 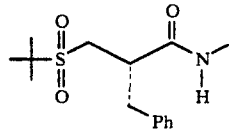 | H | H | 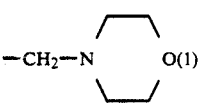 —CH₂—N⟨O(1)⟩ |
| 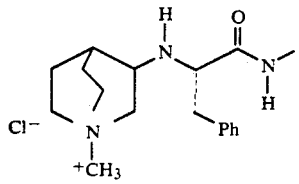 | H | H | 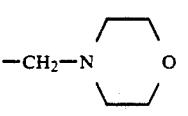 —CH₂—N⟨O⟩ |
| 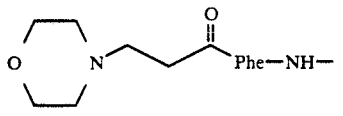 | H | H | 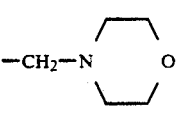 —CH₂—N⟨O⟩ |
| 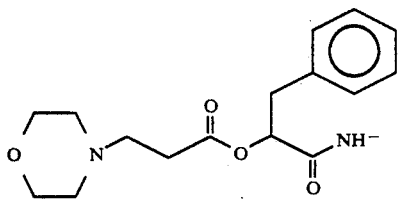 | H | H | 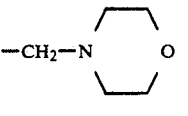 —CH₂—N⟨O⟩ |
| Boc—D—Pro—Phe—NH— | H | H | 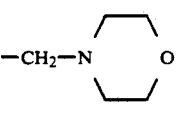 —CH₂—N⟨O⟩ |
| D—Pro—Phe—NH— | H | H | 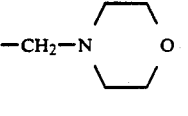 —CH₂—N⟨O⟩ |
| tBu—CH₂CONH(CH₂)₂CO—Phe—NH— | H | H | 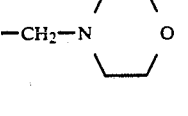 —CH₂—N⟨O⟩ |

TABLE I-continued
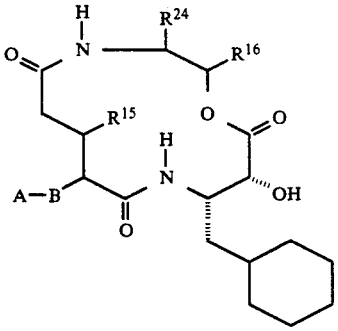
| A—B | $R^{24}$ (config) | $R^{15}$ (config) | $R^{16}$ (config) |
|---|---|---|---|
| Boc—NH—C(CH$_3$)$_2$CH$_2$CO—Phe—NH | H | H | 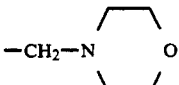 |
| NH$_2$—C(CH$_3$)$_2$CH$_2$CO—Phe—NH— | H | H | 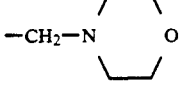 |
| 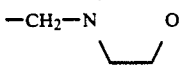 | H | H | 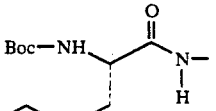 |
| 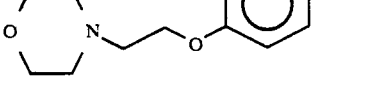 | —CH$_3$(R) | —H | 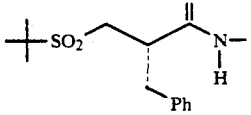 |
| " | —CH$_3$(R) | —H | 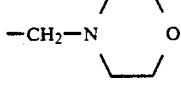 |
| " | —CH$_3$(S) | —H | 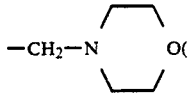 |
| " | —CH$_3$(S) | —H | 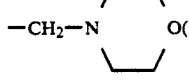 |
| " | —CH$_3$(R) | —H | -i-Bu(R) |
| " | —CH$_3$(R) | —H | -i-Bu(S) |
| " | —CH$_3$(S) | —H | -i-Bu(S) |
| " | —CH$_3$(S) | —H | -i-Bu(R) |
| 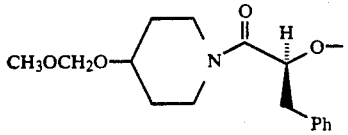 | —H | —H | 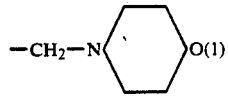 |

TABLE I-continued

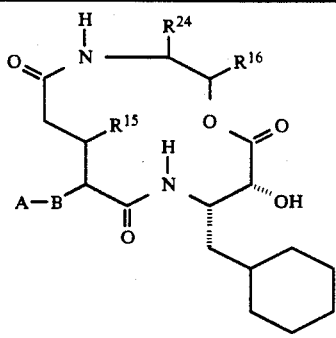

| A—B | R24 (config) | R15 (config) | R16 (config) |
|---|---|---|---|
| " | —H | —H | —CH$_2$—N(morpholine)O(2) |
| " | —H | —H | -i-Bu(1) |
| " | —H | —H | -i-Bu(2) |
| " | —H | —H | -n-Bu(1) |
| " | —H | —H | -n-Bu(2) |
| " | —H | —H | -n-pentyl(1) |
| " | —H | —H | -n-pentyl(2) |
| " | —H | —H | —CH$_2$CH$_2$—N(morpholine)O(1) |
| " | —H | —H | —CH$_2$CH$_2$—N(morpholine)O(2) |
| CH$_3$OCH$_2$O-piperidine-C(O)-CH(CH$_2$Ph)-NH— | —H | —H | —CH$_2$—N(morpholine)O(1) |
| " | —H | —H | —CH$_2$—N(morpholine)O(2) |
| morpholine-C(O)CH$_2$CH$_2$N(CH$_3$)C(O)O-CH(CH$_2$Ph)-C(O)N(CH$_3$)— | —H | —H | —CH$_2$—N(morpholine)O(1) |
| morpholine-C(O)CH$_2$CH$_2$N(CH$_3$)C(O)O-CH(CH$_2$Ph)-C(O)N(CH$_3$)— | —H | —H | —CH$_2$—N(morpholine)O(2) |
| morpholine-C(O)CH$_2$CH$_2$N(CH$_3$)C(O)CH$_2$CH(CH$_2$Ph)-C(O)N(CH$_3$)— | —H | —H | —CH$_2$—N(morpholine)O(1) |

TABLE I-continued
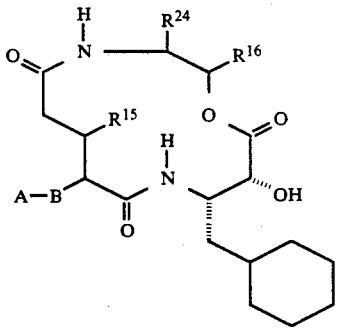
| A—B | $R^{24}$ (config) | $R^{15}$ (config) | $R^{16}$ (config) |
|---|---|---|---|
| 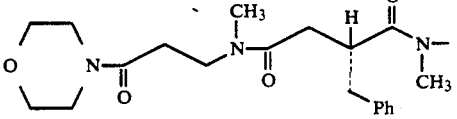 | —H | —H | 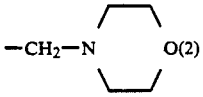 O(2) |
| 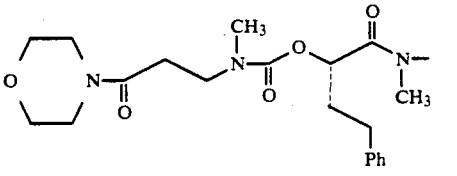 | —H | —H | 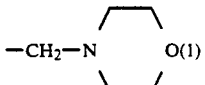 O(1) |
| 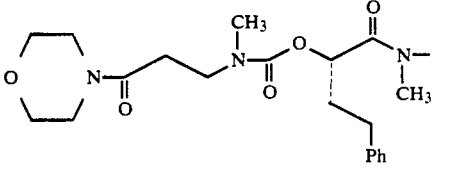 | —H | —H | 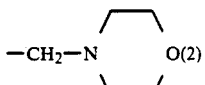 O(2) |
| 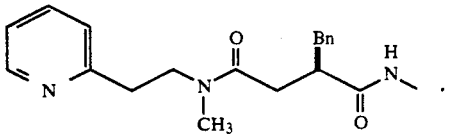 | —H | —H | 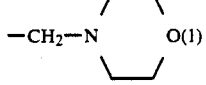 O(1) |
| 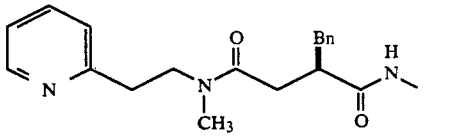 | —H | —H | 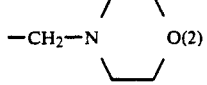 O(2) |
| 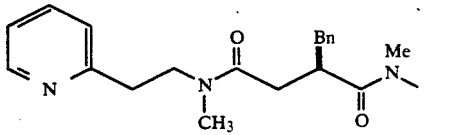 | —H | —H | 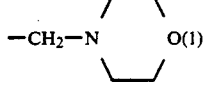 O(1) |
| 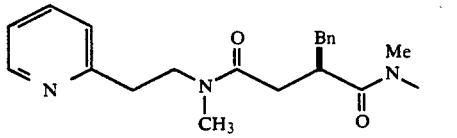 | —H | —H | 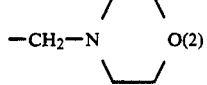 O(2) |

TABLE II

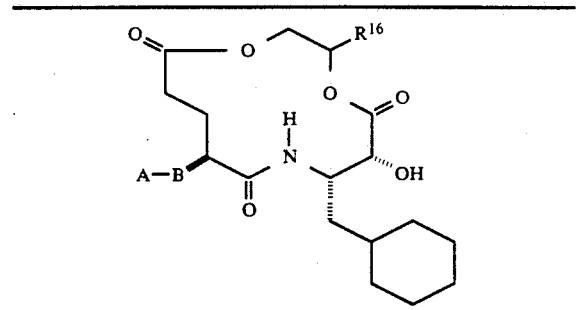

| A—B | R$^{16}$(configuration) |
|---|---|
| BocPhe—NH— | H |
| tBuCH$_2$CONH(CH$_2$)$_2$COPhe—NH— | H |
| BocPhe—NH— | —CH$_2$—N(morpholine) O(1) |
| BocPhe—NH— | —CH$_2$—N(morpholine) O(2) |
| BocPhe—NH— | -n-Bu(1) |
| BocPhe—BH— | -n-Bu(2) |
| 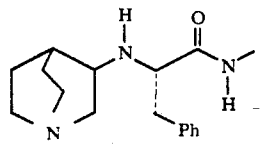 | —H |
| 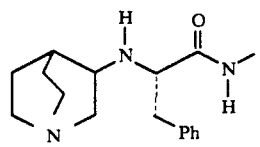 | —CH$_2$—N(morpholine) O(1) |
| 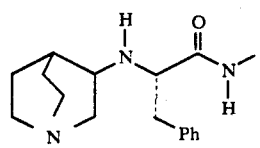 | —CH$_2$—N(morpholine) O(2) |
| 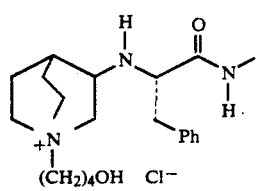 | -i-Bu(1) |
| 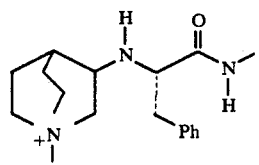 | -i-Bu(2) |
| 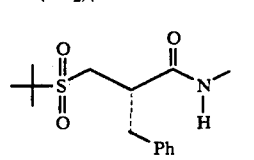 | -i-Bu(1) |

TABLE II-continued

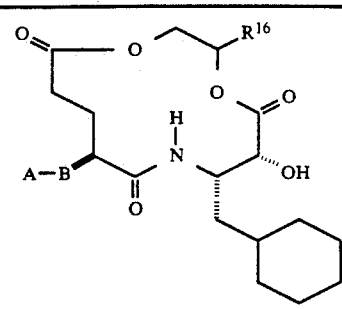

| A—B | R$^{16}$(configuration) |
|---|---|
| 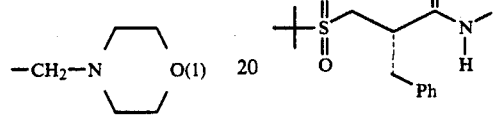 | -i-Bu(2) |
| 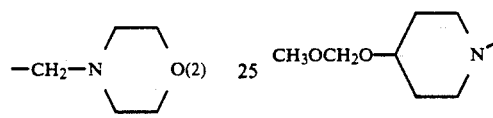 | —CH$_2$—N(morpholine) O(1) |
| 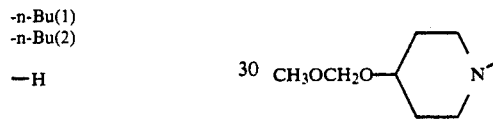 | —CH$_2$—N(morpholine) O(2) |
|  | —CH$_2$—N(morpholine) O(1) |
| 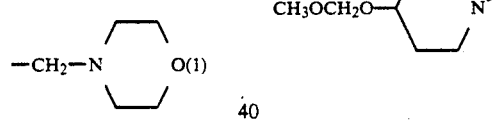 | —CH$_2$—N(morpholine) O(2) |

TABLE III

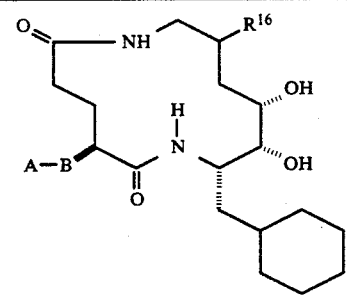

| A—B | R$^{16}$(diastereomer) |
|---|---|
| BocPhe—NH— | H |
| tBuCH$_2$CONH(CH$_2$)$_2$COPhe—NH— | H |
| BocPhe—NH— | 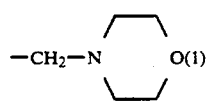 —CH$_2$—N(morpholine) O(1) |

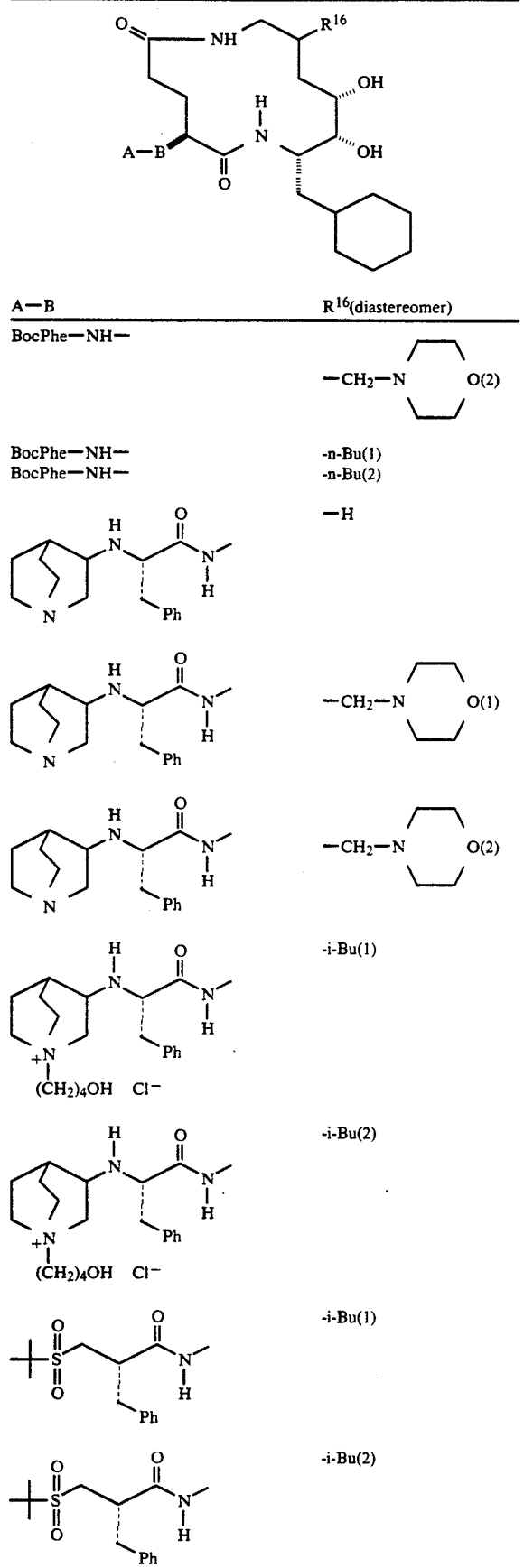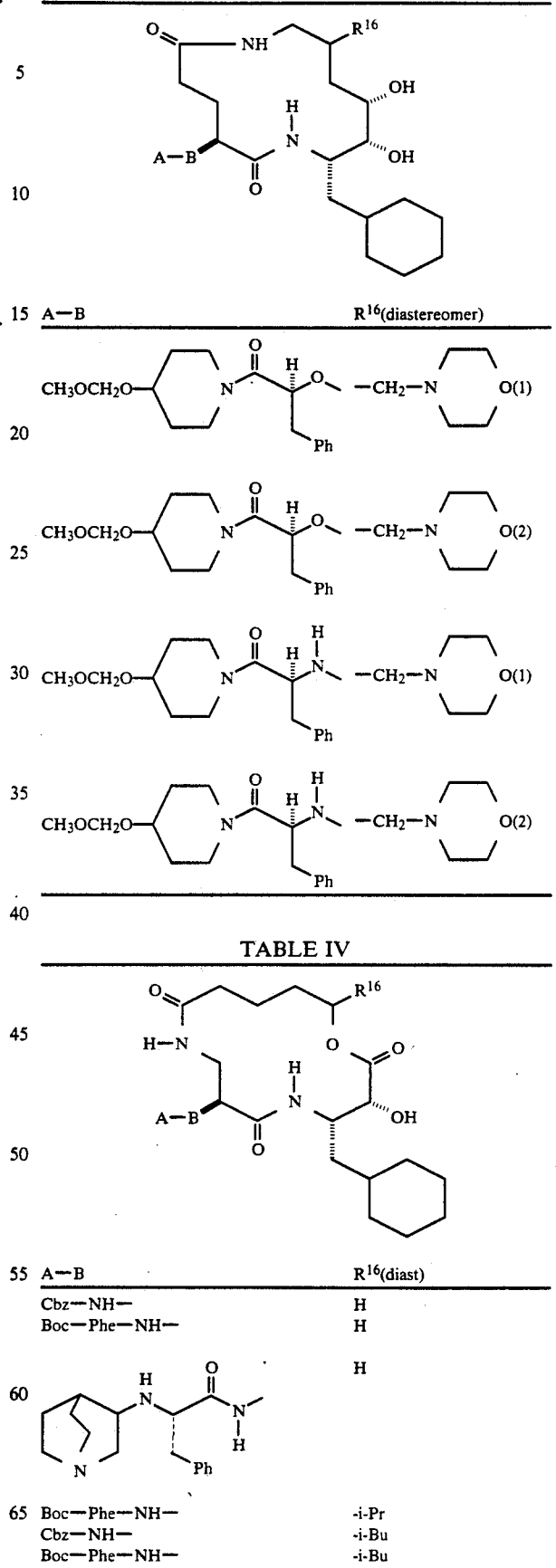

TABLE IV-continued

Structure (common to entries below):

A—B—[CH(CH2-chain with HN-C(=O) loop)]—C(=O)—NH—CH(CH2-cyclohexyl)—CH(OH)—C(=O)—O—CH(R16)—(CH2)3—C(=O)—NH— (macrocycle)

| A—B | R16(diast) |
|---|---|
| Cbz—NH— | —CH2—N(morpholino) O(1) |
| Boc—Phe—NH— | —CH2—N(morpholino) O(1) |
| Boc—Phe—NH— | —CH2—N(morpholino) O(2) |
| tBuSO2—CH2—CH(CH2Ph)—C(=O)—NH— | —CH2—N(morpholino) O(1) |
| (quinuclidin-3-yl)NH—CH(CH2Ph)—C(=O)—NH— | —CH2—N(morpholino) O(1) |
| Cbz—NH— | n-Bu(2) |
| Boc—Phe—NH— | n-Bu(1) |
| Boc—Phe—NH— | n-Bu(2) |
| Cbz—NH— | neoPent(1) |
| Cbz—NH— | neoPent(2) |
| Boc—Phe—NH— | neoPent(1) |
| Boc—Phe—NH— | neoPent(2) |
| CH3OCH2—(4-piperidyl)—N—C(=O)—CH(CH2Ph)—OCH3— | —CH2—N(morpholino) O(1) |
| CH3OCH2—(4-piperidyl)—N—C(=O)—CH(CH2Ph)—OCH3— | —CH2—N(morpholino) O(2) |
| CH3OCH2—(4-piperidyl)—N—C(=O)—CH(CH2Ph)—NH— | —CH2—N(morpholino) O(1) |
| CH3OCH2—(4-piperidyl)—N—C(=O)—CH(CH2Ph)—NH— | —CH2—N(morpholino) O(2) |

TABLE V

Macrocyclic structure with substituents R24, R15, R16, and cyclohexylmethyl group.

| A—B | R24 (config) | R15 (diast) | R16 (config) |
|---|---|---|---|
| BocPhe—NH— | Me(S) | H | H |
| tBuCH2CONH(CH2)2COPhe—NH— | Me(S) | H | H |
| BocPhe—NH— | Me(R) | H | H |
| tBuCH2CONH(CH2)2COPhe—NH— | Me(R) | H | H |
| BocPhe—NH— | Et(R) | H | H |
| tBuCH2CONH(CH2)2COPhe—NH— | Et(R) | H | H |
| BocPhe—NH— | H | Me(1) | H |
| tBuCH2CONH(CH2)2COPhe—NH— | H | Me(1) | H |

TABLE V-continued

[Structure: macrocyclic compound with A—B, R15, R24, R16 substituents, containing OH, cyclohexylmethyl group, and ester/amide linkages]

| A—B | R24 (config) | R15 (diast) | R16 (config) |
|---|---|---|---|
| tBuCH2CONH(CH2)2COPhe—NH— | H | Me(2) | H |
| BocPhe—NH— | H | H | H |
| tBuCH2CONH(CH2)2COPhe—NH— | H | H | H |
| (Z-piperidin-4-yl)CH2—NHCOPhe—NH— | H | H | H |
| (piperidin-4-yl)CH2—NHCOPhe—NH— | H | H | H |
| Cbz—NH— | H | H | —CH2—N(morpholino) O(1) |
| Cbz—NH— | H | H | —CH2—N(morpholino) O(2) |
| BocPhe—NH— | H | H | —CH2—N(morpholino) O(1) |
| BocPhe—NH— | H | H | —CH2—N(morpholino) O(2) |
| tBuCH2CONH(CH2)2COPhe—NH— | H | H | n-Bu(1, 2) |
| BocPhe—NH— | H | H | n-Bu(1) |
| BocPhe—NH— | H | H | n-Bu(2) |
| [quinuclidinyl-NH-CH(CH2Ph)-C(O)NHMe] | H | H | i-Bu(1) |
| [quinuclidinyl-NH-CH(CH2Ph)-C(O)NHMe] | H | H | i-Bu(2) |
| [quinuclidinyl-NH-CH(CH2NA)-C(O)NHMe] | H | H | i-Bu(1) |
| BocPhe—NH— | H | H | n-Hex(1) |
| BocPhe—NH— | H | H | n-Hex(2) |
| BocPhe—NH— | H | H | n-Pent(1) |
| BocPhe—NH— | H | H | n-Pent(2) |

TABLE V-continued
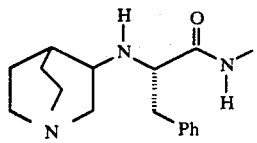
| A—B | R24 (config) | R15 (diast) | R16 (config) |
|---|---|---|---|
| BocPhe—NH— | H | H | Et(1) |
| BocPhe—NH— | H | H | Et(2) |
| Cbz—NH— | H | H | i-Bu(2) |
| BocPhe—NH— | H | H | i-Bu(1) |
| BocPhe—NH— | H | H | i-Bu(2) |
| 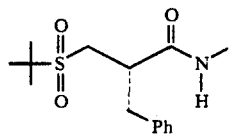 | H | H | i-Bu(2) |
| BocPhe—NH— | H | H | 4-HO—Bu(1, 2) |
| BocPhe—NH— | H | H | neoPent(2) |
| 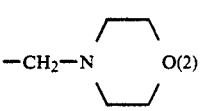 | H | H | 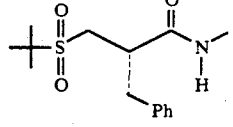 —CH$_2$—N O(2) |
| 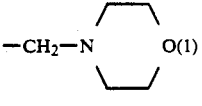 | H | H | 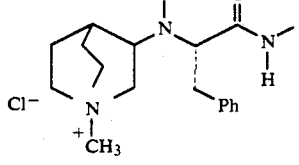 —CH$_2$—N O(1) |
| 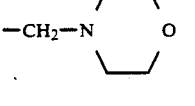 | H | H | 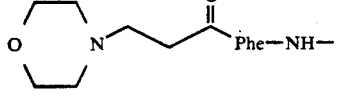 —CH$_2$—N O |
| 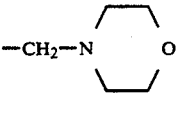 | H | H | 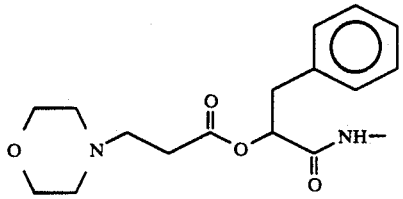 —CH$_2$—N O |
| 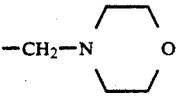 | H | H | —CH$_2$—N O |
| Boc—D—Pro—Phe—NH— | H | H | 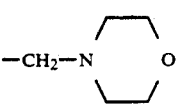 —CH$_2$—N O |

TABLE V-continued
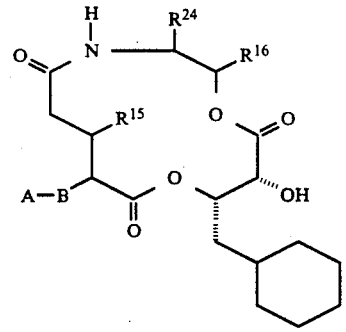
| A—B | R$^{24}$ (config) | R$^{15}$ (diast) | R$^{16}$ (config) |
|---|---|---|---|
| D—Pro—Phe—NH— | H | H | —CH$_2$—N(morpholino) |
| tBu—CH$_2$CONH(CH$_2$)$_2$CO—Phe—NH— | H | H | —CH$_2$—N(morpholino) |
| Boc—NH—C(CH$_3$)$_2$CH$_2$CO—Phe—NH | H | H | —CH$_2$—N(morpholino) |
| NH$_2$—C(CH$_3$)$_2$CH$_2$CO—Phe—NH— | H | H | —CH$_2$—N(morpholino) |
| 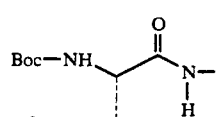 | H | H | —CH$_2$—N(morpholino) |
| 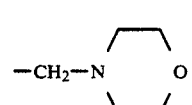 | H | H | —CH$_2$—N(morpholino) |
| 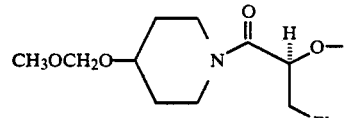 | H | H | —CH$_2$—N(morpholino) |
| 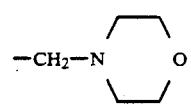 | —CH$_3$(R) | —H | —CH$_2$N(morpholino O(R)) |
| " | —CH$_3$(R) | —H | —CH$_2$N(morpholino O(S)) |

TABLE V-continued

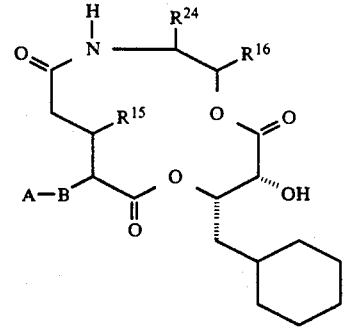

| A—B | R²⁴ (config) | R¹⁵ (diast) | R¹⁶ (config) |
|---|---|---|---|
| " | —CH₃(S) | —H | —CH₂N⟨morpholine⟩O(S) |
| " | —CH₃(S) | —H | —CH₂N⟨morpholine⟩O(R) |
| " | —CH₃(R) | —H | -i-Bu(R) |
| " | —CH₃(R) | —H | -i-Bu(S) |
| " | —CH₃(S) | —H | -i-Bu(S) |
| " | —CH₃(S) | —H | -i-Bu(R) |

TABLE VI

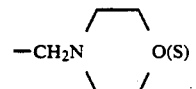

| A—B | R¹⁶(config) |
|---|---|
| BocPhe—NH— | H |
| tBuCH₂CONH(CH₂)₂COPhe—NH— | H |
| BocPhe—NH— | —CH₂N⟨morpholine⟩O(1) |
| BocPhe—NH— | —CH₂N⟨morpholine⟩O(2) |
| BocPhe—NH— | -n-Bu(1) |
| BocPhe—NH— | -n-Bu(2) |
| (quinuclidinyl-NH-CH(CH₂Ph)-C(O)NHMe)— | —H |

TABLE VI-continued

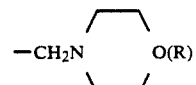

| A—B | R¹⁶(config) |
|---|---|
| (quinuclidinyl-NH-CH(CH₂Ph)-C(O)NHMe)— | —CH₂N⟨morpholine⟩O(1) |
| (quinuclidinyl-NH-CH(CH₂Ph)-C(O)NHMe)— | —CH₂N⟨morpholine⟩O(2) |
| (N⁺-(CH₂)₄OH quinuclidinyl-NH-CH(CH₂Ph)-C(O)NHMe)— Cl⁻ | -n-Bu(1) |

TABLE VI-continued

[Structure with R¹⁶ group, A-B linkage, and cyclohexyl substituent]

| A—B | R¹⁶(config) |
|---|---|
| [quinuclidinium-NH-CH(CH₂Ph)-C(O)NH- with (CH₂)₄OH Cl⁻] | -n-Bu(2) |
| [t-Bu-SO₂-CH₂-CH(CH₂Ph)-C(O)NH-] | -i-Bu(1) |
| [t-Bu-SO₂-CH₂-CH(CH₂Ph)-C(O)NH-] | -i-Bu(2) |
| CH₃OCH₂-[piperidine]-N-C(O)-CH(OMe)-(CH₂Ph)- | -CH₂-N(morpholine) O(1) |
| CH₃OCH₂-[piperidine]-N-C(O)-CH(OMe)-(CH₂Ph)- | -CH₂-N(morpholine) O(2) |
| CH₃OCH₂-[piperidine]-N-C(O)-CH(NHMe)-(CH₂Ph)- | -CH₂-N(morpholine) O(1) |
| CH₃OCH₂-[piperidine]-N-C(O)-CH(NHMe)-(CH₂Ph)- | -CH₂-N(morpholine) O(2) |

TABLE VII

[Structure containing sulfonyl, benzyl, glutamyl, and cyclohexylmethyl moieties terminating in -Z]

where Z is selected from

- -O-C(O)-CH(NH₂)-CH(CH₃)₂ (valine ester)
- -O-C(O)-CH(NH₂)-(n-butyl chain) (norleucine ester)
- -O-C(O)-CH₂-N(CH₃)₂
- -O-C(O)-CH₂CH₂-NH₂
- -O-C(O)-CH₂CH₂-C(O)OH

TABLE VIII

[Structure containing sulfonyl, benzyl, glutamyl, cyclic lactone, and cyclohexylmethyl moieties with -Z]

where Z is selected from the group:

- -O-C(O)-CH(NH₂)-CH(CH₃)₂

TABLE VIII-continued
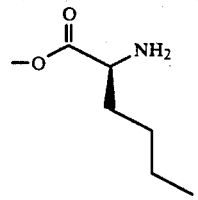
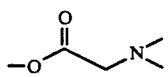
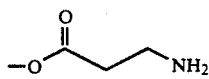
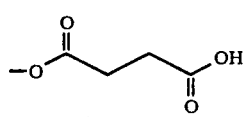
TABLE IX
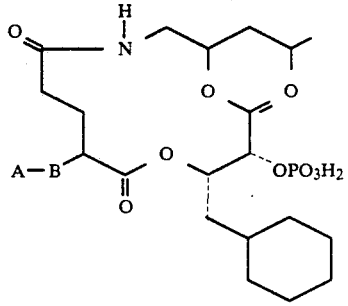
TABLE IX-continued
where A—B is selected from
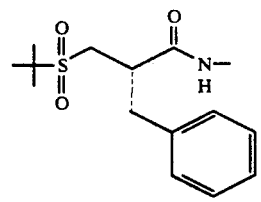
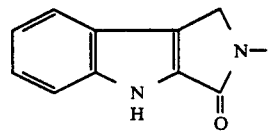
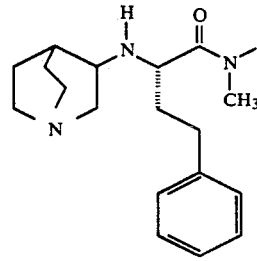
TABLE X
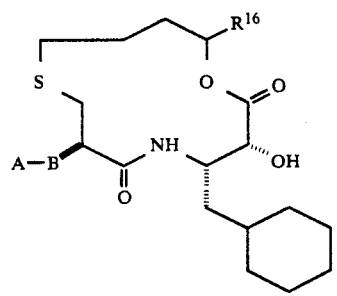
| A—B | R16 |
|---|---|
| BocPhe | H |
| BocPhe | 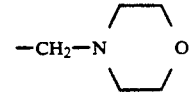 |
| 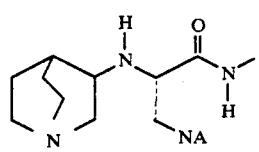 | 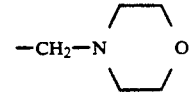 |

TABLE X-continued
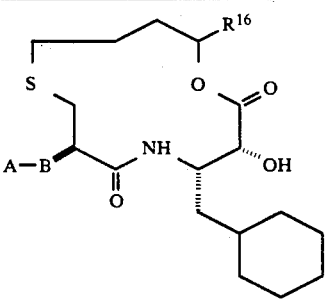
| A—B | R¹⁶ |
|---|---|
| 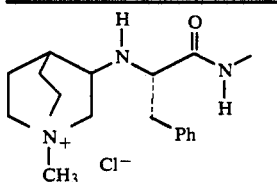 | 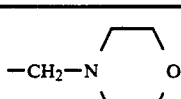 |
| 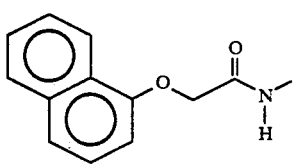 | 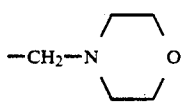 |
| 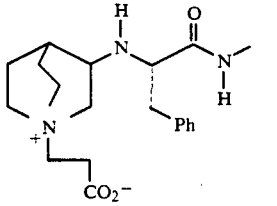 | 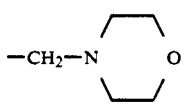 |
| 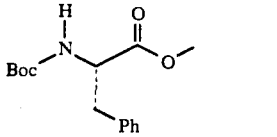 | 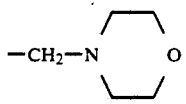 |
| 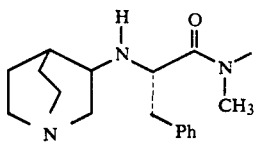 | 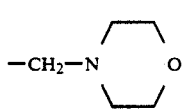 |
| 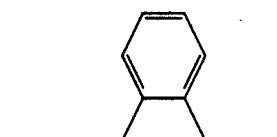 | 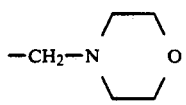 |
| 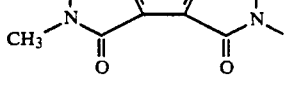 |  |

TABLE X-continued
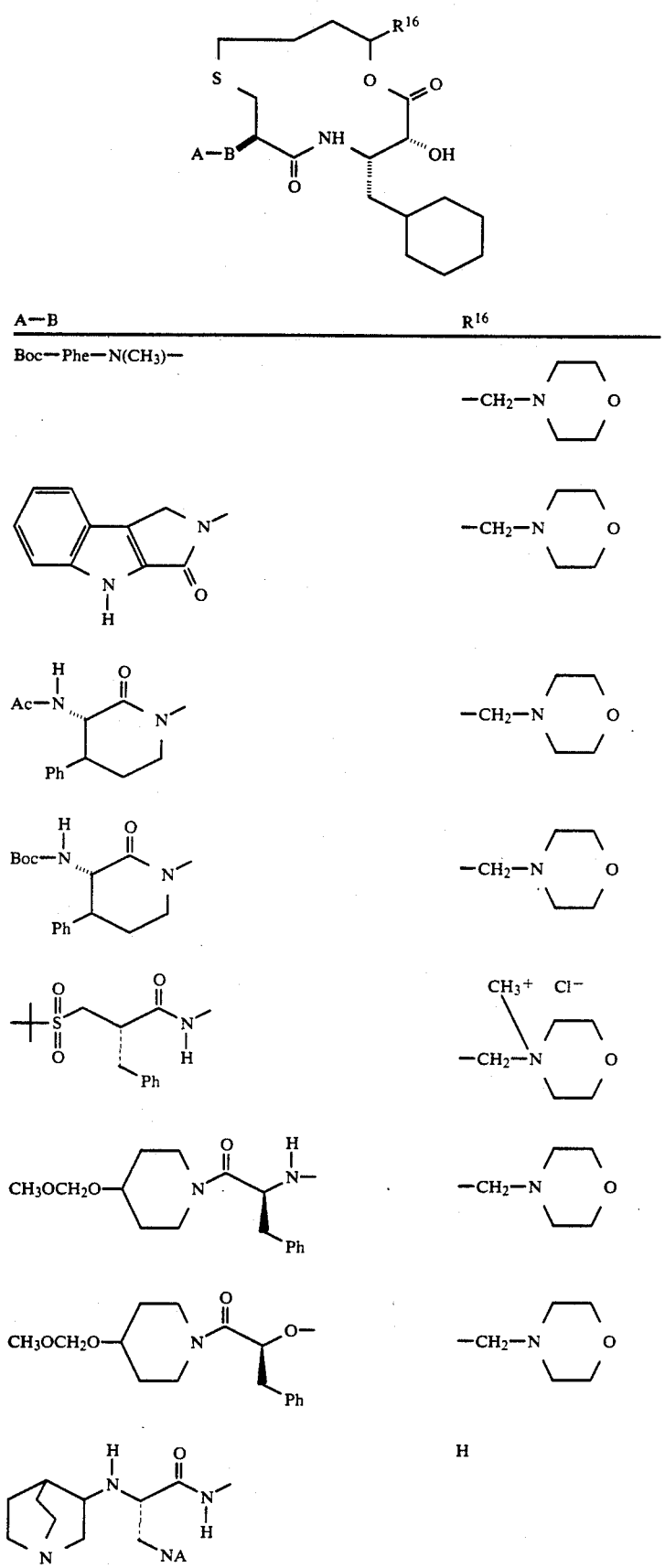

TABLE X-continued
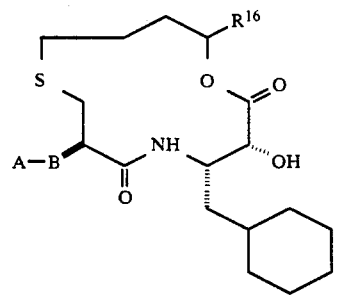
| A—B | R[16] |
|---|---|
|  | H |
| 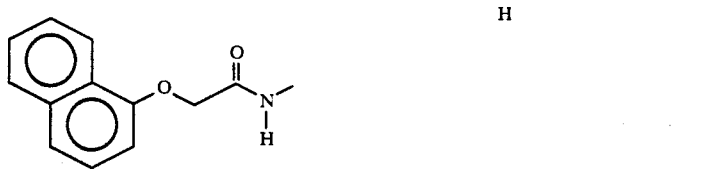 | H |
|  | H |
|  | H |
| | 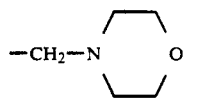 |
| 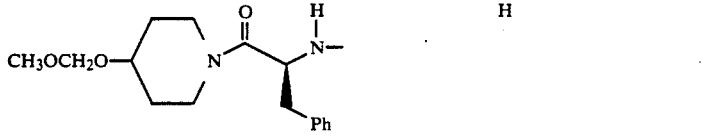 | H |
| 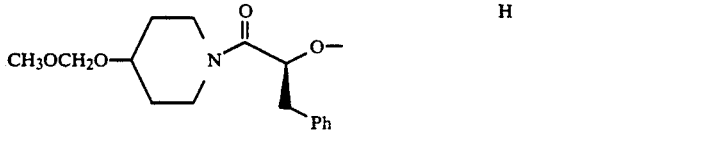 | H |
|  | H |

TABLE X-continued
| A—B | $R^{16}$ |
|---|---|
| 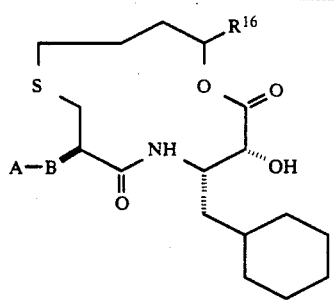 | H |
| 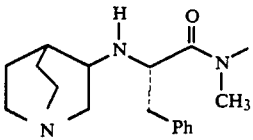 | H |
| 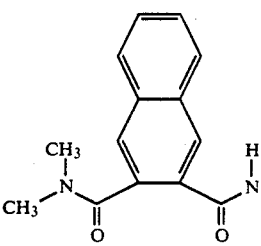 | H |
| Boc—Phe—N(CH$_3$)— | H |
| 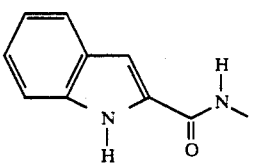 | H |
| 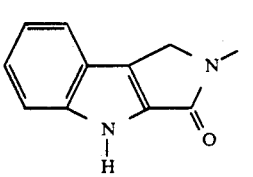 | H |
| 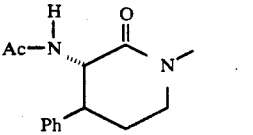 | H |
| 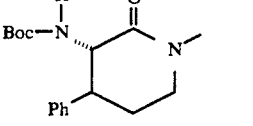 | 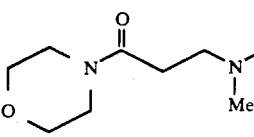 |

TABLE X-continued
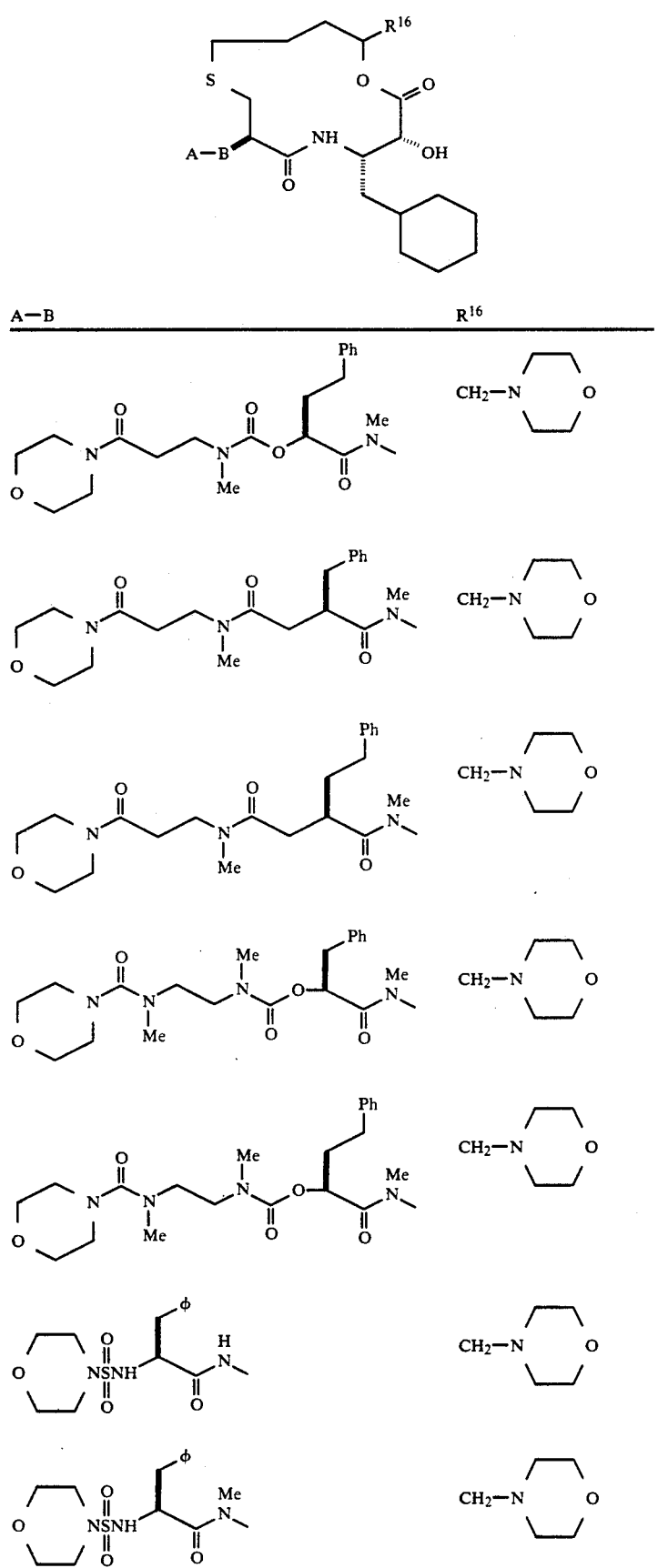

TABLE X-continued

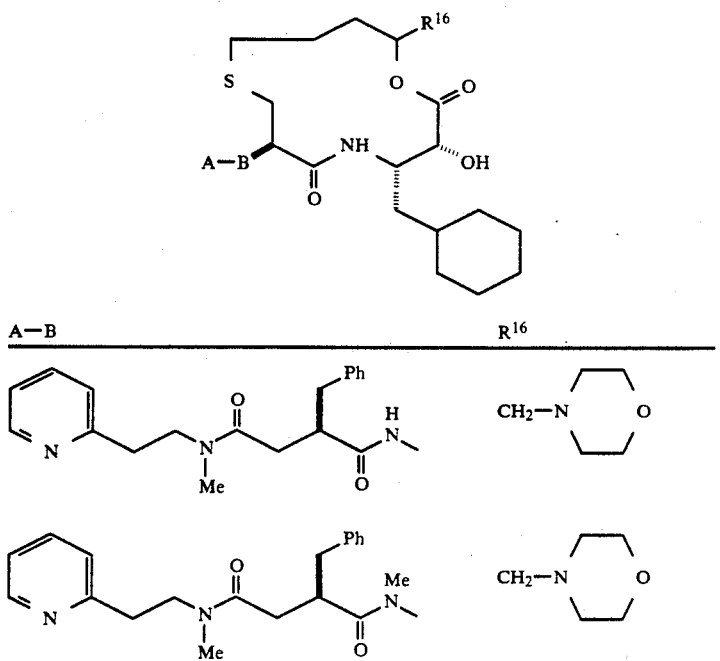

| A—B | R$^{16}$ |
|---|---|
| (2-pyridyl-CH$_2$CH$_2$-N(Me)-C(O)-CH$_2$-CH(CH$_2$Ph)-C(O)-NH-Me) | CH$_2$-morpholine |
| (2-pyridyl-CH$_2$CH$_2$-N(Me)-C(O)-CH$_2$-CH(CH$_2$Ph)-C(O)-N(Me)-Me) | CH$_2$-morpholine |

The abbreviations used herein have the following meaning:

| Abbreviated Designation | |
|---|---|
| | Amino Acid/Residue |
| Nor-ACHPA | 3(S)-amino-4-cyclohexyl-2(R)-hydroxybutanoic acid |
| HomoPhe | 2(S)-amino-4-phenylbutanoic acid |
| (p-MeO)Phe | L-para-methoxyphenylalanine |
| Phe | L-phenylalanine |
| Ser | L-serine |
| Thr | L-threonine |
| BocGlu(Bn) | N$^\alpha$-t-butoxycarbonyl glutamic acid α-benzyl ester |
| | Protecting Group |
| Nal | L-3-(1-naphthyl)-alanine |
| Tyr | L-tyrosine |
| BOC (Boc) | t-butyloxycarbonyl |
| CBZ (Cbz) | benzyloxycarbonyl(carbobenzoxy) |
| DNP | 2,4-dinitrophenyl |
| IPOC | isopropoxycarbonyl |
| | Activating Group |
| HBT(HOBt) | 1-hydroxybenzotriazole hydrate |
| HOSu | N-hydroxysuccinimide |
| | Condensing Agent |
| DCCI (DCC) | dicyclohexylcarbodiimide |
| DPPA | diphenylphosphorylazide |
| EDC | 1-(3-dimethylaminopropyl)-3-ethyl-carbodiimide hydrochloride |
| | Reagent |
| (BOC)$_2$O | di-t-butyl dicarbonate |
| DIBAL | diisobutylaluminum hydride |
| DIPEA | diisopropylethylamine |
| DMAP | 4-(dimethylamino)pyridine |
| TEA | triethylamine |
| DCHA | dicyclohexylamine |
| TFA | trifluoroacetic acid |
| LAH | lithium aluminum hydride |
| LDA | lithium diisopropylamide |
| MCPBA | 3-chloroperoxybenzoic acid |
| NMM | N-methyl morpholine |
| PPTS | pyridinium para toluenesulfonate |
| Cbz-OSu | N-carbobenzyloxy succinimide |
| TBAF | tetra-n-butylammonium fluoride |
| TsOH | p-toluenesulfonic acid |
| | Solvent |
| HOAc (AcOH) | acetic acid |
| DMF | dimethylformamide |
| DMSO | dimethyl sulfoxide |
| EtOAc | ethyl acetate |
| EtOH | ethanol |
| Et$_2$O | ether |
| MeOH | methanol |
| THF | tetrahydrofuran |
| Hex | hexane |
| NA | 1-naphthyl |

As can be seen, a unique aspect and essential feature of the present invention is the incorporation of certain cyclic elements thereby inparting enhanced oral absorption as renin inhibitors.

The Formula I compounds can be used in the form of salts derived from inorganic or organic acids and bases when there is an acidic or basic function. Included among such acid addition salts are the following: acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobrimide, hydroiodide, 2-hydroxyethanesulfonate, lactate, maleate, methanesulfonate, 2-naphthalenesulfonate, nicotinate, oxalate, palmoate, pectinate, persulfate, 3-phenylpropionate, picrate, pivalate, propionate, succinate, tartrate, thiocyanate, tosylate,. and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups can be quarternized with such agents as lower alkyl halides, such as methyl, ethyl, propyl, and butyl chloride, bromides and iodides: dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others. Water or oil-soluble or dispersible products are thereby obtained.

The novel compounds of the present invention inhibit the angiotensinogen-cleaving action of the natural proteolytic enzyme, renin, and possess an excellent degree of activity in treating renin-associated hypertension and hyperaldosteronism, congestive heart failure and glaucoma.

The compounds of the invention are useful in treating hypertension. They are also of value in the management of acute and chronic congestive heart failure. These compounds may also be expected to be useful in the treatment of secondary hyperaldosteronism, primary and secondary pulmonary hyperaldosteronism, primary and secondary pulmonary hypertension, renal failure such as diabetic nephropathy, glomerulonephritis, scleroderma, glomerular sclerosis, proteinuria of primary renal disease, end stage renal disease, renal transplant therapy, and the like, renal vascular hypertension, left ventricular dysfunction, diabetic retinopathy and in the management of vascular disorders such as migraine, Raynaud's disease, luminal hyperplasia, and to minimize the atherosclerotic process. The application of the compounds of this invention for these similar disorders will be apparent to those skilled in the art.

The compounds of this invention are also useful to treat elevated intraocular pressure and to enhance retinal blood flow and can be administered to patients in need of such treatment with typical pharmaceutical formulations such as tablets, capsules, injectables and the like as well as topical ocular formulations in the form of solutions, ointments, inserts, gels, and the like. Pharmaceutical formulations prepared to treat intraocular pressure would typically contain about 0.1% to 15% by weight, preferably 0.5% to 2% by weight, of a compound of this invention.

For these purposes the compounds of the present invention may be administered parenterally, by inhalation spray, orally, or rectally in dosage unit formulations containing conventional non-toxic pharmaceutically acceptable carriers, adjuvants and vehicles. The term parenteral as used herein includes subcutaneous injections, intravenous, intramuscular, intrasternal injection of infusion techniques. In addition to the treatment of warm-blooded animals such as mice, rats, horses, dogs, cats, etc., the compounds of the invention are effective in the treatment of humans.

The pharmaceutical compositions may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

The inhibitors of this invention may also be administered in the form of suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials are cocoa butter and polyethylene glycols.

Dosage levels of the order of 2 to 35 grams per day are useful in the treatment of the above indicated conditions. For example, renin-associated hypertension and hyperaldosteronism are effectively treated by the administration of from 30 milligrams to 0.5 grams of the compound per kilogram of body weight per day.

The amount of active ingredient that may be combined with the carrier materials to produce a single dosage form will vary depending upon the host treated and the particular mode of administration.

It will be understood, however, that the specific dose level for any particular patient will depend upon a variety of factors including the activity of the specific compound employed, the age, body weight, general health, sex, diet, time of administration, route of administration, rate of excretion, drug combination and the severity of the particular disease undergoing therapy.

Thus, in accordance with the present invention there is further provided a pharmaceutical composition for treating renin-associated hypertension and hyperaldosteronism, comprising a pharmaceutical carrier and a therapeutically effective amount of Compound I.

The renin-inhibitory compounds of the present invention may also be utilized in diagnostic methods for the purpose of establishing the significance of renin as a causative or contributory factor in hypertension or hyperaldosteronism in a particular patient. For this purpose the novel inhibitors of the present invention may be administered in a single dose of from 0.1 to 10 mg per kg of body weight.

Both in vivo and in vitro methods may be employed. In the in vivo method, a novel compound of the present invention is administered to a patient, preferably by intravenous injection, although parenteral administration is also suitable, at a hypotensive dosage level and as a single dose, and there may result a transitory fall in blood pressure. This fall in blood pressure, if it occurs, indicates supranormal plasma renin levels.

An in vitro method which may be employed involves incubating a body fluid, preferably plasma, with a novel compound of the present invention and, after deproteinization, measuring the amount of angiotensin II produced in nephrectomized, pentolinium-treated rats. Another in vitro method involves mixing the plasma or other body fluid with a novel compound of the present invention and injecting the mixture into a test animal. The difference in pressor response with and without added peptide is a measure of the renin content of the plasma.

The following method was used for in vitro evaluation of the renin inhibitors of Formula I: The human plasma renin $IC_{50}$ values for inhibitors of Formula I were determined at pH 7.4 following the procedure described in J. Boger, L. S. Payne, D. S. Perlow, N. S. Lohr, M. Poe, E. H. Blaine, E. H. Ulm, T. W. Schorn, B. I. Lamont, T. Y. Lin, M. Kawai, D. H. Rich and D. F. Veber, J. Med. Chem., 28, 1779 (1985).

The following methods were used for in vivo evaluation of the renin inhibitors of Formula I: Intravenous evaluation of renin inhibitors in concious sodium-deficient Rhesus monkeys: Rhesus monkeys, male and female, weighing 2.6–4.5 Kg, were surgically prepared with chronic arterial and venous catheters and vascular access ports for direct monitoring of mean arterial pressure (MAP) and heart rate (HR). The animals were maintained on a low sodium diet (1.2 mmol Na/day) plus fruit for a week, and administered LASIX (furosemide) at 2.5 mg/Kg, intramuscularly the evening prior to the experiment. The animals had been trained to sit quietly in the chairs with water ad libium for the duration of the experiment. The inhibitors were administered by bolus injection using 0.5% acetic acid-5% dextrose in water as the vehicle (0.4 ml/Kg), and MAP and HR were measured. Blood samples were withdrawn at different time intervals beginning at the nadir of hypotensive response. PRA was determined as described above. The responsiveness of the animal during the experiment was verified with the standard inhibitor, SCRIP (Iva-His-Pro-Phe-His-Sta-Leu-Phe-NH$_2$, IC$_{50}$=3.7 nM). The i.v. dose of the standard inhibitor required to lower blood pressure by 50% of the maximal response was determined (ED$_{50}$=0.039 umoles/Kg). Inhibitors were tested at doses which were derived by comparing their IC$_{50}$ values to that of SCRIP. A projected ED$_{50}$ dose for each inhibitor was calculated using the following formula: ED$_{50}$ (Test Inhibitor, umoles/Kg)=ED$_{50}$ (SCRIP) X [IC$_{50}$ (Test Inhibitor)/IC$_{50}$ (SCRIP)], where the IC$_{50}$ values were determined against human plasma renin. In order to assure initial complete inhibition of endogenous monkey renin after i.v. administration, a multiple of projected ED$_{50}$ dose was chosen for each inhibitor. Percent inhibition of monkey PRA, changes in MAP and HR were calculated and plotted against time. The data points are averages of two or more monkey experiments.

Protocol for oral administration of renin inhibitors in conscious sodium-deficient Rhesus monkeys: Rhesus monkeys of either sex were surgically prepared and sodium depleted for administration of compounds orally, as above. The animals were fitted with a nasogastric feeding tube for oral administration of inhibitors. The inhibitors were administered orally as a solution (2.5 ml/Kg) in 0.1M citric acid, and MAP and HR were measured over time. Plasma samples were collected at different time intervals up to 6 hours, and plasma renin activity (PRA) (ng AI/ml/hr) was determined using the RIA method (Travenol genetech's RIA Kit). Percent inhibition of primate PRA and peak changes in MAP and HR were calculated. All data points are an average of 2–5 monkey experiments.

The compounds of the present invention are prepared in accordance with the following reaction schemes and experimental procedures.

SECTION A: PREPARATION OF INTERMEDIATES

The following carboxylic acids, useful in preparing macrocyclic inhibitors of formula I may be prepared by methods described in the following references:

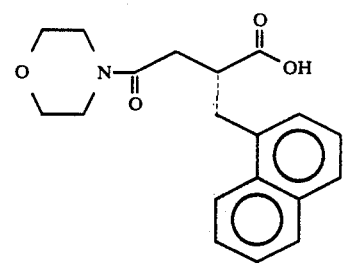

K. Iizuka et al., J. Med. Chem., 31, 704 (1988).

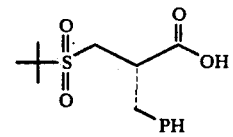

P. Buhlmayer et al., J. Med. Chem., 31, 1839 (1988).

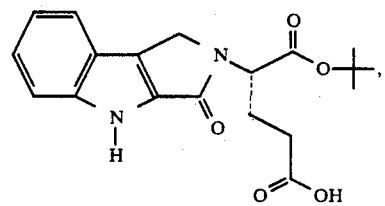

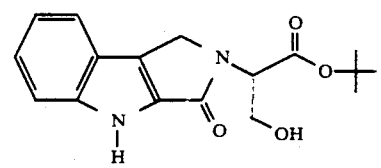

D. J. Kempf et al., "Design and Synthesis of Rigid Heterocyclic Phenylalanine Replacements for Incorporation into Renin Inhibitors," Proceedings of 11th Am. Peptide Symposium, Salk Institute, University of California, San Diego, Jul. 9–14, 1989, ESCOM Scientific Publishers, BV Leiden, The Netherlands.

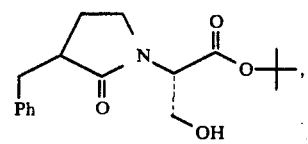

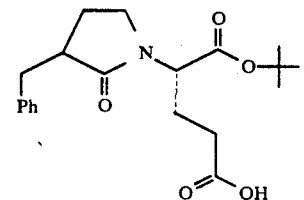

S. Thaisrivongs et al, J. Med. Chem., 31, 1371 (1988).

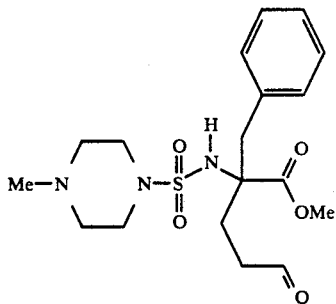

B. De, et. al., European Patent Application No. EP0365992, published May 2, 1990.

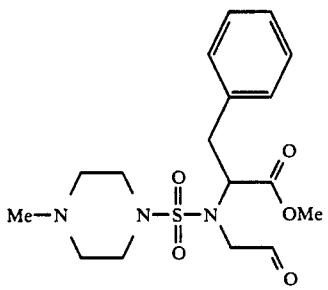

B. De, et. al., European Patent Application No. EP0365992, published May 2, 1990.

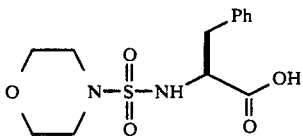

J. M. Hamby et al, EP0380805 A1 published Aug. 8, 1990.

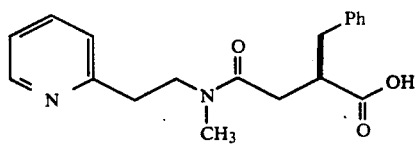

S. H. Rosenberg et al EP0410260 A2 published Jan. 30, 1991.

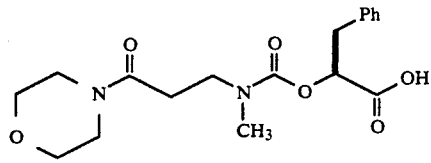

K. Hemmi et al U.S. Pat. No. 4,921,855 published May 1, 1990.

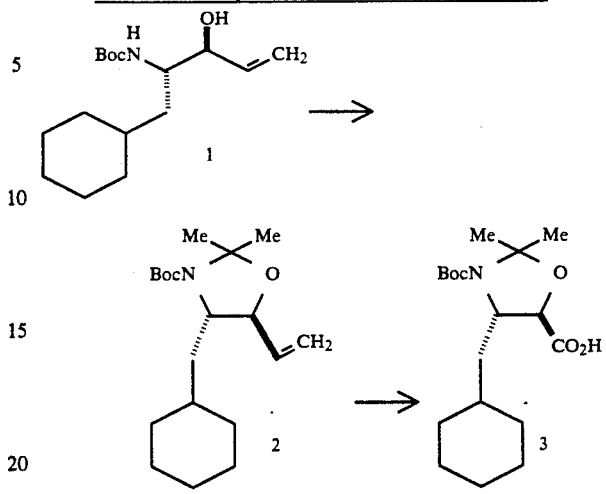

SCHEME 1: Synthesis of norACHPA acetonide, 3

(4S, 5S)-3-tert-Butoxycarbonyl-4-cyclohexylmethyl-2,2-dimethyl-5-vinyloxazolidine (2)

A solution of 34.6 g (122 mmol, 1.0 equiv) of (3S,R,4S)-3-tert-butoxycarbonylamino-5-cyclohexyl-3-hydroxy-1-pentene (1, 6:1 S/R mixture at C-3, prepared according to the procedure of Rosenberg, S. H.; Plattner, J. J.; Luly, J. R.; Eur. Patent Appl. 0 230 266, 1987) and 1.16 g (6.10 mmol, 0.05 equiv) of p-toluenesulphonic acid monohydrate in 530 mL of dichloromethane was cooled to −78° C. and 63.5 g (75.0 mL, 61.0 mmol, 5 equiv) of dimethoxypropane was added. The reaction mixture was stirred at −22° C. overnight and then quenched by the addition of 1.23 g (1.70 mL, 12.2 mmol, 0.1 equiv) of triethylamine. The solution was washed sequentially with 250 mL portions of saturated aqueous sodium bicarbonate solution and 1N aqueous sodium bisulfate solution, dried over anhydrous magnesium sulfate, and concentrated to give 43 g of an oil. Purification by silica gel chromatography (Water's Prep 500, 4% ethyl acetate/hexane) gave 25.9 g (66% yield, >97% diastereomeric purity by 300 MHz $^1$H NMR) of the title compound as an oil: $R_f$ 0.25 (5% ethyl acetate/hexane); $^1$H NMR (300 MHz, CDCl$_3$) δ5.95 (ddd, 1H, J=7.1, 10.3, 17.1 Hz), 5.33 (d, 1H, J=17.1 Hz), 5.23 (d, 1H, J=10.3 Hz), 4.26 (dd, 1H, J=3.5, 7.1 Hz), 3.81 (br s, 1H), 1.98–0.85 (m, 19H), 1.47 (s, 9H); MS(FAB) 378 (M+1+matrix (dithiothreitol)-Boc).

Anal. calcd. for C$_{19}$H$_{33}$NO$_3$: C, 70.55; H, 10.28; N, 4.33. Found: C, 70.45; H, 9.99; N, 4.29.

(4S,5R)-3-tert-Butoxycarbonyl-4-cyclohexylmethyl-2,2-dimethyloxazolidine-5-carboxylic acid (norACHPA acetinide, 3)

To a solution of 25.9 g (80.1 mmol, 1.0 equiv) of (4S,5S)-3-tert-butoxycarbonyl-4-cyclohexylmethyl-2,2-dimethyl-5-vinyloxazolidine (2) in 1500 mL of acetone at room temperature was added in four portions over 3 h a solution of 102.8 g (480 mmol, 6.0 equiv) of sodium periodate and 1.07 g (4.01 mmol, 0.05 equiv) of 50% ruthenium dioxide on carbon in 1500 mL of water. After the final addition, the reaction was judged complete by TLC analysis and excess reagent was quenched by the addition of 14 mL of isopropyl alcohol. The resultant mixture was filtered through celite and concentrated. The aqueous residue was diluted with 2 L of 1:1 1N aqueous sodium bisulfate and 1N aqueous sodium bisulfite and extracted with four 750-mL portions of dichloromethane. The combined organic phases were dried over anhydrous magnesium sulfate and decolorized with activated charcoal. Concentration gave 25.9 g (95%) of a slightly green solid. An analytical sample was prepared by recrystallization from ethyl acetate/hexane: $R_f$ 0.30 (10% MeOH/CH$_2$Cl$_2$); $^1$H NMR (300 MHz, CDCl$_3$) δ4.38 (s, 1H), 4.35 (br s, 1H), 1.93 (br d, J=12 Hz), 1.80–0.85 (m, 12H), 1.66 (s, 3H), 1.58 (s, 3H), 1.48 (s, 9H); MS(FAB) 342 (M+1), 286, 242.

Anal. calcd. for C$_{18}$H$_{31}$NO$_5$: C, 63.32; H, 9.15; N, 4.10. Found: C, 63.38; H, 9.25; N, 4.04.

N$^\alpha$-(Quinuclidin-3(RS)-yl)-Phe-t-butyl ester hydrochloride (4)

To a solution of 9.00 g (56.25 mmol) 3-quinuclidinone and 4.15 g (18.75 mmol) Phe-O-t-Bu in 50 ml methanol was added over a 12 hour period a solution of 2.95 g (46.9 mmol) sodium cyanoborohydride in 13 ml methanol. After stirring for an additional 8 hours, 5.78 g (50.0 mmol) pyridine hydrochloride was added and after 1½ hours stirring, sodium chloride was removed by filtration. The filtrate was concentrated to a foam which was treated with 15 ml methanol and 50 ml ethyl acetate to give a slurry of the byproduct 3-hydroxy quinuclidine hydrochloride (74% of excess) which was removed by filtration. The filtrate was concentrate to an oil and charged with 10 ml methanol to a 5×200 cm column of LH-20 and eluted with methanol. The product fraction contained 6.54 g of a mixture of diastereomers in a 55:45 ratio as established by HPLC.

N$^\alpha$-(Quinuclidin-3(S)-yl)-Phe-t-butyl ester hydrochloride (4S)

A solution of 7.0 g of the isomer mixture (from Example 1) in 25 ml water was treated with 2.62 g sodium bicarbonate bringing the pH to 9.0. The clear solution was lyophilized and the crystalline residue was extracted with 50 ml of acetonitrile. Evaporation of the solvent and treatment with 25 ml ether gave crystals which were filtered off, washed with ether, and dried. The yield was 2.49 g (65%) of an isomer established by x-ray crystal structure analysis to be the S,S-diastereomer hydrochloride.

N$^\alpha$-(Quinuclidin-3(S)-yl)Phe•2 HCl (5S)

A solution of 1.91 g of the 4S in 3 ml concentrated hydrochloric acid was left for 3 hours and then concentrated to an amorphous mass. To remove excess HCl the material was redissolved in 10 ml water and concentrated to yield 1.98 g of the dihydrochloride.

[N$^\alpha$-(N-Methylquinuclidin-3(S)-yl)Phe-O-t-Bu]$^\pm$I$^-$ (6S)

A solution of 406 mg (1.23 mM) of 4S in 2 ml methanol was treated with 310 μl. (5.0 mmol) methyl iodide and 68.3 mg (1.26 mmol) sodium methylate. After 2 hours at room temperature the reaction mixture was concentrated and charged with 4 ml of methanol to a 2.5×210 cm column of LH-20 and eluted with methanol. The product fractions contained 366 mg of product with an NMR spectrum consistent with the assigned structure.

N$^\alpha$-(N-Methylquinuclidin-3(S)-yl)-phenylalanine]$^+$$^-$Cl$^-$•HCl (7S)

A solution of 366 mg (775 μM) of the 6S in 1 ml of water and 2 ml of conc. hydrochloric acid was aged for 2 hours, concentrated and charged with 2 ml methanol to 2.5×210 cm LH20 column and eluted with methanol. The product fraction contained 254 mg of product with NMR and mass spectra consistent with the structure.

N$^\alpha$-(Quinuclidin-3(RS)-yl)Nal-OCH$_3$•HCl (8)

A solution of 2.20 g (8.28 mmol) of 3-(1-Naphthyl)-Ala-OCH$_3$•HCl and 4.02 g (25 mm of 3-Quinuclidinone hydrochloride in 30 ml of methanol was treated over the course of 11 hours with a solution of 1.20 g (20.7 mmol) of sodium cyanoborohydride in 7.5 ml of methanol. After the addition was complete the reaction mixture was allowed to stir for 4 days and then treated with 2.42 g (20.9 mmol) pyridine hydrochloride and after stirring for 3 hours, the solvent was removed using a rotary evaporator. The residue was stirred with 10 ml methanol and the insoluble sodium chloride was removed by filtration and washed with 5 ml methanol. The filtrate was treated with 60 ml ethyl acetate and the solution was seeded with 3-RS-quinuclidinol hydrochloride. The alcohol byproduct was removed by filtration and the filtrate was concentrated in vacuum to an oil. A second crop of this byproduct was removed by crystallization with a solvent mixture consisting of 50 ml ethyl acetate, 50 ml of acetonitrile, and 2 ml of methanol. The filtrate was concentrated in vacuo to 5.36 g of an amorphous residue. This was dissolved in 5 ml of methanol and chromatographed over a 5×200 cm column of LH-20 eluting with methanol. The product-containing fractions were combined and concentrated, yielding 4.4 g of product.

N$^\alpha$-(Quinuclidin-3(S)-yl)Nal-OCH$_3$•HCl (8S)

Using mixtures of acetonitrile and ether, for crystallization, a total of 440 mg of the 3(S)-diastereomer was obtained from the above mixture (8).

N$^\alpha$-(Quiniclidin-3(RS)-yl)Nal-OH dihydrochloride (9)

N$^\alpha$-(Quiniclidin-3(RS)-yl)Nal-OMe•HCl (0.5 g) (8) was dissolved in 6N HCl (10 ml), and the mixture was refluxed for 4 hours and then allowed to stand at room temperature overnight. The mixture was then concentrated in vacuo to dryness, and the residue was dried in a vaccum desciator over NaOH and dryness, and the residue was dried in a vaccum desciator over NaOH and P$_2$O$_5$ overnight to give the desired product as a foam (0.55 g). $^1$H NMR (300 MHz, CD$_3$OD): δ1.9–2.2 (m, 3H), 2.45 (m, 2H), 3.16–3.95 (m. 7H), 4.2–4.5 (m, 3H), 7.35–7.7 (m, 4H), 7.88 (dd, 2H), 8.3 (d, 1H), MS(FAB): m/e 325 (MH+).

N$^\alpha$-(2,2,6,6-Tetramethylpiperidin-4-yl)-Phe-O-t-Bu (10)

A solution of 11.55 g (60.2 mmol) 2,2,6,6-tetramethylpiperidin-4-one hydrochloride and 4.44 g (20 mmol) Phe-O-t-Bu in 40 ml of methanol was treated over an eight hour period with a solution of 3.19 g (50.8 mmol) sodium cyanoborohydride in 6 ml of methanol. After stirring overnight a solution of 8.21 g (71.0 mmol) pyridine hydrochloride in 20 ml of methanol was added and stirring continued for 1½ hour. Sodium chloride was removed by filtration, and the filtrate was concentrated to an oil. The byproduct 2,2,6,6-tetramethylpiperidin-3-ol (69.5% of excess) crystallized on addition of 40 ml ethyl acetate and 40 ml of acetonitrile, and was removed by filtration. The filtrate was concentrated to an amorphorus mass which was charged with 10 ml methanol to a 5×200 cm LH-20 column and eluted with methanol. Evaporation of the solvent from the product-containing fractions and crystallization from 10 ml acetonitrile afforded 5.34 g (61.5%) of product, which had NMR and mass spectra in accord with assigned structure.

N$^\alpha$-(1-Ethylpiperidin-3(RS)-yl)Phe-O-t-Bu (11)

A solution of 8.18 g (50.0 mmol) 1-ethyl-3-piperidone HCl, 5.15 g (20.0 mM) Phe-O-t-Bu and 1.64 g (19.3 mM) sodium acetate in 250 ml methanol was treated over a 14 hour period with a solution of 1.88 g (30.0 mmol) sodium cyanoborohydride in 10 ml methanol. After stirring overnight, 3.47 g (30.0 mmol) pyridine hydrochloride was added, and after 2 hour stirring sodium chloride was removed by filtration and the reaction mixture was concentrated to an oil. This was dissolved in 16 ml methanol and chromatographed on a 5×200 cm LH-20 column eluted with methanol. The product fraction contained 4.01 g (67.2%) of a mixture of diastereomers with NMR and mass spectra in accord with the assigned structure.

Methyl 2-Methanesulfonyloxy-3-phenylpropionate (12)

To a stirred solution of phenylalanine (16.5 g, 0.1 mole) in 2N sulfuric acid at 0° C., was added sodium nitrite (10.5 g, 1.5 equiv) in small portions over a period of 0.5 hours and the mixture stirred overnight. Aqueous phase was extracted with ether (5×250 mL) and the ethereal extracts were washed with saturated aqueous solution of sodium chloride, dried over anhydrous magnesium sulfate and concentrated to give phenyllactic acid (1 equiv) in methanol (15 equiv) at 0° C. and the mixture stirred at room temperature overnight. Removal of volatiles in vacuo and chromatographic purification of the oil (20-25% ethyl acetate in hexane) gives methyl 2-hydroxy-3-phenylpropionate. $^1$H NMR (300 MHz, CDCl$_3$): δ7.33-7.196 (m, 5H), 4.451 (dd, 1H), 3.764 (s, 3H), 3.1225 (dd, 4.45 Hz, 13.95 Hz, 1H), 2.9575 (dd, 7 Hz, 14 Hz, 1H), 2.787 (br s, 1H). A dichloromethane solution of methyl 2-hydroxy-3-phenylpropionate is treated with triethylamine (1.1 equiv) and methanesulfonyl chloride (1.1 equiv) at 0° C. Upon completion of reaction, the mixture is dissolved in dichloromethane/ether and washed with saturated aqueous solution of sodium chloride, dried and concentrated. Purification of crude material by flash column chromatography (40% ethyl acetate in hexane) gives methyl 2-methanesulfonyloxy-3-phenyl-propionate (1.6 g, 93%).

$^1$H NMR (300 MHz CDCl$_3$): δ7.358-7.233 (m, 5H), 5.173 (dd, 4.26 Hz, 8.8 Hz, 1H), 3.793 (s, 3H), 3.301 (dd, 4.23 Hz, 14.38 Hz, 1H), 3.1295 (dd, 8.8 Hz, 14.3 Hz, 1H), 2.766 (s, 3H).

3-Acetylthioquinuclidine (13)

To a THF (300 mL) solution of triphenylphosphine (42 g, 160 mmol, 2 equiv) at 0° C. was added diisopropyl azodicarboxylate (32 mL, 162 mmol) to produce a pale yellow solid. A THF (300 mL) solution of 3-quinuclidinol (10.2 g, 80.2 mmol) and thiolacetic acid was added dropwise to the yellow reaction mixture and stirred overnight. THF was removed in vacuo and the residue was dissolved in ether (500 mL) and extracted with 10% HCl (4×150 mL). The aqueous acidic phase was back extracted with ether/ethyl acetate (75 mL/25 mL) and then neutralized to pH 7 by the addition of sodium bicarbonate cautiously in small portions. The aqueous layer was then basified to pH 9-10 by adding a few drops of 10N NaOH, then extracted with dichlormethane (5×200 mL), dried over anhydrous sodium sulfate and concentrated. Purification by flash column chromatography using 5% MeOH in chloroform as eluent gave 3-acetylthioquinuclidine (10.5 g, 71%).

$^1$H (300 MHz, CDCl$_3$): δ3.725-3.63 (m, 1H), 3.427 (dd, 10.23 Hz, 13.7 Hz), 2.9-2.75 (dd, 4H), 2.678 (dd, 5.7 Hz, 14.2 Hz, 1H), 2.326 (S, 3H), 1.9-1.82 (m, 1H), 1.81-1.675 (m, 3H), 1.53-1.4 (m, 1H).

3-Mercaptoquinuclidine (14)

Acetylthioquinuclidine it treated with sodium methoxide in methanol. Upon completion of hydrolysis the sovent is removed in vacuo to obtain 3-mercaptoquinclidine which is used in the next step without further purification.

2-(Quinuclidin-3-yl)thio-3-phenylpropionic acid (15)

To a stirred solution of 3-mercaptoquinuclidine in DMF at 0° C. is added sodium hydride (1 equiv) and the mixture stirred for 0.5 hours. A solution of methyl-2-methanesulfonyloxy-3-phenylpropionate (1 equiv) in DMF or THF is added to the reaction mixture at 0° C. and the resulting mixture stirred. After completion of reaction, methanol is added dropwise to quench the reaction. The volatiles are removed in vacuo and the residue is purified by flash chromatography to obtain the methyl ester which is sponified with aqueous sodium hydroxide (1N, 1 equiv) in methanol to afford 2-(quinuclidin-3-yl)-thio-3-phenylpropionic acid.

2-(Quinuclidin-3-yl)oxy-3-phenylpropionic acid (16)

To a slurry of potassium hydride (1 equiv) in THF at 0° C. is added 3-quinuclidinol (1 equiv) and the mixture stirred for 0.25 hours. A THF solution of methyl-2-methanesulfonyloxy-3-phenylpropionate (1 equiv) is added to the reaction mixture and stirred until completion of reaction. The reaction is quenched by slow addition of methanol, the mixture is concentrated and the residue is purified by flash chromatography to afford methyl ester which is treated with aqueous sodium hydroxide (1N, NaOH) to produce the 2-(quinuclidin-3-yl)oxy-2-phenylpropionic acid.

Methyl 2-Benzylacrylate (17)

Methyl 2-benzylacrylate is prepared by the method of J. Harley-Mason et al., Tetrahedron, 36, 1063 (1980).

Methyl-2-(quinuclidin-3-yl)thiomethyl-3-phenylpropionate (18)

3-Acetylthioquinuclidine is hydrolyzed to 3-mercaptoquinuclidine by treating with sodium methoxide in methanol. To the sodium salt of 3-mercaptoquinuclidine in methanol at 0° C., is added methyl 2-benzylacrylate and the mixture stirred for a few hours. Upon completion of reaction, methanol is removed and the residue is subjected to flash column chromatography to give methyl ester of 48. The methyl ester is then saponified by treating with 1N NaOH in methanol to provide 2-(quinuclidin-3-yl)thiomethyl-3-phenylpropionic acid.

2-(Quinuclidin-3-yl)sulfonylmethyl-3-phenylpropionic acid (19)

Methyl-2-(quinuclidin-3-yl)thiomethyl-3-phenylpropionate is treated with 2 equivalents of m-chloro-peroxybenzoic acid in CH$_2$Cl$_2$. The reaction mixture is filtered to remove m-chloro-benzoic acid and the filtrate is concentrated. The residue is purified by flash chromatography and then subjected to the action of 6N HCl-HoAc (1:1) at 60° C. for 24 hours, providing the title compound.

SECTION B: PREPARATION OF MACROCYCLIC RENIN INHIBITORS OF FORMULA I where D=—CONH— or —COO—, W=—NH—, Z=—OH AND Y=—OCO—

Schemes 2, 3 and 4 illustrate the preparation of macrocyclic renin inhibitos of Formula I in which D=—CONH— or —COO—, W=—NH—, Z—OH, and Y=—OCO—. In Schemes 2 and 4, N-alpha-Cbz-glutamic acid alpha-t-butyl ester is coupled with an (optionally substituted) amino alcohol to form an N-delta-substituted analog of glutamine. The free hydroxyl of the resulting amide is then esterified with Boc-Nor-ACHPA acetonide (3), to afford a macrocyclization precursor. The Boc and acetonide protecting groups are then removed during acid treatment from the Nor-ACHPA element with concomittant removal of the t-butyl ester from the glutamine element. The resulting deprotected intermediate is cyclized using one of the methods (A, B, or C) described below. Removal of the amino-terminal Cbz protecting group, followed by coupling of the resulting amino-derivative with an acylating agent such as a carboxylic acid component (for example, Boc-Phe), an acid chloride or a sulfonyl chloride (see Methods D and E below), provides inhibitors such as 26 (Scheme 2).

In Scheme 3, the protected glutamic acid derivative is esterified with an epoxy alcohol, and the resulting ester intermediate is allowed to react with a nucleophile such as morpholine. The free hydroxyl group is then esterified as described above with Boc-Nor-ACHPA acetonide to prepare the macrocyclization precursor, which is treated as described above. The epoxy alcohol in Scheme 3 may be replaced with suitably protected diols which may optionally bear substituent(s) comprising the substituents $R^{16}$ and $R^{24}$ in Formula I.

As will be obvious to those skilled in the art, functional groups within the (optional) substituent of the amino alcohol which is coupled to N-alpha-Cbz-Glutamic acid alpha-t-butyl ester as described above (the $R^{16}$ substitutent in Formula I) may require protection during the following steps of the synthesis. In these cases, protecting groups are chosen so as to be compatible with the Boc, Cbz, and t-butyl ester protecting groups used for other amine and carboxylic acid groups as described in the general synthetic route above. Examples are the t-butyldimethylsilyl group for alcohols, the trichloroethoxycarbonyl group for amines and trimethylsilylethyl ester for carboxylic acids.

General Procedure for Esterification Using EDC/DMAP.

A solution of the appropriate acid and alcohol (0.95-1.2 equiv) in dichloromethane (0.1-0.33M) was cooled to 0° C. and dimethylaminopyridine (DMAP, 0.05-0.1 equiv) and 1-(3-dimethylaminopropyl)-3-ethylcarbodiimide hydrochloride (EDC, 1.5-3 equiv) were added. The mixture was stirred at 0° C. for 2-16 hours, until the reaction was judged complete by TLC analysis. The solution was then diluted with ethyl acetate, washed sequentially with 1N aqueous sodium bisulfate, water, saturated aqueous sodium bicarbonate and saturated aqueous sodium chloride, dried over anhydrous magnesium sulfate and concentrated. Purification by silica gel chromatography provided the desired ester in good yield.

General Procedure for Macrocyclization. Method A:

The macrocycle precursor was deprotected with 1:1 dichloromethane/triflouroacetic acid at room temperature until the reaction was judged complete by TLC analysis (4-6 hours). The solution was concentrated and trace amounts of acid were removed azeotropically with tetrahydrofuran and toluene. The resultant oil was dried over $P_2O_5$/KOH under vacuum for several hours and then dissolved in tetrahydrofuran to form a 0.001M solution. The solution was cooled to 0° C. and treated with N-methyl morpholine (1.1 equiv), hydroxybenzotriazole (HOBt, 4.0 equiv), and 1-(3-dimethylaminopropyl)-3-ethylcarbodiimide hydrochloride (EDC, 4.0 equiv). The mixture was allowed to warm to room temperature and was stirred for a total of 5-6 days. Solvent was removed in vacuo. The residue was dissolved in ethyl acetate, washed sequentially with 1N aqueous sodium bisulfate, water, saturated aqueous sodium bicarbonate and saturated aqueous sodium chloride, dried over anhydrous magnesium sulfate and concentrated. Purification by silica gel and/or Sephadex LH-20 gel chromatography provided the macrocycles.

General Procedure for Macrocyclization. Method B:

Deprotection was carried out as above. The deprotected material was dissolved in dimethylformamide (DMF) to form a 0.002M solution. The solution was cooled to 0° C. and treated with diphenylphosphorylazide (2.0 equiv) and triethylamine (2.2 equiv). After the reaction mixture was stirred at 0° C. for several hours, 7.5° C. for 3 days, and room temperature for 16 h, the DMF was removed in vacuo. Isolation and purification were performed as described for Macrocyclization Method A.

General Procedure for Macrocyclization. Method C:

Deprotection with TFA in dichloromethane was carried out as described above. A solution of the deprotected material in THF (0.38 mmol in 5 mL, 0.076M) was added via a syringe pump over a period of 20 hours to a refluxing solution of EDC (2 equiv), N,N-dimethylaminopyridine (DMAP, 3 equiv) and DMAP.HCl (2 equiv) in chloroform (25 mL). After addition, the reaction mixture added to 500 mL of ethyl acetate and washed with saturated aqueous solution of sodium bicarbonate, sodium chloride, dried over anhydrous magnesium sulfate and concentrated. Purification by flash column chromatography or MPLC on silica gel afforded the macrocycles in yields higher than those by Macrocyclization Methods A and B.

General Procedure for Deprotection and Acylation of Macrocycles. Method D.

A solution of macrocycle in the indicated solvent was stirred with 10% Pd/C under 1 atm of hydrogen for several hours until the deprotection was judged complete by TLC analysis. The mixture was filtered through celite and concentrated. The resultant oil was dissolved in dichloromethane (0.05-0.2M) unless otherwise indicated, cooled to 0° C., and treated with the appropriate acid (1.1-3 equiv), hydroxybenzotriazole (HOBt, 2.0 equiv), and 1-(3-dimethylaminopropyl)-3-ethylcarbodiimide hydrochloride (EDC, 2.0 equiv). The solution was stirred overnight with gradual warming to room temperature and then diluted with ethyl acetate, washed sequentially with 1N aqueous sodium bisulfate, saturated aqueous sodium bicarbonate and saturated aqueous sodium chloride, dried over anhydrous magnesium sulfate and concentrated. Purification by silica gel and/or Sephadex LH-20 gel chromatography provided the acylated macrocycles.

General Procedure for Deprotection and Acylation of Macrocycles. Method E.

A solution of macrocycle in 4:1 trifluoroacetic acid/methyl sulfide was stirred at room temperature for 6-8 hours or overnight. The solution was concentrated and trace amounts of acid were removed azeotropically with methanol and toluene. The resultant oil was dried over $P_2O_5$/KOH under vacuum for several hours and then suspended in dichloromethane or the indicated solvent. Upon addition of triethylamine (1.1 equiv), the oil dissolved. The solution was cooled to 0° C. and treated with the appropriate acid, HOBt, and EDC.

Isolation and purification were performed as described for Deprotection and Acylation Method D.

9H), 1.15 (ddd, J=4.8, 8.7, 13.4 Hz, 1H), 0.86 (t, J=6.3 Hz, 6H); MS(FAB) 218 (M+1), 162.

SCHEME 2

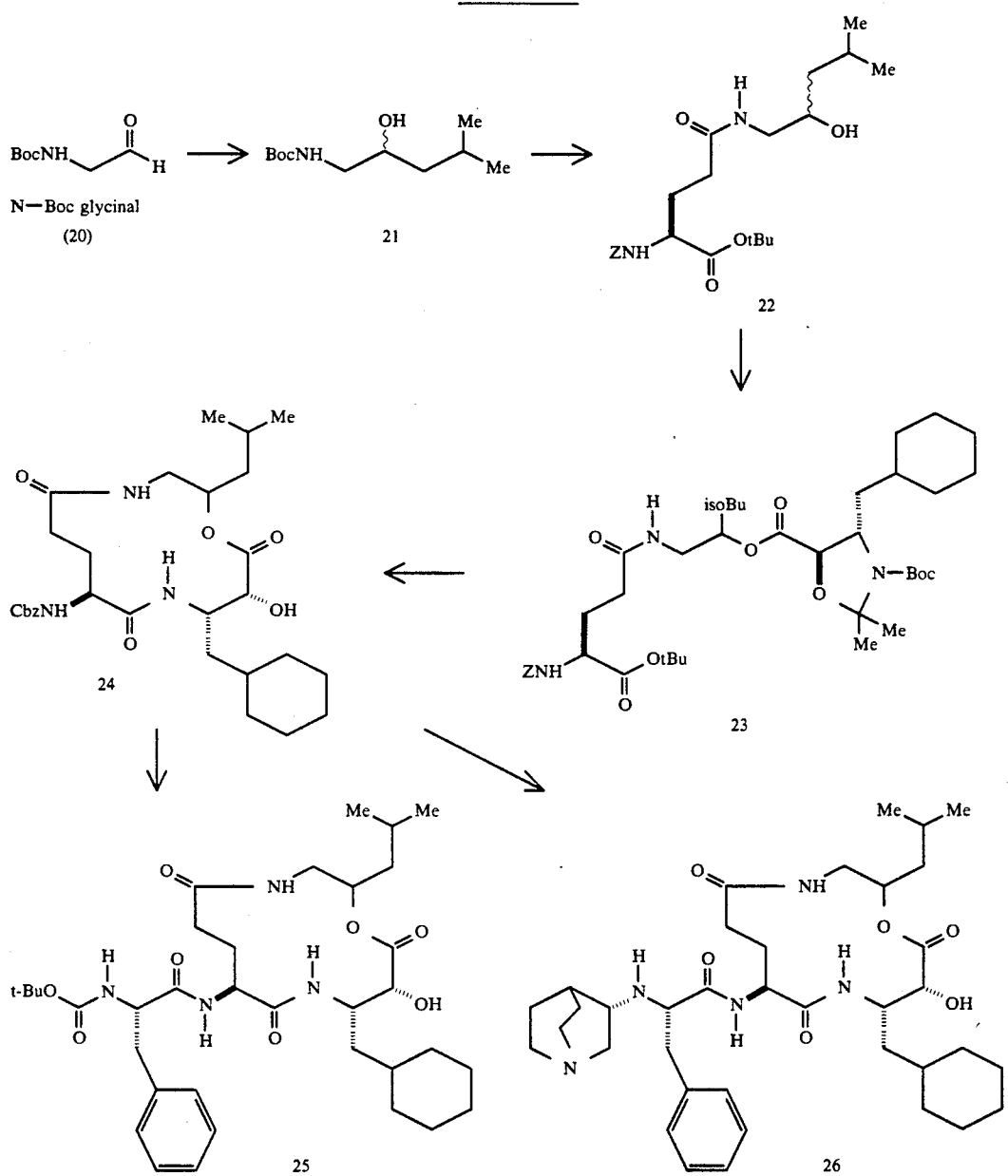

N-Boc amino alcohol 21

To a −78° C. solution of 547 mg (3.44 mmol) of N-Boc glycinal (20) in 17 mL of diethyl ether was added 5.16 mL (10.3 mmol, 3 equiv) of isobutylmagnesium chloride (2.0M in diethyl ether). After five minutes, the solution was warmed to 0° C. and stirred for 24 h. The reaction mixture was then diluted with 300 mL of ethyl acetate, washed with 1N aqueous sodium bisulfate, dried over magnesium sulfate and concentrated. Purification by flash chromatography (20×150 mm silica gel, 30% ethyl acetate/hexane) gave 291 mg (39%) of the title compound as a clear oil: $R_f$ 0.20 (30% ethyl acetate/hexane); $^1$H NMR (300 MHz, CDCl$_3$) δ5.19 (br t, J=5.4 Hz, 1H), 3.69 (br m, 1H), 3.24–3.19 (br m, 1H), 3.09 (br s, 1H), 2.92 (br pent, J=6.4 Hz, 1H), 1.72 (hept, J=6.4 Hz, 1H), 1.45–1.29 (m, 1H), 1.39 (s,

Glutamine derivative 22

A solution of 430 mg (1.98 mmol) of N-Boc amino alcohol 21 in 1:1 dichloromethane/trifluoroacetic acid was stirred at room temperature for 4 hours. The solution was concentrated and trace amounts of acid were removed azeotropically with methanol and toluene. The resultant oil was dried over P$_2$O$_5$/KOH under vacuum for several hours. The deprotected amino alcohol was dissolved in dichloromethane and 0.28 mL (1.98 mmol, 1 equiv) of triethylamine. After cooling to 0° C., 1210 mg (2.37 mmol, 1.2 equiv) of Z-Glu-OtBu DCHA, 401 mg (2.97 mmol, 1.5 equiv) of hydroxybenzotriazole (HOBt), and 569 mg (2.97 mmol) of 1-(3-dimethylaminopropyl)-3-ethylcarbodiimide hydrochloride (EDC) were added. The reaction mixture was stirred overnight. The resultant dark brown solution was then diluted with 300 mL of ethyl acetate, washed sequentially with 100-mL portions of 1N aqueous sodium bisulfate, water, saturated aqueous sodium bicarbonate and saturated aqueous sodium chloride, dried over anhydrous magnesium sulfate and concentrated. Purification by flash chromatography (20×150 mm silica gel, 70% ethyl acetate/hexane) provided 465 mg (54%) of the title compound: $R_f$ 0.39 (75% ethyl acetate/hexane); $^1$H NMR (300 MHz, CDCl$_3$) δ7.31–7.22 (m, 5H), 6.54 (br s, 1H), 5.81 (br t, J=6.3 Hz, 1H), 5.06 (s, 2H), 4.19 (br m, 1H), 3.73 (br m, 1H), 3.54–3.40 (m, 0.5H), 3.45 (d, J=4.8 Hz, 0.5H), 3.34 (br m, 0.5H), 3.22 (d, J=5.1 Hz, 0.5H), 3.09 (br pent, J=6.8 Hz, 0.5H), 2.88 (ddd, J=4.4, 8.7, 13.0 Hz, 0.5H), 2.27–2.10 (m, 3 HO, 2.00–1.70 (m, 2H), 1.42 (s, 9H), 1.25–1.10 (m, 2H) 0.88 (t, J=6.3 Hz, 6H); MS(FAB) 437 (M+1), 381, 337.

Anal. calcd. for C$_{23}$H$_{36}$N$_2$O$_6$ ¼H$_2$O: C, 62.64; H, 8.34; N, 6.35. Found: C, 62.82; H, 8.48; N, 6.37.

Cyclization Precursor 23

Nor-ACHPA acetonide (3, 322 mg, 0.943 mmol, 1.2 equiv) was coupled with 343 mg (0.786 mmol, 1.0 equiv) of glutamine derivative 22 using 276 mg (1.18 mmol, 1.5 equiv) of EDC and 9.6 mg (0.079 mmol, 0.1 equiv) of DMAP in 4 mL of dichloromethane for 6 hours according to the general procedure. Purification by MPLC (2 Lobar B-columns in series, 40% ethyl acetate/hexane) gave 198 mg (33%) of one diastereomer ($R_f$ 0.24 (35% ethyl acetate/hexane)) and 257 mg (43%) of another diastereomer, the title compound, as an oil: $R_f$ 0.20(35% ethyl acetate/hexane); $^1$H NMR (300 MHz, CDCl$_3$) δ7.34–7.26 (m, 5H), 6.38 (br t, J=4.9 Hz, 1H), 5.59 (br d, J=7.0 Hz, 1H), 5.09 (br s, 3H), 4.35 (br s, 1H), 4.35–4.15 (m, 2H), 3.58–3.45 (m, 1H), 3.27 (br pent, J=6.1 Hz, 1H), 2.31–2.10 (m, 3H), 1.86–0.80 (m, 17H), 1.64 (s, 3H), 1.54 (s, 3H), 1.45 (s, 9H), 1.44 (s, 9H), 0.93–0.88 (overlapping d, 6H); MS(FAB) 760 (M+1), 660, 604.

Anal. calcd. for C$_{41}$H$_{65}$N$_3$O$_{10}$: C, 64.80; H, 8.62; N, 5.53. Found: C, 64.52; H, 8.77; N, 5.47.

Macrocyle 24:

Macrocyclization of 257 mg (0.338 mmol) of compound 23 was carried out according to the general procedure (Method A) described above. Purification by flash chromatography (20×150 mm silica gel, 200 mL of 2.5% and 200 mL of 5% methanol/dichloromethane) provided 93.8 mg (51%) of the title compound: $R_f$ 0.25 (5% methanol/dichloromethane); $^1$H NMR (300 MHz, d$_6$-DMSO) δ7.53 (br t, J=6.5 Hz, 1H), 7.34–7.27 (m, 5H), 6.77 (br d, J=9.2 Hz, 1H), 5.59 (br d, J=7.2 Hz, 1H), 5.067 (br s, 1H), 5.01 (br s, 2H), 4.13 (br m, 3H), 3.61 (dd, J=10.7, 13.3 Hz, 1H), 2.83 (d, J=13.3 Hz, 1H), 2.19–1.98 (m, 2H), 1.73–0.85 (m, 18H), 0.87 (t, J=7.7 Hz, 6H); MS(FAB) 546 (M+1).

Anal. calcd. for C$_{29}$H$_{43}$N$_3$O$_7$ 3/2H$_2$O: C, 60.82; H, 8.10; N, 7.34. Found: C, 60.76; H, 7.74; N, 7.27.

Macrocycle 25

A solution of 60.7 mg (0.111 mmol) of 24 in 2 mL DMF was deprotected according to Method E and then dissolved in 1 mL of DMF and treated with 88.5 mg (0.334 mmol, 3.0 equiv) of BocPhe, 45.1 mg (0.231 mmol, 3.0 equiv) of HOBt, and 64.0 mg (0.334 mmol, 3.0 equiv) of EDC according to the general procedure (Method A). Purification by flash chromatography (20×150 mm silica gel; 50 mL of dichloromethane, 100-mL portions each of 1.75%, 2.5%, 4%, and 5% methanol/dichloromethane) gave 55.9 mg (76%) of the title compound: $R_f$ 0.21 (5% methanol/dichloromethane); $^1$H NMR (300 MHz, CD$_3$OD/CDCl$_3$) δ7.27–7.20 (m, 5H), 5.21 (m, 1H), 4.50 (dd, J=4.4 10.0 Hz, 1H), 4.40–4.28 (m, 2H), 4.24 (s, 1H), 3.73 (dd, J=10.6, 13.7 Hz, 1H), 3.10–2.98 (m, 2H), 2.77 (dd, J=9.5, 13.8 Hz, 1H), 2.38–2.16 (m, 2H), 2.07–1.82 (m, 3H), 1.75–0.85 (m, 15H), 1.34 (s, 9H), 0.96–0.91 (overlapping d, 6H); MS(FAB) 659 (M+1), 603, 559.

Anal. calcd. for C$_{35}$H$_{54}$N$_4$O$_8$: C, 63.81; H, 8.26; N, 8.50. Found: C, 63.50; H, 8.52; N, 8.36.

Macrocycle 26

A solution of 19.0 mg (0.0348 mmol) of 24 was deprotected according to the general procedure (Method E) and treated with 7.65 μL (0.0696 mmol, 2 equiv) of N-methyl morpholine, 19.0 mg (0.0418 mmol, 1.2 equiv) of N-quinuclidin-3-(S)-yl phenylalanine, 4.94 mg (0.0365 mmol, 1.05 equiv) of HOBt, and 10.0 mg (0.0522 mmol, 1.5 equiv) of EDC. The solution was stirred overnight with gradual warming to room temperature and then concentrated. The residue was submitted directly to flash chromatography (20×150 mm silica gel, 85:15:3 dichloromethane/methanol/ammonium hydroxide) and purified further by MPLC (Sephadex LH-20, methanol) to give 5.0 mg (21%) of the title compound: $R_f$ 0.26 (85:15:3 dichloromethane/methanol/ammonium hydroxide); 1H NMR (300 MHz, CD$_3$OD) δ7.33–7.22 (m, 5H), 5.23 (m, 1H), 4.50 (dd, J=4.9, 10.2 Hz, 1H), 4.37 (m, dt, J=1.8, 7.3 Hz, 1H), 4.26 (d, J=1.7 Hz, 1H), 3.72 (dd, J=10.5, 14.0 Hz, 1H), 3.29–2.94 (m, 9H), 2.74 (dd, J=8.6, 13.3 Hz, 1H), 2.58 (br d, J=12.5 Hz, 1H), 2.36 (td, J=4.4, 16.3 Hz, 1H), 2.24–2.14 (m, 2H), 2.06–0.85 (m, 21H), 0.97–0.92 (overlapping d, 6H); MS(FAB) 668 (M+1).

SCHEME 3

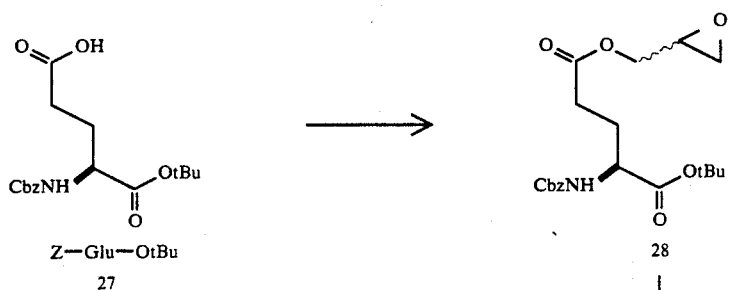

SCHEME 3 -continued

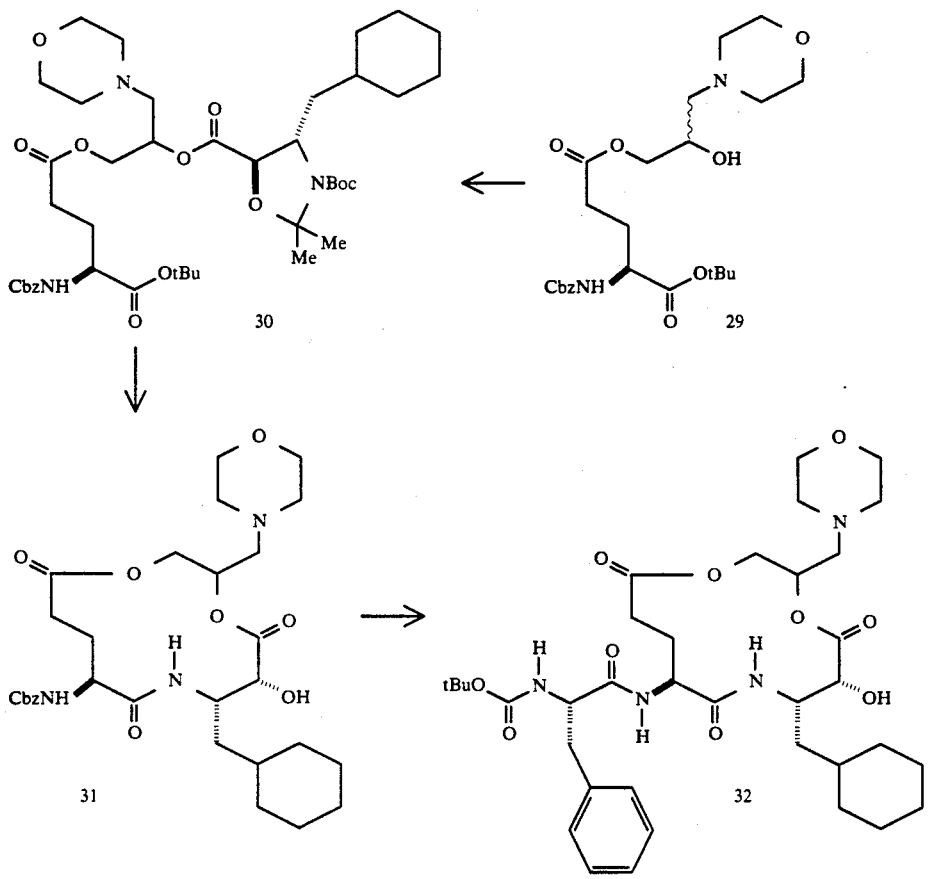

Glutamic Acid Glycidyl Ester 28.

A solution of 1720 mg (3.38 mmol) of Z-Glu-OtBu DCHA in 17 mL of dichloromethane was cooled to 0° C. and treated with 0.448 mL (6.75 mmol, 2.0 equiv) of glycidol, 41.2 mg (0.338 mmol, 0.1 equiv) of DMAP and 970 mg (5.06 mmol, 1.5 equiv) of EDC according to the general procedure for EDC/DMAP esterification. Purification by flash chromatography (30×150 mm silica gel, 35% ethyl acetate/hexane) gave 971 mg (73%) of the title compound: $^1$H NMR (300 MHz, CD$_3$OD) δ7.38–7.24 (m, 5H), 5.09 (s, 2H), 4.41 (dd, J=2.9, 12.4 Hz, 1H), 4.13–4.09 (overlapping dd, 1H), 3.91–3.84 (overlapping dd, 1H), 3.32–3.16 (m, 1H), 2.80–2.78 (overlapping t, 1H), 2.64–2.61 (overlapping dd, 1H), 2.47 (t, J=7.6 Hz, 2H), 2.20–2.08 (m, 1H), 1.97–1.84 (m, 1H), 1.45 (s, 9H); MS(FAB) 394 (M+1), 338, 294, 260.

Anal. calcd. for C$_{20}$H$_{27}$NO$_7$: C, 61.06; H, 6.92; N, 3.52. Found: C, 61.03; H, 6.89; N, 3.86.

Glutamic Acid Hydroxy Ester 29.

To a solution of 712 mg (1.81 mmol) of glycidyl ester 28 and 0.316 mL (3.62 mmol, 2.0 equiv) of morpholine was added 1 g of neutral alumina. The reaction mixture was stirred overnight and then filtered and concentrated. Purification by flash chromatography (30×150 mm silica gel, 200 mL of 1.5% and 200 mL of 2.5% methanol/dichloromethane) provided 651 mg (75%) of the title compound: $^1$H NMR (300 MHz, CD$_3$OD) δ7.38–7.29 (m, 5H), 5.09 (s, 2H), 4.19–3.97 (m, 3H), 3.69–3.60 (m, 5H), 2.56–2.41 (m, 8H), 2.22–2.08 (m, 1H), 1.97–1.84 (m, 1H), 1.45 (s, 9H); MS(FAB) 481 (M+1), 425.

Anal. calcd. for C$_{24}$H$_{36}$N$_2$O$_8$ ½H$_2$O C, 58.88; H, 7.62; N, 5.72. Found: C, 59.00; H, 7.80; N, 5.71.

Cyclization Precursor 30.

Glutamic acid hydroxy ester 29 (652 mg, 1.36 mmol, 1.0 equiv) was coupled with 556 mg (1.638 mmol, 1.2 equiv) of Boc-norACHPA acetonide (3) using 390 mg (2.03 mmol, 1.5 equiv) of EDC and 17 mg (0.136 mmol, 0.1 equiv) of DMAP in 7 mL of dichloromethane for 2 hours according to the general procedure for EDC/DMAP esterification with one modification: in the workup, the acid wash was omitted. Purification by MPLC (2 Lobar B-columns in series, 35% then 65% ethyl acetate/hexane) gave 371 mg (34%) of the title compound, 238 mg (22%) of a slower eluting diastereomer, and 168 mg (15%) of a mixture of the two. Title compound: $^1$H NMR (300 MHz, CDCl$_3$) δ7.33–7.26 (m, 5H), 5.50 (d, J=8.3 Hz, 1H), 5.30 (m, 1H), 5.07 (s, 2H), 4.45–4.20 (m, 4H), 4.04 (dd, J=7.3, 12.6 Hz, 1H), 2.53–2.29 (m, 8H), 2.19–2.09 (m, 1H), 1.95–0.85 (m, 14H), 1.63 (s, 6H), 1.44 (s, 9H), 1.42 (s, 9H); MS(FAB) 804 (M+1).

Anal. calcd. for C$_{42}$H$_{65}$N$_3$O$_{12}$ 1.15 H$_2$O: C, 60.99; H, 8.20; N, 5.08. Found: C, 60.75; H, 7.81; N, 5.41.

Macrocycle 31

Macrocyclization of 371 mg (0.461 mmol) of precursor 30 was carried out according to the general procedure (Method A) with one modification: in the workup, the acid wash was omitted. Purification by MPLC (Sephadex LH-20, methanol) gave 87.2 mg (32%) of the title compound: R$_f$ 0.44 (10% methanol/dichloromethane); $^1$H NMR (300 MHz, CDCl$_3$) δ7.34–7.26 (m, 5H), 6.55 (d, 1H), 5.50–5.42 (m, 1H), 5.11 (d, J=12.3 Hz, 1H), 5.05 (d, J=12.3 Hz, 1H), 4.54 (m, dd, J=9.3, 11.9 Hz, 1H), 4.40–4.32 (m, 1H), 4.32 (d, J=1.6 Hz, 1H), 4.24 (dd, J=4.9, 9.9 Hz, 1H), 4.01 (dd, J=1.6, 11.8 Hz, 1H), 3.75–3.67 (m, 4H), 2.74 (dd, J=8.8, 13.0 Hz, 1H), 2.60–2.39 (m, 7H), 2.10–0.85 (m, 15H); MS(FAB) 590 (M+1).

Anal. calcd. for $C_{30}H_{43}N_3O_9$: C, 61.11; H, 7.35; N, 7.13. Found: C, 60.71; H, 7.57; N, 7.00.

Macrocycle 32

A 65.5 mg (0.110 mmol) sample of 31 was deprotected according to Method D and then treated with 0.017 mL (0.122 mmol, 1.1 equiv) of triethylamine, 88.4 mg (0.333 mmol, 3.0 equiv) of BocPhe, 51.0 mg (0.333 mmol, 3.0 equiv) of HOBt, and 63.9 mg (0.333 mmol, 3.0 equiv) of EDC as described in the general procedure (Method B) with one modification: in the work-up, the acid wash was omitted. Purification by flash chromatography (20×150 mm silica gel, 150 mL of 2.5% and 200 mL of 5% methanol/dichloromethane) yielded 22.8 mg (29%) of the title compound: $^1$H NMR (300 MHz, CD$_3$OD) δ7.28–7.20 (m, 5H), 5.45 (m, 1H), 4.44–4.27 (m, 5H), 4.17 (dd, J=1.9, 11.8 Hz, 1H), 3.68 (br t, J=4.2 Hz, 4H), 3.08 (dd, J=4.8, 13.7 Hz, 1H), 2.82–2.71 (m, 2H), 2.60–2.89 (m, 7H), 2.26–1.86 (m, 3H), 1.75–0.85 (m, 12H), 1.35 (s, 9H); MS(FAB) 703 (M+1).

Anal. calcd. for $C_{36}H_{54}N_4O_{10}$ ½$H_2O$: C60.74; H, 7.79; N, 7.87. Found: C, 60.70; H, 7.80; N, 7.74.

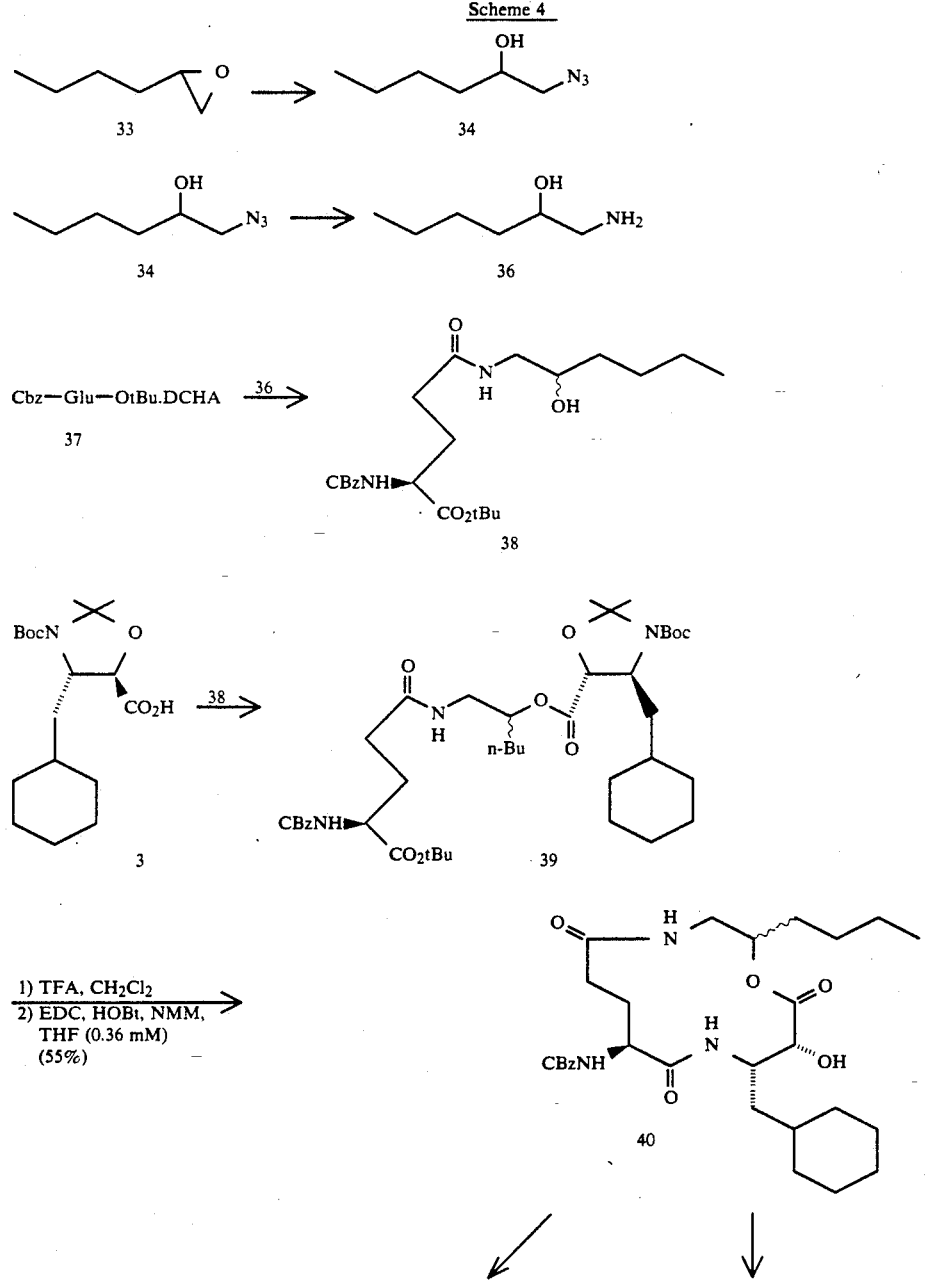

-continued
Scheme 4

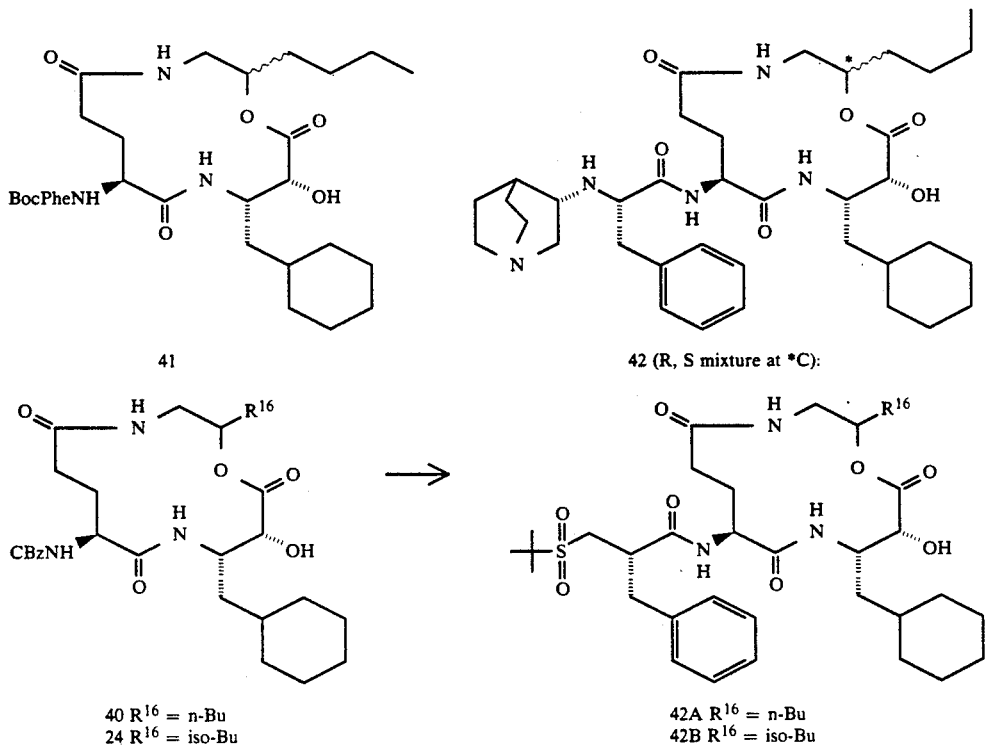

40 R$^{16}$ = n-Bu
24 R$^{16}$ = iso-Bu

42A R$^{16}$ = n-Bu
42B R$^{16}$ = iso-Bu

2-Hydroxyhexylazide 34

To a solution of 2,3-epoxyhexane 33 (4.155 g, 41.48 mmol) in N,N-dimethylformamide (DMF) was added lithium azide (3.8 g, 77.6 mmol) and the resulting mixture was stirred for 48 hours. The reaction mixture was poured into a solvent mixture of ether, dichloromethane and water, and stirred for a few minutes. The organic layer was separated from the aqueous layer and then the aqueous phase was extracted three times with ether-dichloromethane mixture. The combined organic extracts were washed with saturated aqueous solution of sodium chloride, dried over anhydrous magnesium sulfate and concentrated on rotory evaporator to give an oil. Flash column chromatography of the oil using 10% ethyl acetate in hexane as eluent afforded 34 (5.9 g, 99.3%): $^1$H NMR (300 MHz, CDCl$_3$) δ3.775 (m, 1H, CHOH), 3.38 (dd, 1H, CHN$_3$), 3.25 (dd, 1H, CHN$_3$), 2.2 (d, 1H, OH), 1.6–1.2 (m, 6H, CH$_2$'s), 0.95 (t, 3H, CH$_3$).

2-Hydroxyhexylamine 36

A mixture of 34 (3.2 g, 22.35 mmol) and palladium hydroxide (0.6 g, 4.27 mmol) in methanol was shaken under 40 psi pressure of hydrogen for 16 hours. The reaction mixture was filtered through Celite and the filter cake was washed with methanol and dichloromethane. The filtrate was concentrated to produce 36 as an oil (2.48 g, 95%): $^1$H NMR (300 MHz, CD$_3$OD) δ3.5 (m, 1H, CHOH), 2.65 (dd, $^1$H, CHNH$_2$), 2.5 (dd, 1H, CHNH$_2$), 1.525–1.25 (m,6H, CH$_2$'s), 0.93 (t, 3H, CH$_3$).

Preparation of Amide 38

Z-Glu-OtBu•DCHA 37 (12 g, 23.166 mmol) was suspended in DMF-THF-dichloromethane and hydroxylamine 36 (4 g, 34 mmol) was added to afford a clear solution. To this clear solution was added 1-(3-dimethylaminopropyl)-3-ethyl-carbodiimide hydrochloride (EDC, 8.89 g, 46.37 mmol) and 1-Hydroxybenzotriazole hydrate (HOBT, 7.1 g, 46.36 mmol). The resulting white suspension was stirred overnight and the mixture was then poured into ethyl acetate-ether-dichloromethane mixture. It was sequentially washed with 1N HCl, saturated aqueous solutions of sodium bicarbonate and sodium chloride. The organic phase was dried over anhydrous magnesium sulfate, filtered and concentrated to give a syrup. Purification of the syrup by flash column chromatography (30% hexane in ethyl acetate) gave 7.6 g (75%) of 38 as a syrup: $^1$H NMR (300 MHz, CDCl$_3$) δ7.35 (m, 5H), 6.525–6.33 (m, 1H), 5.675 (m, 1H), 5.1 (ABq, 2H, PhCH$_2$OCO), 4.225 (m, 1H), 3.8–3.5 (m, 2H), 3.45–3.05 (m, 2H), 2.35–2.1 (m,2H), 2.05–1.6 (m, 2H),1.45 (s, 9H, tBu H's), 1.4–1.0 (m), 0.9 (t, 3H, CH$_3$); MS(FAB) 437 (M+1), 381, 337.

Cyclization Precursor 39

Boc-nor-ACHPA acetonide 3 (6.57 g, 19.267 mmol, 1.2 equiv) was coupled with the amide 38 (7.0 g, 16.055 mmol) using EDC (4.62 g, 24.17 mmol, 1.5 equiv) and DMAP (0.196 g, 1.6 mmol, 0.1 equiv) in 75 mL of dichloromethane overnight according to the general procedure. Purification of the crude product by flash column chromatography (using 50% ethyl acetate in hexane as eluent) gave the diastereomeric mixture 39 (9.52 g, 78%) as an oil: R$_f$ 0.557 (50% ethyl acetate in hexane); $^1$H NMR (300 MHz, CDCl$_3$) δ7.4 (m,5H), 6.4 (m, 1H), 6.25 (m, 1H), 5.6 (d, 1H), 5.1 (s, 2H, PhCH$_2$) 5.05–4.9 (m, 1H), 4.375 (d, 1H) 4.325–4.1 (m, 2H), 3.65–3.475 (m, 1H), 3.425–3.2 (m, 1H), 2.3–2.1 (m, 3H), 1.9 (d, 1H), 1.8–1.58 (m), 1.66 (s, 3H), 1.6 (s, 3H), 1.55 (d), 1.47 (s, 18H), 1.4–1.1 (m), 1.1–0.93 (m); MS (FAB) 760 (M+1), 660, 604.

Macrocycle 40

Macrocyclization of diastereomeric mixture 39 (0.4074 g,0.5367 mmol) according to the general procedure (method A), after flash column chromatography (4% methanol in dichloromethane), afforded 40 (0.1589 g, 54%) as a white solid: $R_f$ 0.44 (100% ethyl acetate), $R_f$ 0.2 (2% methanol in dichloromethane); $^1$H NMR (300 MHz, CDCl$_3$) δ7.425-7.2 (m, 5H), 6.95 (d, 1H), 6.57 (t, 1H), 6.45 (d, 1H), 5.89 (d, 1H), 5.79 (d, 1H), 5.425-5.3 (m, 1H), 5.1 (ABq, 2H, PhCH$_2$), 4.525-4.38 (m, 2H), 4.38-4.28 (m, 1H), 4.25 (br s, 1H), 4.225 (br s), 3.98-3.75 (m), 3.55 (dd, 1H), 3.45 (br s), 3.0-2.8 (m,2H), 2.53-2.3 (m), 2.25-2.05 (m), 1.95-1.8 (m), 1.8-1.575 (m), 1.575-1.4 (m), 1.4-1.05 (m), 1.05-0.8 (br t); MS (FAB) 546 (M+1).

Anal. calculated for C$_{29}$H$_{43}$N$_3$O$_7$: C, 63.8532; H, 7.88, N, 7.70. Found: C, 63.71; H, 8.16; N, 7.58.

Macrocycle 41

Compound 40 (29.2 mg, 0.0535 mmol) was treated overnight with 2 mL of 4:1 mixture of trifluoroacetic acid: dimethyl sulfide. The volatiles were removed in vacuo, the resulting residue was coevaporated several times with toluene and dried over P$_2$O$_5$/KOH under vacuum for several hours. The deprotected material was then dissolved in 1.5 mL of dichloromethane and 0.5 mL of DMF and treated with NMM (12 μL, 0.107 mmol, 2 equiv), Boc-Phe (42.6 mg, 0.1605 mmol, 3.0 equiv), EDC (30.8 mg, 0.1606 mmol, 3 equiv), HOBt (24.6 mg, 0.1606 mmol, 3 equiv) and processed according to method A. Purification by flash column chromatography (using 5% methanol in dichloromethane) gave the title compound as a white solid (25 mg, 71%): $R_f$ 0.4 (5% methanol in dichloromethane); 1H NMR (300 MHz, CDCl$_3$) δ7.45-7.15 (m, 5H), 6.83 (d, 1H), 6.57 (d, 1H), 6.33 (br t, 1H), 5.98 (d, 1H), 5.4-5.25 (m, 1H), 5.125-4.9 (m, 1H), 4.6-4.13 (m, 3H), 4.05-3.925 (m, 1H), 3.85-3.675 (m), 3.53-3.37 (m, 1H), 3.15-2.85 (m, 2H), 2.4-1.93 (m, 3H), 1.93-1.45 (m), 1.45-1.05 (m), 1.43 (s, 9H, t-Bu H's, isomer 1), 1.398 (s, 9H, tBu H's, isomer 2), 1.025-0.775 (m, 3H); MS (FAB) 659 (M+1), 603, 559.

Macrocycle 42

A solution of 40 (33.7 mg, 0.0618 mmol) in methanol and ethyl acetate (1:1 mixture) was stirred with 10% palladium on carbon under an atmosphere of hydrogen overnight. The mixture was then filtered through Celite and concentrated. The residual syrup was dried by co-evaporating several times with toluene and then over P$_2$O$_5$/KOH under vacuum for several hours. The cyclic amine was then treated with triethyl amine (10 μL, 0.0741 mmol, 1.2 equiv), N-[quinuclidin-3(S)-yl]-phenylalanine dihydrochoride (25.73 mg, 0.074 mmol), dicyclohexylcarbodiimide (15.3 mg, 0.0741 mmol) and HOBt (5 mg, 0.0326 mmol, 0.5 equiv) in 2 mL of dichloromethane overnight. The reaction mixture was concentrated and flash column chromatography (20×150 mm silica gel, 85:15:1 dichloromethane:methanol:ammonium hydroxide) of the residue afforded 42 (25 mg, 61%) as a white solid: $^1$H NMR (300 MHz, CD$_3$OD/CDCl$_3$) δ7.33-7.08 (m, 5H), 4.95 (m, 1H), 4.43 (dd, 1H), 3.68 (dd, 1H), 3.63-3.475 (m, 2H), 3.43-3.28 (m, 2H), 3.27-3.16 (m), 3.16-3.05 (m, 1H), 2.98 (dd, 1H), 2.78-2.38 (m,), 2.32-2.78 (m, 1H),2.155-2.05 (m, 1H), 2.05-1.88 (m, 1H), 1.88-1.46 (m, 6H), 1.45-0.98 (m, 15H), 1.38-0.72 (m); MS (FAB) 668 (M+1).

Preparation of Macrocycle 42A

A solution of 60 mg (0.11 mmol) of diastereomer 1 of 40 (diast 1 is the faster moving isomer of R and S mixture at P$_2'$ position of 40) was stirred overnight with 10% Pd on Carbon. The mixture was filtered through Celite and concentrated. The residue was dried by co-evaporating several times with toluene and then over P$_2$O$_5$/KOH in vacuo overnight. The deprotected macrocycle was then treated with NMM (24 μL, 2 equiv), EDC (42 mg, 22 mmol, 2 equiv), HBT (34 mg, 22 mmol, 2 equiv) and 2-(R)-t-butylsulfonylmethyl-3-phenylpropionic acid (40 mg, 1.28 equiv) in dichloromethane and THF at 0° C. for few a hours. The mixture was stirred overnight at room temperature, then concentrated and flash chromatographed (silica gel, 2%-5% methanol in dichloromethane) to give 42A (30 mg, 40%). $^1$H NMR (300 MHz, CDCl$_3$) δ7.35-7.15 (m, 5H), 6.76 (d, J=6.19 Hz, 1H), 6.11 (dd, J=0.027 Ha, 0.015 Hz, 1H), 6.02 (d, J=8.68 Hz, 1H), 4.89-4.85 (m, 1H), 4.4-4.32 (m, 2H), 4.17 (s, 1H), 3.9-3.8 (m, 1H), 3.75-3.63 (m, 2H), 3.51 (dd, J=13.13 Hz, 9.39 Hz, 1H), 3.23-2.97 (m, 2H), 2.95-2.775 (m, 2H), 2.7-2.45 (m, 1H), 2.26 (s, 3H), 2.05 (dd, J=5.7 Hz, 1H), 1.9-1.55 (m,), 1.55-1.42 (m,), 1.41-1.05 (m), 1.317 (s, 9H), 1.05-0.8 (m); MS (FAB) 678 (M+1).

Preparation of Macrocycle 42B

N-Cbz macrocycle 24 (81.2 mg, 0.149 mmol) was stirred with 10% palladium on carbon (50 mg) in THF-EtOAc-MeOH (80 mL of THF containing 10 ml each of EtOAc and MeOH) under hydrogen overnight and the mixture was filtered through Celite. The solution was concentrated and dried by coevaporating the material several times with toluene. The resulting deprotected material was then dried over P$_2$O$_5$/KOH in vacuo overnight. The dried macrocycle was treated with NMM (33 μL, 2 equiv), EDC (57 mg, 2 equiv), HBT (45.6 mg, 2 equiv) and 2-(S)-t-butylsulfonylmethyl-3-phenylpropionic acid (63 mg, 1.5 equiv) in dichloromethane and THF at 0° C. with gradual warming to room temperature for 24 hours. The reaction mixture was concentrated and subjected directly to flash column chromatography (2%-5% MeOH in dichloromethane) to afford the inhibitor 42B (37 mg, 37%) as a white solid: $^1$H NMR (300 MHz, CDCl$_3$) δ7.31-7.15 (m, 5H), 6.82 (d, J=6.35 Hz, 1H), 6.2835 (d, J=8.68 Hz, 1H), 6.1585 (dd, J=8.3 Hz, 3.69 Hz, 1H), 5.028 (m, 1H), 4.437-4.381 (m, 2H), 4.206 (s, 1H), 3.9-3.76 (m, 1H), 3.65 (br s), 3.513 (dd, J=13.29 Hz, 9.66), 3.22-3.1 (m, 1H), 3.1-3.0 (m, 1H), 2.9 (dd, J=13.24 Hz, 2.33 Hz), 2.82 (dd, J=13.41 Hz, 7.82 Hz, 1H), 2.35-2.1 (m, 4H), 1.82-1.55 (m, 4H), 1.4875 (dd, J=14.65 Hz, 6.95 Hz, 2H), 1.4-1.075 (m, 14H), 1.317 (s, 9H), 0.941-0.92 (overlapping d, 6H); MS (FAB) 678 (M+1).

SECTION C: PREPARATION OF MACROCYCLIC RENIN INHIBITORS OF FORMULA I where D=—CONH—, W=—NH—, Z=—OH, and Y=—CH$_2$CH(OH)—

Schemes 5 and 6 illustrate the preparation of macrocyclic diol renin inhibitors of Formula I in which D=—CONH—, W=—NH—, Z=—OH, and Y=—CH$_2$CH(OH)—. Removal of the amino-terminal Boc protecting group from macrocycle 53 (see below), followed by coupling of the resulting amino-derivative with an acylating agent such as a carboxylic acid component (for example, Boc-Phe), and acid chloride or a sulfonyl chloride (Method D or E), provides inhibitors such as 54. In Scheme 6, an additional substituent, representing R[16] in Formula I is introduced into intermediate 62. Possible routes to macrocyclic diols incorporating other such substitutent include, for example, treatment of amide 57 with substituted vinyl lithium reagents, alkylation of intermediate 59 (or a ketal analog of 59), or alkylation of a ketal analog which incorporates the diol moiety of intermediate 61. As will be obvious to those skilled in the art, functional groups present in the R$_{16}$ substituent may require protection during the following steps of the synthesis. In these cases, protecting groups are chosen so as to be compatible with the Boc, Cbz, and t-butyl ester protecting groups used for other amine and carboxylic acid groups as described in the general synthetic route above. Examples are the t-butyldimethylsilyl group for alcohols, the trichloroethoxycarbonyl group for amines and trimethylsilylethyl ester for carboxylic acids.

SCHEME 5

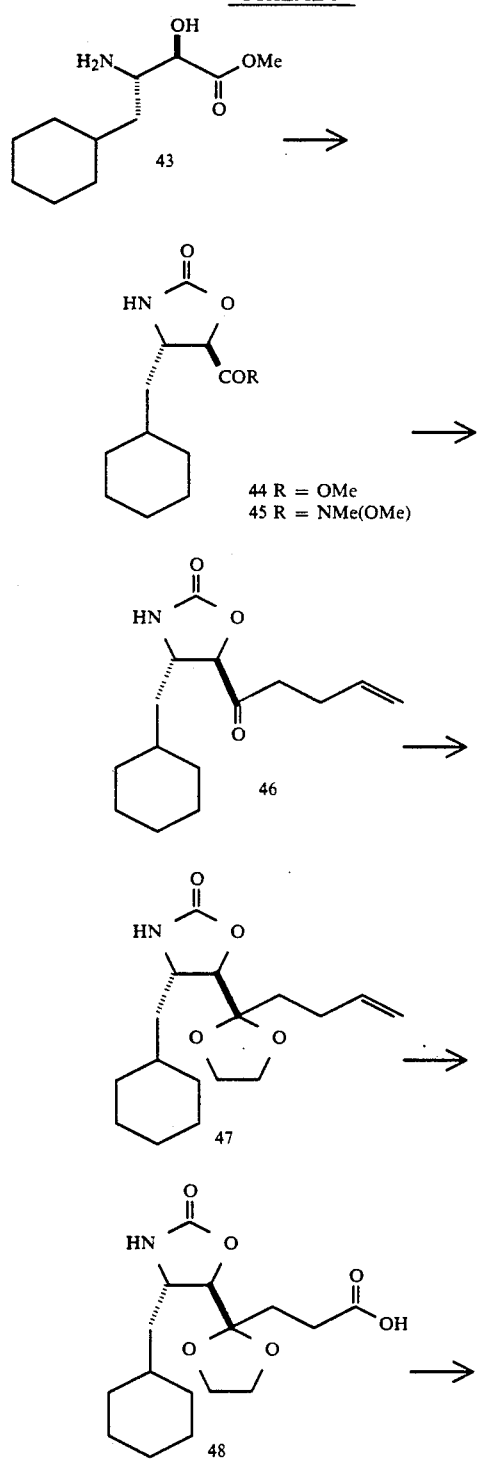

-continued
SCHEME 5

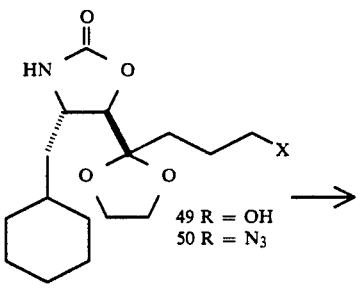

49 R = OH
50 R = N₃

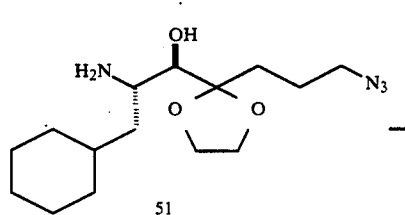

51

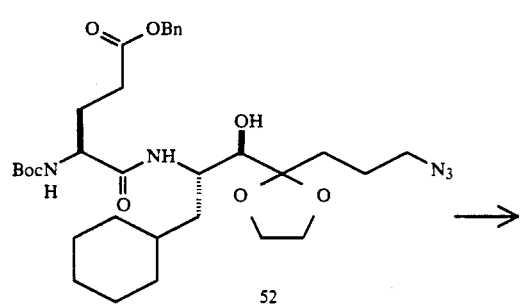

52

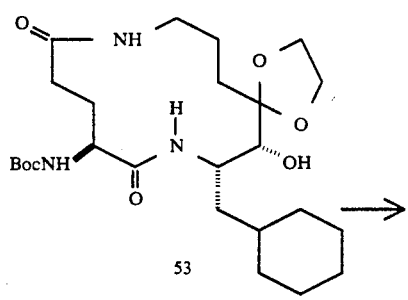

53

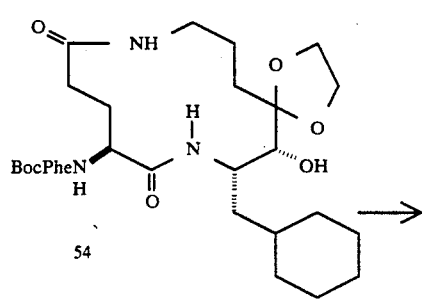

54

-continued
SCHEME 5

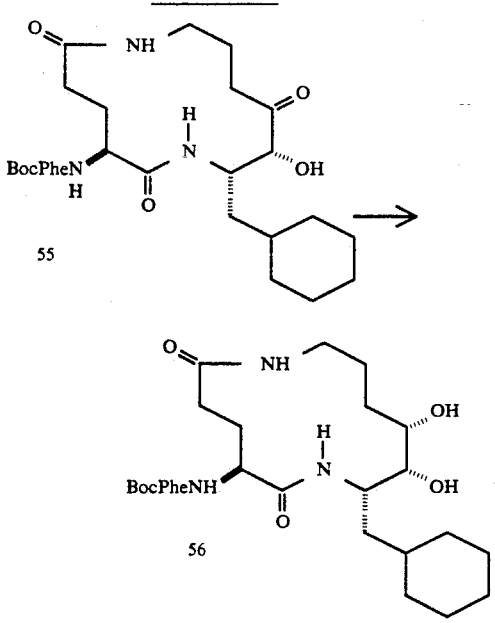

Oxazolidinone Ester 44

To a solution of 2.58 g (12.0 mmol) of amino ester 43 (Hoover, D. J., U.S. Pat. No. 4,668,769 (1987)) in 60 mL of toluene at 0° C. was added 2.67 g (3.67 mL, 26.4 mmol, 2.2 equiv) of triethylamine followed by 6.21 mL (12.0 mmol, 1.0 equiv) of phosgene solution (1.93M in toluene) dropwise over 10 minutes. The reaction was stirred an addition 30 minutes, then diluted with ethyl acetate, washed with 2 portions of 1N aqueous sodium bisulfate solution, dried over anhydrous magnesium sulfate and concentrated. Purification by MPLC (Lobar C column, 40% ethyl acetate/hexane) provided 2.17 g (75%) of the title compound: $R_f$ 0.48 (50% ethyl acetate/hexane); MS(FAB) 242 (M+1).

Anal. calcd. for $C_{12}H_{19}NO_4$: C, 59.73; H, 7.94; N, 5.80. Found: C, 59.97; H, 8.18; N, 5.94.

Oxazolidinone Amide 45

To a solution of 2.84 g (11.8 mmol) of ester 44 in toluene at 0° C. was added 38.7 mL (25.9 mL) of a 0.67M solution of Weinreb's reagent in toluene (Levin, J. I.; Turos, E.; Weinreb, S. M. Synthetic Comm. 1982, 12, 989–993). The reaction was quenched after 1.5 hour by the addition of 1N aqueous hydrochloric acid. Ethyl acetate was added and the layers separated. The aqueous phase was extracted several times with dichloromethane. The combined organic phases were dried over anhydrous magnesium sulfate and concentrated. Purification by MPLC (Lobar C column, 75% ethyl acetate/hexane) gave 2.56 g (80%) of the title compound: $R_f$ 0.33 (75% ethyl acetate/hexane); MS(FAB) 271 (M+1).

Anal. calcd. for $C_{13}H_{22}N_2O_4$: C, 57.76; H, 8.20; N, 10.36. Found: C, 57.84; H, 8.28; N, 10.66.

Ketone 46

To a solution of 2.56 g (9.48 mmol) of amide 45 in 50 mL of anhydrous THF was added a 0° C. solution of 4-butenylmagnesium bromide formed from 6.40 g (4.81 mL, 47.4 mmol, 5.0 equiv) of 4-butenyl bromide and 1.15 g (47.4 mmol, 5.0 equiv) of magnesium turnings in 50 mL of THF. The reaction mixture was stirred at 0° C. for 1 hour and then quenched by the addition of saturated aqueous ammonium chloride solution. Volatiles were removed in vacuo and the resultant residue was partitioned between dichloromethane and 1N aqueous hydrochloric acid. The aqueous phase was extracted twice with dichloromethane. The combined organic phases were dried over anhydrous magnesium sulfate and concentrated. Purification by MPLC (Lobar C column, 30% ethyl acetate/hexane) gave 2.07 g (82%) of the title compound: $R_f$ 0.31 (30% ethyl acetate/hexane); MS(FAB) 420 (M+1+dithiothreitol matrix).

Anal. calcd. for $C_{15}H_{23}NO_3$ C, 67.90; H, 8.74; N, 5.28. Found: C, 68.04; H, 8.93; N, 5.24.

Ketal 47

A two-phase solution of 2.07 g (7.79 mmol) of ketone 46 and 74 mg (0.39 mmol, 0.05 equiv) of tosic acid monohydrate in 78 mL of toluene and 17 mL of ethylene glycol was heated at reflux with removal of water using a Dean-Stark trap. After 24 hours, the mixture was cooled, diluted with 300 mL of ethyl acetate, washed with 150-mL portions of saturated aqueous sodium bicarbonate and saturated aqueous sodium chloride solutions, dried over anhydrous magnesium sulfate and concentrated. Purification by MPLC (Lobar C column, 40% ethyl acetate/hexane) gave 2.28 g (95%) of the title compound as an oil which crystallized: $R_f$ 0.14 (30% ethyl acetate/hexane); MS(FAB) 464 (M+1+dithiothreitol matrix).

Anal. calcd. for $C_{17}H_{27}NO_4$: C, 65.99; H, 8.80; N, 4.53. Found: C, 66.18; H, 8.79; N, 4.61.

Carboxylic Acid 48

To a solution of 1.17 g (3.77 mmol) of ketal 47 in 150 mL of acetone was added a solution of 6.03 g (28.2 mmol, 7.5 equiv) of sodium periodate and 150 mg of 51% ruthenium dioxide on carbon in 150 mL of water in three equal portions 1-2 hour apart. After the last addition, the mixture was stirred an additional 30 minutes, then quenched with isopropanol, filtered through Celite, and concentrated. The residue was partitioned between dichloromethane and 1:1N aqueous sodium bisulfite/1N aqueous sodium bisulfate. The aqueous phase was washed with dichloromethane and the combined organic phases were dried over anhydrous magnesium sulfate and concentrated to give 1.21 g (98%) of a foam: $R_f$ 0.15 (7.5% methanol/dichloromethane); $^1$H NMR (300 MHz, CDCl$_3$) δ12 (br s, 1H), 6.65 (s, 1H), 4.15–4.00 (m, 5H), 3.81 (pent, J=4.5 Hz, 1H), 2.49–2.37 (m, 2H), 2.13–1.92 (m, 2H), 1.76–1.68 (m, 5H), 1.60–1.22 (m, 6H), 1.00–0.85 (m, 1H).

Alcohol 49

To a solution of 1.20 g (3.67 mmol) of acid 48 in 18 mL of THF at 0° C. was added 4.58 mL (9.16 mmol, 2.5 equiv) of borane methyl sulfide (2.0M in THF). The reaction mixture was stirred at room temperature for 3 hours, then quenched with methanol and concentrated. The residue was dissolved in ethyl acetate, washed with saturated aqueous sodium bicarbonate, dried over anhydrous magnesium sulfate and concentrated. Purification by flash chromatography (30×150 mm silica gel, 100% ethyl acetate) gave 1.09 g (95%) of the title compound as a clear oil: $R_f$ 0.39 (7.5% methanol/dichloromethane); MS(FAB) 314 (M+1), 252.

Anal. calcd. for $C_{16}H_{27}NO_5 \cdot \frac{1}{2}H_2O$ C, 60.45; H, 8.72; N, 4.41. Found: C, 60.58; H, 8.94; N, 4.43.

Azide 50

A solution of 1.09 g (3.49 mmol) of alcohol 49, 424 mg (0.58 mL, 4.19 mmol, 1.2 equiv) of triethylamine, and 440 mg (0.30 mL, 3.84 mmol, 1.1 equiv) of methanesulfonyl chloride in 20 mL of dichloromethane was stirred at 0° C. for 30 minutes. The reaction mixture was then diluted with 100 mL of dichloromethane, washed with 50-mL portions of 1N aqueous sodium bisulfate and saturated aqueous sodium bicarbonate, dried over anhydrous sodium sulfate and concentrated to give a white crystalline solid. This material was dissolved in 5 mL of DMF and stirred with 513 mg (10.5 mmol, 3.0 equiv) of lithium azide at room temperature overnight. The resultant solution was diluted with 50% ethyl acetate/hexane, washed with 200-mL portions of water and saturated aqueous sodium chloride, dried over anhydrous magnesium sulfate and concentrated to give 1.09 g (92%) of a white solid which was used without further purification: $R_f$ 0.44 (50% ethyl acetate/hexane); MS(FAB) 339 (M+1), 314.

Anal. calcd. for $C_{16}H_{26}N_4O_4$: C, 56.79; H, 7.74; N, 16.56. Found: C, 56.89; H, 7.79; N, 16.59.

Amine 51

A mixture of 1.09 g (3.21 mmol) of azide 50 and 2 g (6.42 mmol, 2 equiv) of barium hydroxide octahydrate in 150 mL of 3:2 dioxane/water was heated at reflux overnight. The cloudy solution was then cooled, filtered, and concentrated. The residue was dissolved in 100 mL of water and washed with 3 150-mL portions of dichloromethane. The combined organic phases were dried over anhydrous magnesium sulfate and concentrated to give 992 mg of a white solid which was used without further purification: $R_f$ 0.21 (80:5:0.5 chloroform/methanol/ammonium hydroxide).

Benzyl ester 52

To a solution of 207 mg (0.664 mmol) of amine 51 in 6 mL of dichloromethane at 0° C. was added 448 mg (1.33 mmol, 2 equiv) of Boc-Glu(OBn), 203 mg (1.33 mmol, 2 equiv) of HOBt, and 254 mg (1.33 mmol, 2 equiv) of EDC. The reaction mixture was stirred overnight with gradual warming to room temperature. The resultant solution was then diluted with 200 mL of ethyl acetate, washed sequentially with 50-mL portions of 1N aqueous sodium bisulfate, water, saturated aqueous sodium bicarbonate and saturated aqueous sodium chloride, dried over anhydrous magnesium sulfate and concentrated. Purification by flash chromatography (20×150 mm silica gel, 40% ethyl acetate/hexane) provided 363 mg (87%) of the title compound: $R_f$ 0.25 (40% ethyl acetate/hexane); MS(FAB) 632 (M+1), 606.

Anal. calcd. for $C_{32}H_{49}N_5O_8$: C, 60.84; H, 7.82; N, 11.06. Found: C, 60.81; H, 8.10; N, 11.14.

Macrocycle 53

A solution of 136 mg (0.245 mmol) of benzyl ester 52 in 4 mL of methanol was treated with 20 mg of 10% Pd/C under 40 psi of hydrogen overnight. The mixture was then filtered and concentrated. TLC analysis indicated the presence of two products so the mixture was purified by flash chromatography (20×100 mm silica gel, 100-mL portions of 10%, 30%, 100% methanol/dichloromethane) to give 48 mg of an impurity ($R_f$ 0.83 (1:1:1:1 ethyl acetate/acetic acid/water/butanol)) and 49 mg of the deprotected starting material ($R_f$ 0.54 (1:1:1:1 ethyl acetate/acetic acid/water/butanol); MS(FAB) 516 (M+1)). This material was subjected to macrocyclization according to the general procedure (method B) using 52.3 mg (0.041 mmol, 2.0 equiv) of DPPA and 11.5 mg (0.016 mL, 0.114 mmol, 1.2 equiv) of triethylamine to provide 32.5 mg (30% overall yield) of the title compound: $R_f$ 0.39 (7.5% methanol/dichloromethane); $^1$H NMR (300 MHz, CD$_3$OD) δ4.19–4.07 (m, 2H), 3.99–3.88 (m, 4H), 3.51 (br t, J=10 Hz, 1H), 3.41 (s, 1H), 2.83 (br m, 1H), 2.48–2.24 (m, 2H), 2.05–0.80 (m, 19H), 1.41 (s, 9H); MS(FAB) 498 (M+1), 398.

Anal. calcd. for $C_{25}H_{43}N_3O_7 \cdot \frac{1}{2}H_2O$ 59.27; H, 8.75; N, 8.29. Found: C, 59.60; H, 8.91; N, 8.36.

Macrocycle 54

A solution of 32.5 mg (0.0653 mmol) of macrocycle 53 in 1:1 trifluoroacetic acid/dichloromethane was stirred at room temperature for 15 minutes. The solution was concentrated and trace amounts of acid were removed azeotropically with tetrahydrofuran and toluene. The resultant oil was dried over $P_2O_5$/KOH under vacuum overnight. It was then dissolved in 1 mL of dichloromethane and treated with 0.010 mL (7.27 mg, 0.0718 mmol, 1.1 equiv) of triethylamine, 34.7 mg (0.131 mmol, 2.0 equiv) of Boc-Phe, 20.0 mg (0.131 mmol, 2.0 equiv) of HOBt, and 25.0 mg (0.131 mmol, 2.0 equiv) of EDC according to the general procedure. Purification by flash chromatography (20×150 mm silica gel, 125 mL of 2.5% and 250 mL of 5% methanol/dichloromethane) gave 30.2 mg (72%) of the title compound: $R_f$ 0.19 (5% methanol/dichloromethane); $^1$H NMR (300 MHz, CD$_3$OD/CDCl$_3$) δ7.28–7.18 (m, 5H), 4.51 (dd, J=3.8, 10.0 Hz, 1H), 4.33 (dd, J=4.5, 9.3 Hz, 1H), 4.14 (t, J=7.0 Hz, 1H), 4.04–3.88 (m, 3 HO, 4.00 (s, 1H), 3.54–3.44 (m, 1H), 3.44 (s, 1H), 3.06 (dd, J=4.9, 13.7 Hz, 1H), 2.89 (m, 1H), 2.75 (dd, J=9.7, 13.8 Hz, 1H), 2.49–2.27 (m, 2H), 2.18–2.07 (m, 1H), 1.98–0.81 (m, 18H), 1.32 (s, 9H); MS(FAB) 645 (M+1), 589, 545.

Macrocycle 55

A solution of 25.0 mg (0.0389 mmol) of 54 in 3:1 acetic acid/water was heated at 80° C. for 3 hours. It was then cooled and concentrated. The resultant ketone was then dissolved in 3:1 THF/water and treated with 12.7 mg (0.0134 mL, 0.05816 mmol, 1.5 equiv) of di-tert-butyl dicarbonate and 7.2 mg (0.0853 mmol, 2.2 equiv) of sodium bicarbonate. After the mixture was stirred at room temperature for 1 hour, it was partitioned between half saturated aqueous sodium chloride and dichloromethane. The aqueous phase was washed with several portions of dichloromethane and the combined organic phases were dried over anhydrous sodium sulfate and concentrated. Purification by flash chromatography (20×150 mm silica gel, 125 mL of 2.5%, 5%, 10% methanol/dichloromethane) gave 13.2 mg (57%) of the title compound: $R_f$ 0.26 (5% methanol/dichloromethane); $^1$H NMR (300 MHz, CD$_3$OD) δ7.30–7.17 (m, 5H), 4.45–4.29 (m, 3H), 4.12 (d, J=2.0 Hz, 1H), 3.98–3.30 (m, 1H), 3.28–3.05 (m, 2H), 2.86–2.72 (m, 3H), 2.23–2.08 (m, 3H), 1.89–0.87 (m, 16H), 1.34 (s, 9H); MS(FAB) 601 (M+1), 501.

Macrocycle 56

To a solution of 8.3 mg (0.014 mmol) 55 in methanol was added 2.6 mg (0.069 mmol, 5 equiv) of sodium borohydride. After the mixture was stirred at room temperature for 1 hour, it was quenched by the addition of several drops of ethylene glycol and concentrated. The residue was dissolved in 50 mL of ethyl acetate and washed with two 10-mL portions of 0.5N aqueous sodium hydroxide and 10 mL of saturated aqueous sodium chloride, dried over anhydrous magnesium sulfate and concentrated. Purification by flash chromatography (20×150 mm silica gel, 150 mL of 2.5%, 5%, 7.5% methanol/dichloromethane) gave 3.4 mg (41%) of the title compound: $R_f$ 0.54 (10% methanol/dichloromethane); $^1$H NMR (300 MHz, CD$_3$OD) δ7.30–7.18 (m, 5H), 4.50 (m, 1H), 4.31 (dd, J=4.9, 9.4 Hz, 1H), 4.16

(dd, J=4.1, 9.6 Hz, 1H), 3.45 (m, 1H), 3.19–3.07 (m, 2H), 2.81 (dd, J=9.7, 13.3 Hz, 1H), 2.39–2.12 (m, 4H), 1.95–0.83 (m, 19H), 1.36 (s, 9H); MS(FAB) 603 (M+1), 503.

Anal. calcd. for $C_{32}H_{50}N_4O_7 \cdot H_2O$: C, 61.91; H, 8.44; N, 9.03. Found: C, 62.31; H, 8.58; N, 8.76.

Macrocycle 56 was subsequently synthesized from (2S,3R,4S)-7-azido-2-tert-butyloxycarbonylamino-1-cyclohexylheptan-3,4-diol in order to prove the relative stereochemisty of this compound.

SCHEME 6

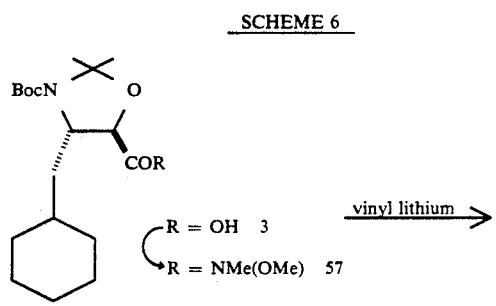
3 R = OH
57 R = NMe(OMe)
vinyl lithium →

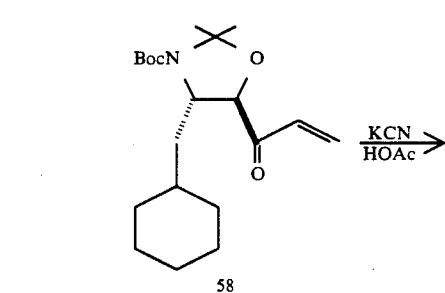
58
KCN / HOAc →

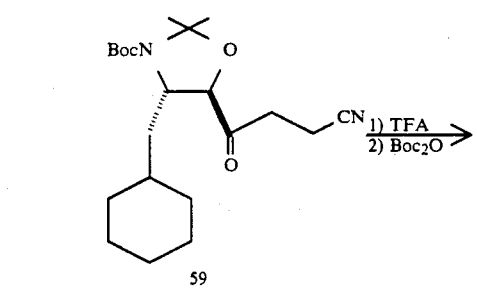
59
1) TFA
2) Boc₂O →

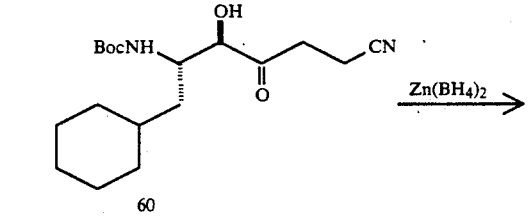
60
Zn(BH₄)₂ →

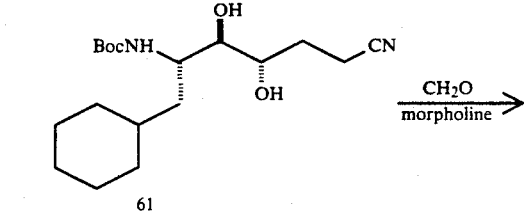
61
CH₂O / morpholine →

-continued
SCHEME 6

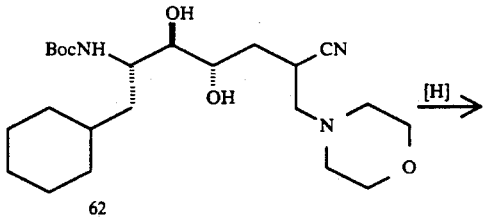
62
[H] →

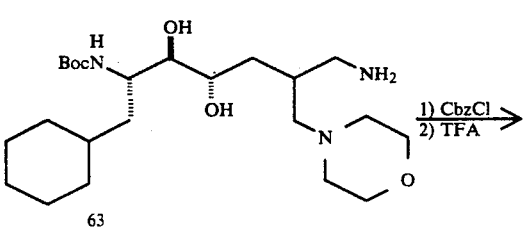
63
1) CbzCl
2) TFA →

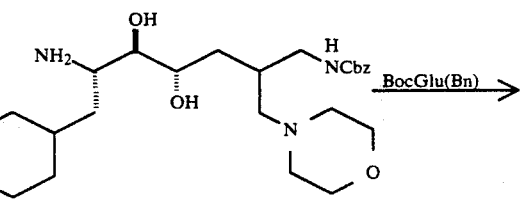
64
BocGlu(Bn) →

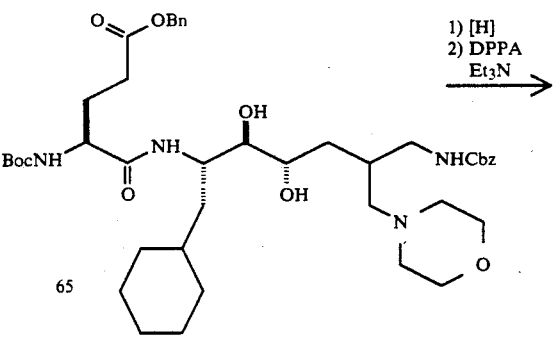
65
1) [H]
2) DPPA
Et₃N →

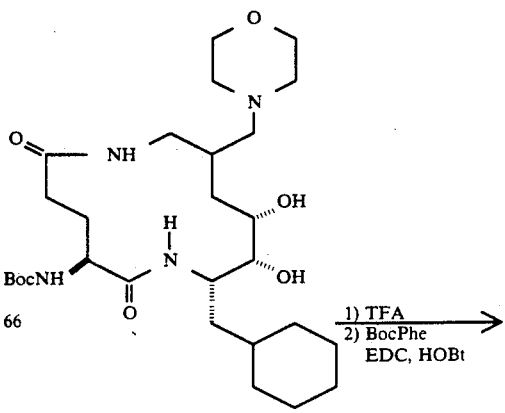
66
1) TFA
2) BocPhe
EDC, HOBt →

-continued
SCHEME 6

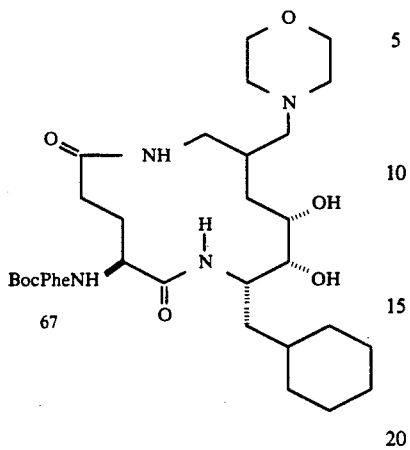

SECTION D: PREPARATION OF
MACROCYCLIC RENIN INHIBITORS OF
FORMULA I where D=—NHCO—, W=—NH—,
Z=—OH, and Y=—OCO—

Scheme 7 illustrates the preparation of macrocyclic diol renin inhibitors of Formula I in which D=—NHCO—, W=—NH—, Z=—OH and Y=—OCO—. Removal of the amino-terminal Boc protecting group from macrocycle 73 (see below), followed by coupling of the resulting amino-derivative with an acylating agent such as a carboxylic acid component (for example, Boc-Phe), an acid chloride or a sulfonyl chloride (Method D or E), provides inhibitors such as 74.

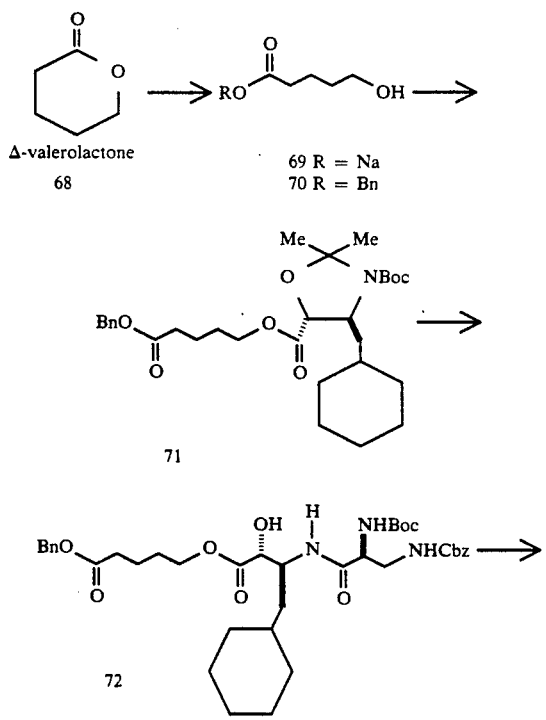

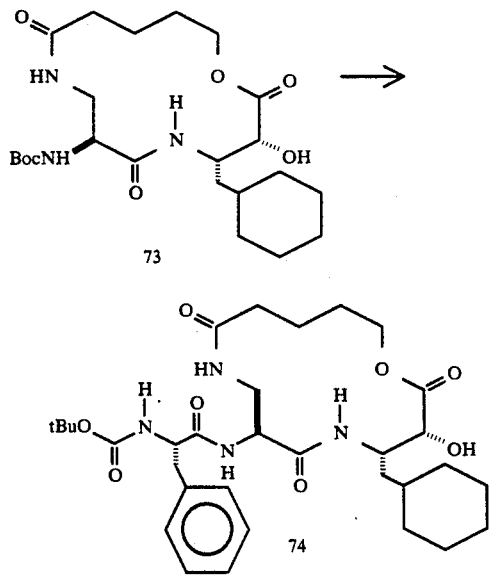

Sodium 5-Hydroxypentanoate 69

A suspension of 800 mg (8.0 mmol) of δ-valerolactone in 8 mL (8.0 mmol, 1.0 equiv) of 1N aqueous sodium hydroxide was heated at 65° C. overnight. The clear solution was cooled and concentrated. Toluene was added and the resultant slurry was concentrated to give a white solid: IR (nujol mull) 1550 cm$^{-1}$.

Benzyl 5-Hydroxypentanoate 70

To a suspension of 569 mg (4.06 mmol) of sodium 5-hydroxypentanoate 69 in 3 mL of acetone was added 1.39 g (0.97 mL, 8.11 mmol, 2.0 equiv) of benzyl bromide and 65 mg (0.203 mmol, 0.05 equiv) of tetrabutylammonium bromide. The mixture was heated at 45° C. for 24 hours, cooled, and concentrated. The residue was dissolved in 200 mL of ethyl acetate, washed with 50 mL portions of 1N aqueous sodium bisulfate, saturated aqueous sodium bicarbonate and saturated aqueous sodium chloride, dried over anhydrous magnesium sulfate and concentrated to give 1.49 g of a pale yellow oil. Purification by MPLC (Lobar C-column, 45% ethyl acetate/hexane) have 641 mg (76%) of the title compound as an oil: $^1$H NMR (300 MHz, CDCl$_3$) δ7.38-7.26 (m, 5H), 5.12 (s, 2H), 3.64 (t, 2H, J=6.3 Hz), 2.41 (t, 2H, J=7.2 Hz), 1.80-1.71 (m, 2H), 1.64-1.54 (m, 3H).

Benzyl ester 71

Boc-NorACHPA acetonide 3 (302 mg, 0.884 mmol, 1.0 equiv) was coupled with 208 mg (0.998 mmol, 1.1 equiv) of benzyl 5-hydroxypentanoate 70 using 254 mg (1.33 mmol, 1.5 equiv) of EDC and 11 mg (0.088 mmol, 0.1 equiv) of DMAP in 4 mL of dichloromethane for 4 hours according to the general procedure for EDC/DMAP esterification. Purification by MPLC (Lobar B-column, 15% ethyl acetate/hexane) gave 467 mg (99%) of the title compound as an oil: R$_f$0.25 (15% ethyl acetate/hexane); $^1$H NMR (300 MHz, CDCl$_3$) δ7.37-7.26 (m, 5H), 5.11 (s, 2H), 4.32 (s, 1H), 4.3-4.2 (br s, 1H), 4.16 (br m, 2H), 2.40 (br t, J=7.0 Hz, 2H), 1.90 (br d, J=11.3 Hz, 1H), 1.83-0.85 (m, 16H), 1.61 (s, 3H), 1.59 (s, 1.5H), 1.56 (s, 1.5H), 1.47 (s, 9H); MS(FAB) 532 (M+1), 432.

Anal. Calcd. for C$_{30}$H$_{45}$NO$_7$: C, 67.77; H, 8.53; N, 2.63. Found: C, 67.79; H, 8.78; N, 2.59.

Diaminopropionic acid derivative 72

A solution of 100 mg (0.189 mmol) of benzyl ester 71 in 2 mL of 1:1 trifluoroacetic acid/dichloromethane was stirred at 0° C. for 1 hour and room temperature for 1 hour. The solution was concentrated and trace amounts of acid were removed azeotropically with toluene. The resultant oil was dried over $P_2O_5$/KOH under vacuum for several hours and then dissolved in 1.5 mL of dichloromethane. The solution was cooled to 0° C. and treated with 80.2 mg (0.237 mmol, 1.25 equiv) of $N^\alpha$-Boc, $N^\beta$-Cbz diaminopropionic acid, 36.1 mg of HOBt (0.236 mmol, 1.25 equiv), and 45.3 mg (0.236 mmol, 1.25 equiv) of EDC. The solution was stirred overnight with gradual warming to room temperature and then diluted with 200 mL of ethyl acetate, washed sequentially with 20 mL portions of 1N aqueous sodium bisulfate solution, water, saturated aqueous sodium bicarbonate and saturated aqueous sodium chloride, dried over anhydrous magnesium sulfate and concentrated. Purification by MPLC (Lobar B column, 40% ethyl acetate/hexane) gave 105 mg (78%) of the title compound: $R_f$ 0.47 (50% ethyl acetate/hexane); 1H NMR (300 MHz, CDCl$_3$) δ7.39–7.26 (m, 10H), 6.5 (br s, 1H), 5.62 (br s, 1H), 5.48 (t, 1H), 5.13 (m, 4H), 4.38 (m, 1H), 4.20–4.06 (m, 4H), 3.51–3.45 (m, 2H), 2.38 (br t, 2H), 1.80–0.79 (m, 26H); MS(FAB) 712 (M+1), 612.

Macrocycle 73

Diaminopropionic acid derivative 72 (105 mg, 0.1468 mmol) was deprotected using 10% Pd/C under 1 atom of hydrogen in methanol overnight and cyclized according to the general procedure for Method B. Purification by flash chromatography (20×150 mm silica gel, 5% methanol/dichloromethane) gave 18.9 mg (27%) of the title compound: $R_f$ 0.67 (10% methanol/dichloromethane); $^1$H NMR (300 MHz, CD$_3$OD) δ4.32–4.05 (m, 5H), 3.55 (dd, 1H), 3.25 (dd, 1H), 2.34–2.19 (m, 2H), 1.94–0.76 (m, 26H); MS(FAB) 470 (M+1), 414,370.

Macrocycle 74

A solution of 18.9 mg (0.0402 mmol) of macrocycle 73 in 3% HCl/methanol (formed by the addition of 1 mL of acetyl chloride to 19 mL of methanol) was stirred at room temperature for 1 hours and then concentrated. The resultant deprotected macrocycle was coupled to BocPhe (21.4 mg, 0.0805 mmol, 2 equiv) using 15.4 mg (0.0805 mmol, 2 equiv) of EDC, 12.3 mg (0.0805 mmol, 2 equiv) of HOBt, and 4.48 mg (0.0062 mL, 0.0440 mmol, 1.1 equiv) of triethylamine according to the general procedure (Method D). Purification by flash chromatography (20×180 mm silica gel, 2.5% and 5% methanol/dichloromethane) gave 20.6 mg (83%) of the title compound as a white solid: $R_f$ 0.43 (5% methanol/dichloromethane); $^1$H NMR (300 MHz, CD$_3$OD) δ7.29–7.18 (m, 5H), 4.54 (dd, 1H), 4.36–4.23 (m, 4H), 4.12 (dd, 1H), 33.58 (dd, 1H), 3.37 (dd, 1H), 3.09 (dd, 1H), 2.80 (dd, 1H), 2.35–2.21 (m, 2H), 1.92–0.80 (m, 26H); MS(FAB) 617 (M+1), 517.

SECTION E: PREPARATION OF MACROCYCLIC RENIN INHIBITORS OF FORMULA I where D=—CONH—, W=—NH—, Z=—OH, and Y=—OCO—

Scheme 8 illustrates the preparation of additional macrocyclic renin inhibitors of Formula I in which D=—CONH—, W=—NH—, Z=—OH, and Y=—OCO—. Removal of the amino-terminal Boc protecting group from macrocycle 85 (see below), followed by coupling of the resulting amino-derivative with an acylating agent such as a carboxylic acid component (for example, Boc-Phe), an acid chloride or a sulfonyl chloride (Method D or E), provides inhibitors such as 86 and 87.

SCHEME 8

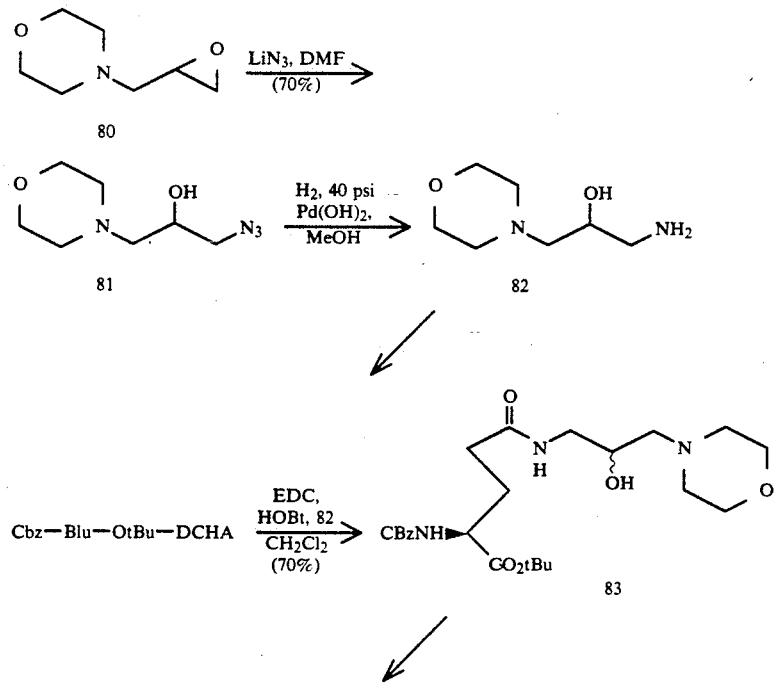

SCHEME 8
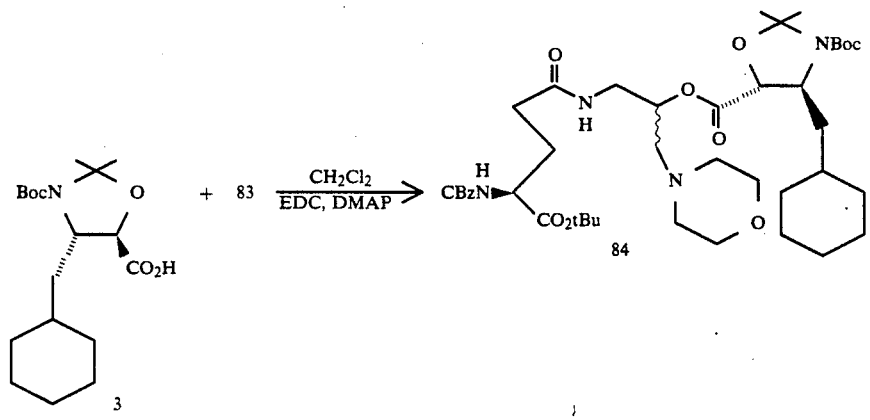
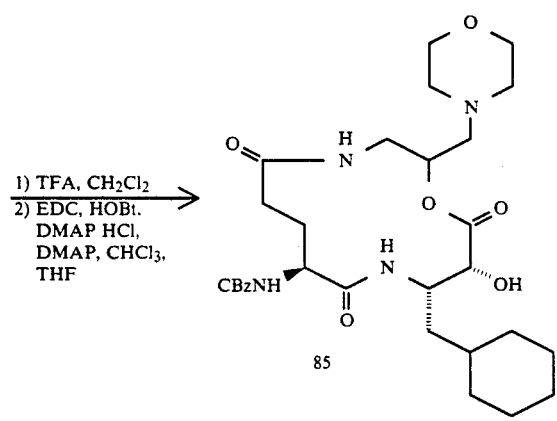
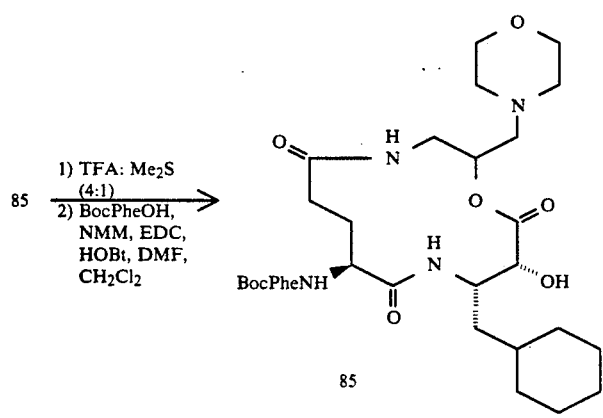

SCHEME 8 -continued

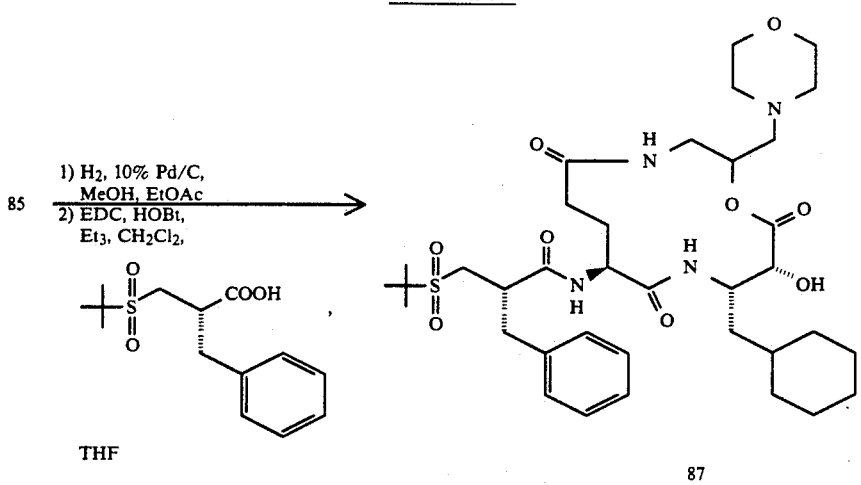

2-Hydroxy-3-morpholinylpropylazide 81

A mixture of epoxide 80 (14.3 g, 0.1 mol), and lithium azide (10 g, 0.204 mol) in DMF was stirred for 48 hours. The mixture was concentrated and then purified by flash column chromatography to afford 81 as a clear oil (13 g, 70%): $R_f$=0.39 (EtOAc); $^1$H NMR (300 MHz, CDCl$_3$) $\delta$952-3.875 (m, 1H), 3.8-3.65 (m, 4H), 3.412 (dd, J=12.75 Hz, 3.91 Hz, 1H), 3.2245 (dd, J=12.75 Hz, 5.53 Hz, 1H), 2.685-2.616 (m, 2H), 2.52-2.32 (m, 4H).

2-Hydroxy-3-morpholinylpropylamine 82

A methanolic solution of 81 (11 g, 59.14 mmol), was shaken with 20% palladium hydroxide on Carbon (2 g) under 40 psi pressure of hydrogen for 20 hours. The mixture was filtered through celite and the filter cake was thoroughly washed with methanol and dichloromethane. The solvent was removed under vacuum to give 82 (8 g, 93%) as a light yellow oil; $^1$H NMR (300 MHz, CDCl$_3$) $\delta$3.8-3.6 (m, 4H), 3.42 (m, 1H), 2.8 (br d, 1H), 2.7-2.55 (m, 2H), 2.55-2.2 (m, 6H).

Intermediate 83

To a mixture of N-Cbz-Glu-OtBu•DCHA (10 g, 19.3 mmol) and hydroxylamine 82 (4.63 g, 1.5 equiv) in dichloromethane, was added EDC (7.4 g, 2 equiv), HBT (5.92 g, 2 equiv), and triethylamine (2.7 mL, 1 equiv) and the reaction mixture stirred overnight. The mixture was poured with saturated aqueous solution of NaHCO$_3$ and NaCl. The organic phase was dried over anhydrous MgSO$_4$, filtered and concentrated to a syrup. Flash column chromatography of the syrup using 5% methanol in dichloromethane gave 83 as a diastereomeric mixture (6.5 g, 70%): $R_f$=0.52 (5% methanol in dichloromethane); $^1$H NMR (300 MHz, CDCl$_3$) $\delta$7.35-7.27 (m, 5H), 6.43-6.3 (brs, 1H), 5.7-5.55 (m, 1H), 5.1 (s, 2H), 4.3-4.15 (m, 1H), 3.9-3.75 (m, 1H), 3.75-3.6 (m, 4H), 3.6-3.4 (m, 6H), 3.25-2.95 (m, 2H), 2.675-2.525 (m, 2H), 2.5-2.1 (m), 2.05-1.75 (m), 1.75-1.55 (m), 1.459 (s, 9H), 1.35-1.125 (m); MS (FAB) 480 (M+1).

Cyclization Precursor 84

Glutamine derivative 83 (0.915 g, 1.91 mmol) was coupled with the Boc-Nor-ACHPA acetonide 3 (0.652 g, 1 equiv) using EDC (0.9 g, 2.45 equiv) and DMAP (0.3 g, 1.28 equiv) in 40 mL of dichloromethane overnight according to the general procedure. Purification of the diastereomeric mixture of 84 by MPLC (Lobar column B, 66% ethyl acetate in hexane) gave diastereomer 1 (0.42 g, 27.5%) as a white amorphous solid: $R_f$=0.195 (66% ethyl acetate in hexane); $[\alpha]_D$ −11.5° (c=0.575, CHCl$_3$); $^1$H NMR (300 MHz, CDCl$_3$) $\delta$7.37-7.27 (m, 5H), 6.6 (brs, 1H), 5.5885 (dd, J=8.08 Hz, 1H), 5.25-5.15 (m, 1H), 5.108 (s, 2H), 4.41 (br s, 1H), 4.215-4.12 (m, 1H), 3.725-3.525 (m, 4H), 3.33-3.175 (m, 1H), 2.63-2.52 (m, 2H), 2.5-2.4 (m, 2H), 2.4-2.3 (m, 2H), 2.3-2.225 (m, 2H), 2.25-2.125 (1H), 1.96-1.85 (m, 2H), 1.775-1.6 (M), 1.679 (s), 1.563 (s), 1.473 (s, 9H), 1.457 (s, 9H), 1.375-1.1 (m, 4H), 1.1-0.83 (m, 2H); MS (FAB) 803 (M+1); and diastereomer 2 (0.421 g, 27.5%) as colorless syrup: $R_f$=0.122 (66% ethyl acetate in hexane); $[\alpha]_D$ −1.1° (c=0.9, CHCl$_3$); MS (FAB) 803 (M+1).

Macrocycle 85

Macrocyclization of diastereomer 1 of 84 (0.145 g, 0.1807 mmol) was carried out according to the general procedure (Method C) described above (washings with saturated aqueous solution of sodium bicarbonate and sodium chloride were omitted in this case). Purification by flash column chromatography (20×150 mm silica gel, 250 mL of 10% and 500 mL of 16% methanol in ethyl acetate) afforded the macrocyclic renin inhibitor 85 (60 mg, 61%) as a white solid: $R_f$=0.41 (16% methanol in ethyl acetate); $^1$H NMR (300 MHz, CDCl$_3$/CD$_3$OD) $\delta$7.35 (s, 5H), 5.3-5.18 (m, 1H), 5.089 (AB$_q$, 2H), 4.0-3.83 (m, 4H), 3.8-3.55 (m, 4H), 3.36 (s, 1H), 3.05 (d, 1H), 2.75 (dd, 1H), 2.65-2.0 (m, 8H), 1.95-0.8 (m, 17H); MS (FAB) 589 (M+1).

Macrocycle 86

N-Cbz group of 85 (30 mg, 0.055 mmol) was removed and then coupled with BocPheOH (40.6 mg, 3 equiv) according to method E using NMM (7.26 μL, 1.2 equiv), EDC (29.3 mg, 3 equiv), and HBT (23.4 mg, 3 equiv) to give, after flash column chromatography (using 2%-5% methanol in dichloromethane as eluent), the cyclic inhibitor 86 (12 mg, 34%) as a white solid: $^1$H NMR (300 MHz, CDCl$_3$/CD$_3$OD) $\delta$7.43-7.17 (m, 5H), 5.2 (m, 1H), 4.52-4.42 (m, 1H), 4.42-4.28 (m, 1H), 4.25 (s, 1H), 4.2 (m), 4.0-3.6 (m), 3.42 (s), 3.38 (br s), 3.08 (dd, 1H), 2.95-2.83 (1H), 2.75 (dd, 1H), 2.65-2.38 (m), 2.38-2.25 (m), 2.225-1.96 (m), 1.95-1.58 (m), 1.58-1.46 (m), 1.45-1.075 (m), 1.2 (s, 9H), 1.07-0.8 (m); MS (FAB) 702 (M+1).

Macrocycle 87

The macrocycle 85 (49 mg, 0.0833 mmol) was stirred with 10% palladium on carbon (20 mg), in THF-EtOAc-MeOH (50 mL of THF containing 5 ml each of EtOAc and MeOH) under hydrogen overnight and the reaction mixture was filtered through Celite. The mixture was concentrated in vacuo and dried by co-evaporating with toluene several times and further dried over $P_2O_5$/KOH in vacuo for 8 hours. The dried material was treated with NMM (14 μL, 1.5 equiv), EDC (32.6 mg, 2 equiv), HBT (26 mg, 2 equiv) and 2-(R)-t-butylsulfonylmethyl-3-phenylpropionic acid (36.3 mg, 1.5 equiv) in dichloromethane and THF at 0° C. with gradual warming to room temperature for 24 hours. After removal of the solvent, the concentrated mixture was subjected directly to flash column chromatography (15% MeOH in EtOAc) to provide the inhibitor 87 (12 mg, 20%): $R_f$=0.26 (15% MeOH in EtOAc); $^1$H NMR (300 MHz, $CDCl_3/CD_3OD$) δ7.35-7.26 (m, 5H), 5.33-5.22 (m, 1H), 4.45 (br s), 4.33 (m, 1H), 4.25 (s, 1H), 3.875-3.63 (m, 4H), 3.5435 (dd, J=13.57 Hz, 9.66 Hz), 3.355 (d, 3H), 3.3-3.17 (m, 1H), 3.17-3.2 (m, 2H), 2.911 (dd, J=13.51 Hz, 3 Hz, 1H), 2.7565 (dd, J=14.65 Hz, 9.39 Hz, 2H), 2.65-2.42 (m, 4H), 2.4-2.2 (m, 2H), 2.15-1.55 (m, 4H), 1.497 (t, 2H), 1.43-1.1 (m) 1.315 (s, 9H), 1.05-0.84 (m, 2H); MS (FAB) 721 (M+1).

SECTION F: PREPARATION OF MACROCYCLIC RENIN INHIBITORS OF FORMULA I where D=—CONH—, W=—O—, Z=—OH, and Y=—OCO—

Scheme 9 illustrates the preparation of macrocyclic renin inhibitors of Formula I in which D=—CONH—, W=—O—, Z=—OH, and Y=—OCO—. Aldol condensation of protected hydroxyamide 89 with cyclohexylacetaldehyde yields adduct 90 which is esterified with N-α-Cbz-Glu(δ-O-t-Bu), yielding ester 91. Removal of the t-butyl ester of 91 by treatment with anhydrous TFA, and coupling of the resulting carboxylic acid with an optionally substituted aminoalcohol then affords the amide 92. After hydrolytic removal of the chiral auxiliary, the resulting hydroxyacid 93 is cyclized as shown the in scheme to yield macrocycle 94. Removal of the Cbz protecting group from 94 and coupling of the resulting amino intermediate with Boc-Phe yields macrocycle 95. Use of other acylating agents in place of Boc-Phe yields other inhibitors similar to 95.

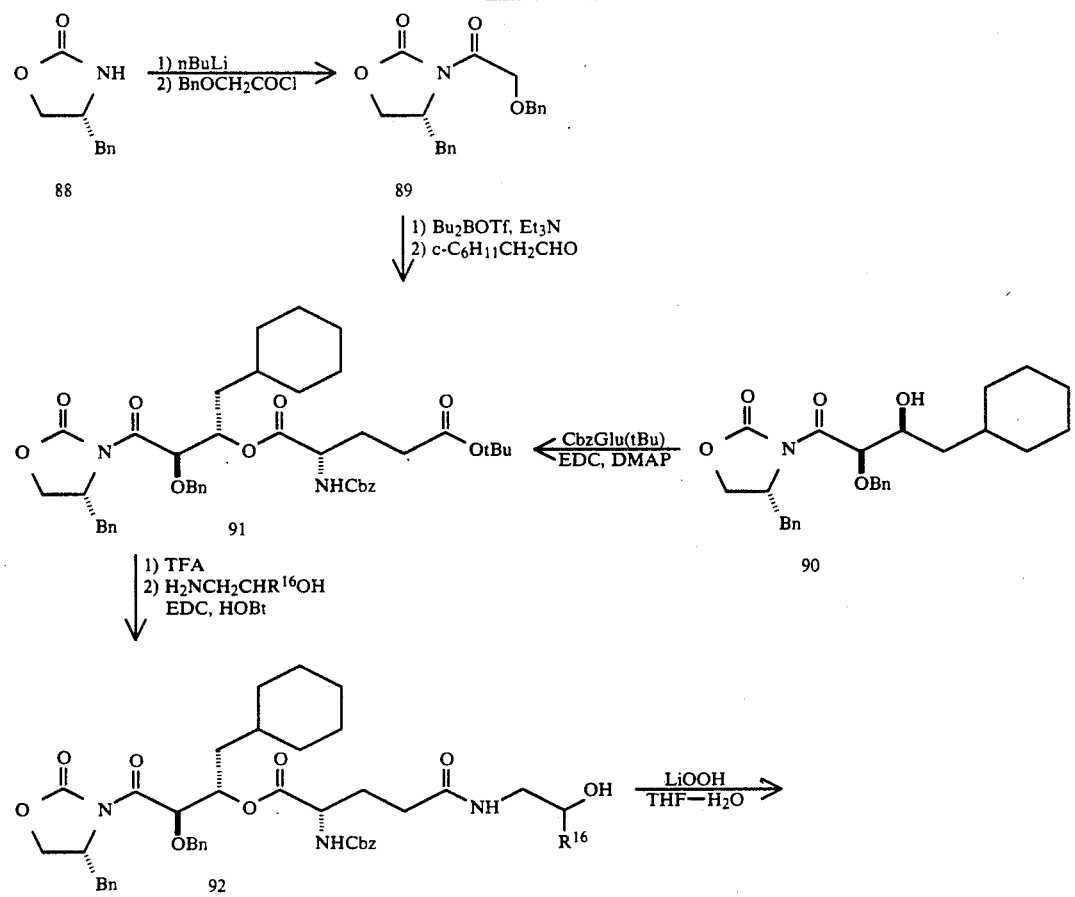

SCHEME 9

-continued
SCHEME 9

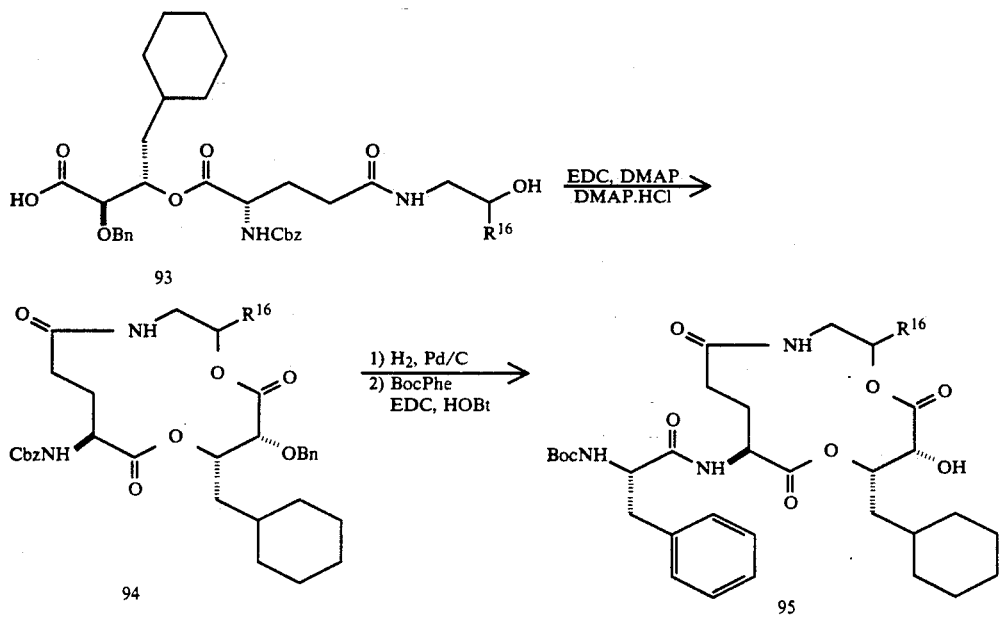

SECTION G: PREPARATION OF MACROCYCLIC RENIN INHIBITORS OF FORMULA I where D=—COO—, W=—O—, Z=—OH, and Y=—OCO—

Scheme 10 illustrates the preparation of macrocyclic renin inhibitors of Formula I in which D=—COO—, W=—O—, Z=—OH, and Y=—OCO—. Removal of the t-butyl ester of 91 by treatment with anhydrous TFA, and coupling of the resulting carboxylic acid with an optionally substituted diol yields amide 96. After hydrolytic removal of the chiral auxiliary, the resulting hydroxyacid 97 is cyclized as shown the in scheme to yield macrocycle 98. Removal of the Cbz protecting group from 98 and coupling of the resulting amino intermediate with Boc-Phe yields macrocyclic inhibitor 99. Use of other acylating agents in place of Boc-Phe yields other inhibitors similar to 99.

SCHEME 10

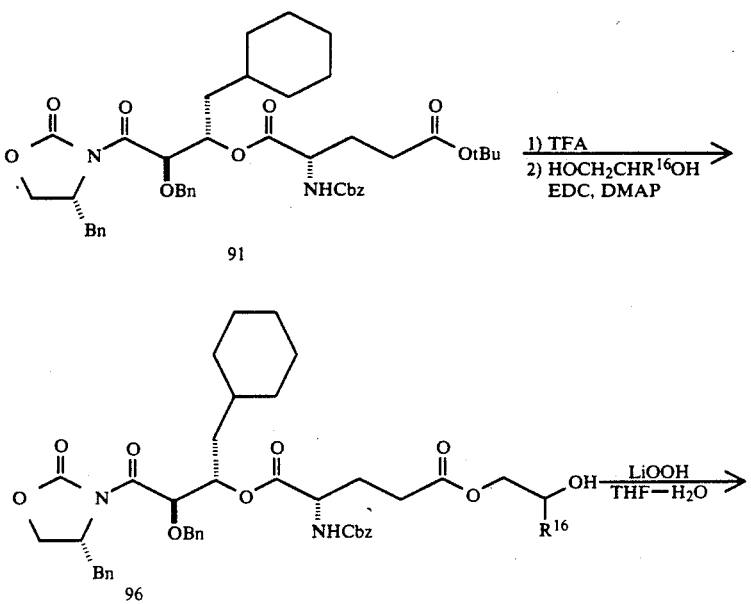

SCHEME 10

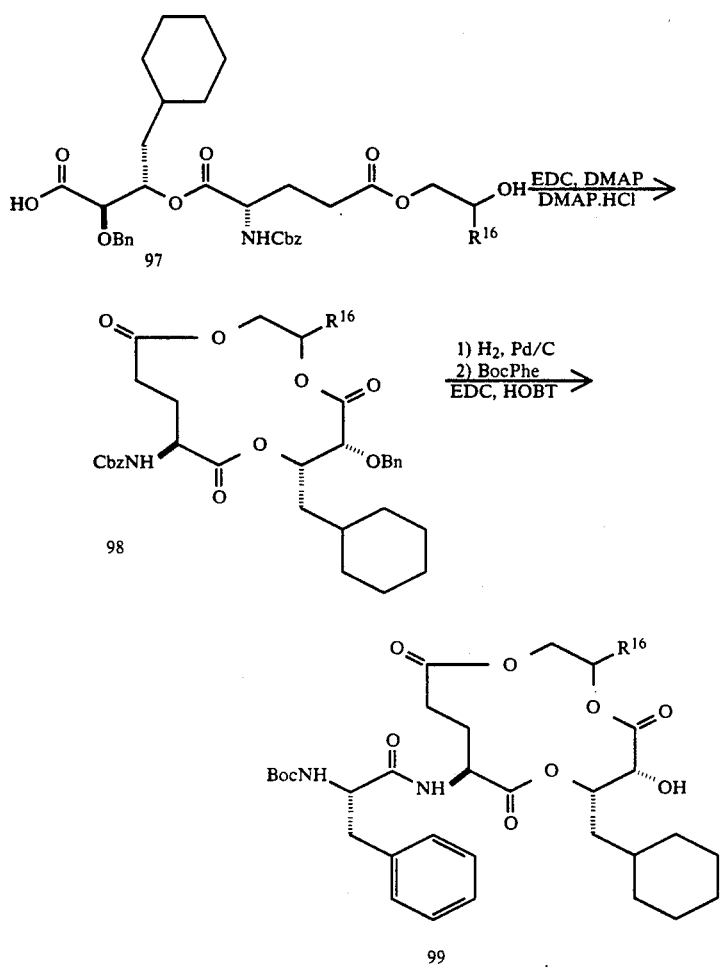

SECTION H: PREPARATION OF MACROCYCLIC RENIN INHIBITORS OF FORMULA I where D=—CONH—, W=—NH—, Z=—OH, Y=—OCO—, and $R^{15}$=methyl Scheme 11 illustrates the preparation of macrocyclic renin inhibitors of the Formula I where D= —CONH—, W=—NH—, Z=—OH, Y=—OCO—, and $R^{15}$=methyl. As shown in the scheme, glutamic acid derivative 105 is prepared by asymmetric azidation of imide 102 followed by protecting group manipulation. Imide 102 is prepared in a straight forward manner from glutaric anhydride 100. Conversion of glutamic acid derivative 105 to macrocycle 108 is carried out in the usual manner. The Cbz protecting group is removed and the resulting amine is acylated with a carboxylic acid to give inhibitors such as 109, or with an acid chloride or a sulfonyl chloride using standard procedures. Macrocyclic inhibitors with $R^{15}$=alkyl other than methyl are available from the appropriately substituted glutaric anhydride.

SCHEME 11

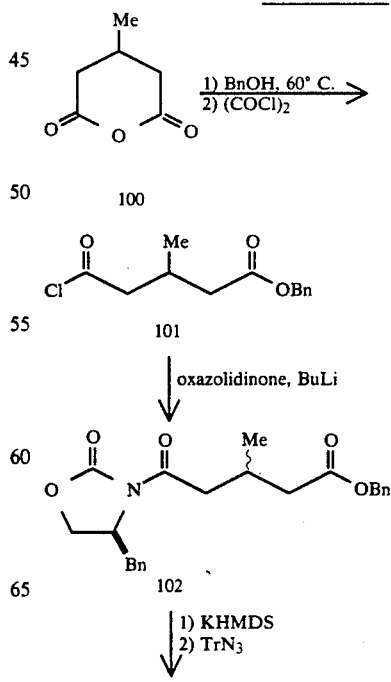

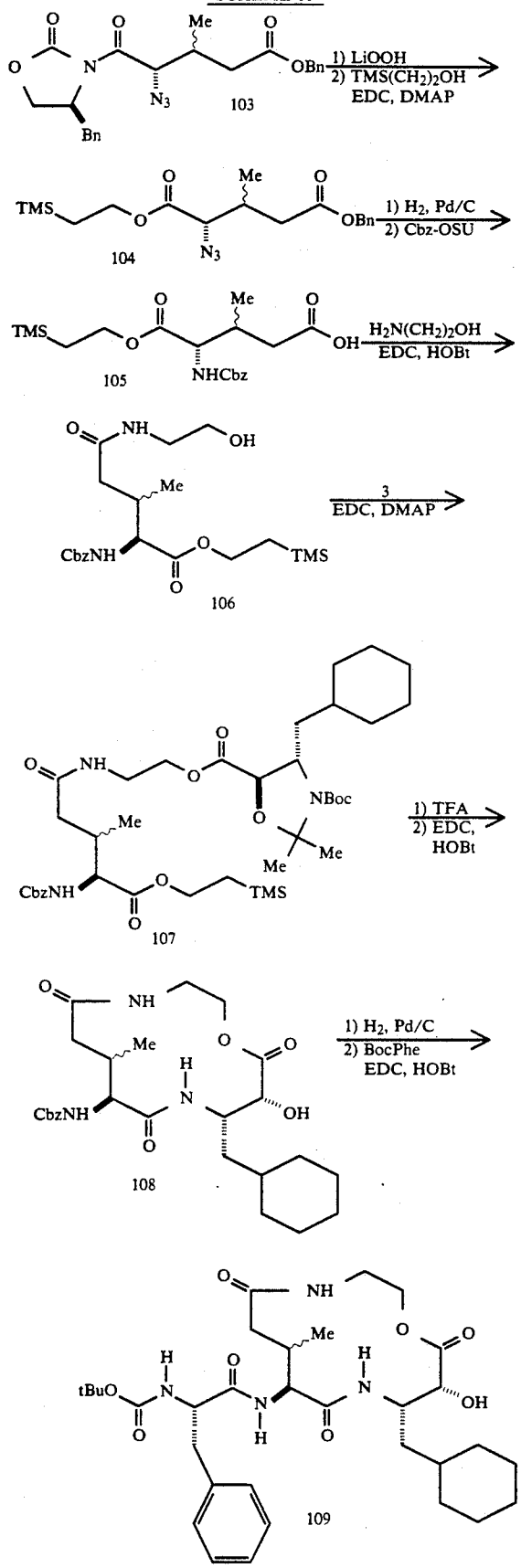

-continued
SCHEME 11

Acid Chloride 101. A mixture of 5.06 g (39.5 mmol) of glutaric anhydride 100 and 4.27 g (4.08 mL, 39.5 mmol, 1.0 equiv) of benzyl alcohol was heated at 60° C. for 1 h. Five mL of toluene was added and heating continued for 1 h. To the cooled solution was added 5.51 g (3.79 mmol, 1.1 equiv) of oxalyl chloride. After the resultant orange solution was stirred overnight, it was concentrated and used without purification. The NMR was consistent with the desired product.

Imide 102. To a solution of 6.36 g (35.9 mmol) of (4S)-4-phenylmethyl-2-oxazolidinone in 60 mL of THF at −78° C. was added 22.4 mL (1.6M in hexane, 35.9 mmol, 1.0 equiv) of n-butyllithium. To the resultant slurry was added acid chloride 101 (39.5 mmol, 1.1 equiv). The cooling bath was removed and the clear solution was stirred at room temperature for 15 min, and then quenched by the addition of aqueous saturated ammonium chloride solution. Volatiles were removed in vacuo and the aqueous residue was extracted with two portions of dichloromethane. The combined organic phases were washed with aqueous saturated sodium bicarbonate solution, dried over anhydrous sodium sulfate, and concentrated. Purification by MPLC (Lobar C silica gel column, 25% ethyl acetate/hexane) gave 13.6 g (96%) of the title compound as a mixture of methyl epimers: $R_f$ 0.22 (20% ethyl acetate/hexane); MS(FAB) 396 (M+1), 380, 288, 268.

Azide 103. To a solution of 3.21 g (8.13 mmol) of imide 102 in 60 mL of THF at −78° C. was added 16.3 mL (0.5M in THF, 8.13 mmol, 1.0 equiv) of potassium bis(trimethylsilyl)amide. After the solution was stirred for 30 min. a solution of 3.02 g (9.75 mmol, 1.2 equiv) of trisyl azide in 15 mL of THF was added via cannula over 4 min. The reaction mixture was stirred for 2 min and then quenched by the addition of 2.14 mL (37.4 mmol, 4.6 equiv) of acetic acid. After the mixture was stirred for 2 h in a warm water bath (30° C.), volatiles were removed in vacuo. The residue was partitioned between ethyl acetate and saturated aqueous sodium chloride solution. The organic phase was washed with saturated aqueous sodium bicarbonate, dried over anhydrous magnesium sulfate, and concentrated. Purification by MPLC (Lobar C column, 25% ethyl acetate/hexane) gave 1.98 g (56%) of the title compound as a 1:1 mixture of diastereomers: MS(FAB) 437 (M+1), 411, 396.

Ester 104. To a solution of 1.98 g (4.54 mmol) of imide 103 in 90 mL of 3:1 THF/water at 0° C. was added 1.82 mL (18.2 mmol, 4.0 equiv) of 30% aqueous hydrogen peroxide followed by 381 mg (9.08 mmol, 2.0 equiv) of lithium hydroxide monohydrate. After 15 min, TLC analysis indicated complete reaction so the reaction was quenched by the addition of 2.52 g (20.0 mmol, 4.4 equiv) of sodium sulfite in 30 mL of water and 30 mL of saturated aqueous sodium bicarbonate solution. Volatiles were removed in vacuo and the aqueous residue was washed with three portions of dichloromethane to remove the oxazolidinone. The aqueous phase was acidified with 1N aqueous hydrochloric acid and extracted with three portions of dichloromethane. These organic phases were dried over anhydrous magnesium sulfate and concentrated to give 1.07 g of a clear oil. This material was dissolved in 30 mL of dichloromethane and treated with 682 mg (0.83 mL, 5.77 mmol, 1.5 equiv) of trimethylsilylethanol according to the general procedure for EDC/DMAP esterification. Purification by flash chromatography (silica gel, 5% ethyl acetate/hexane) provided 1.18 g (69% overall yield) of the title compound as an oil. The NMR was consistent with the desired compound as a 1:1 mixture of diastereomers.

Acid 105. A suspension of 1.18 g (3.12 mmol) of ester 104 and 200 mg of 10% Pd/C in 16 mL of 3:1 methanol/acetic acid was treated with 40 psi hydrogen for 5 h. the catalyst was removed by filtration through celite and the filtrate was concentrated, dissolved in 5 mL of THF and treated with 931 mg (3.74 mmol, 1.2 equiv) of O-Cbz hydroxysuccinimide. The mixture was stirred overnight at room temperature and concentrated. Purification by flash chromatography (30×150 mm silica gel, 5% methanol/dichloromethane) gave 1.14 g (92%) of the title compound. The NMR was consistent with the desired compound as a 1:1 mixture of diastereomers.

Alcohol 106. A solution of 1.14 g (2.88 mmol) of acid 105 and 527 mg (0.52 mL, 8.63 mmol, 3.0 equiv) of aminoethanol in 15 mL of dichloromethane was treated with 660 mg (4.31 mmol, 1.5 equiv) of HOBt and 827 mg (4.31 mmol) of EDC. The reaction mixture was stirred overnight at room temperature. The resultant cloudy reaction mixture was then diluted with 250 mL of ethyl acetate, washed sequentially with 100-mL portions of water, 1N aqueous sodium bisulfate, saturated aqueous sodium bicarbonate and saturated aqueous sodium chloride, dried over anhydrous magnesium sulfate and concentrated. Purification by flash chromatography (30×150 mm silica gel, 75% ethyl acetate/hexane) provided 805 mg (64%) of the title compound. The NMR was consistent with the desired product as a 1:1 mixture of diastereomers.

Cyclization Precursor 107. Boc-NorACHPA acetonide (3, 689 mg, 2.02 mmol, 1.1 equiv) was coupled with 805 mg (1.84 mmol, 1.0 equiv) of alcohol 106 using 527 mg (2.75 mmol, 1.5 equiv) of EDC and 22 mg (0.183 mmol, 0.1 equiv) of DMAP in 10 mL of dichloromethane for 1 h according to the general procedure for EDC/DMAP esterification. Purification by flash chromatography (40×150 mm silica gel, 15% ethyl acetate/chloroform) followed by MPLC (2 Lobar B columns in series, 15% ethyl acetate/chloroform) provided 725 mg (52%) of a faster eluting compound, diastereomer one, and 505 mg (36%) of a slower eluting compound, diastereomer two. The NMR's were consistent with the desired products. For diastereomer 1: MS(FAB) 784 (M+Na), 762 (M+1), 662. Anal. calcd. for $C_{39}H_{63}N_3O_{10}Si$: C, 61.47; H, 8.33; N, 5.51. Found: C, 61.33; H, 8.42; N, 5.29. For diastereomer 2: MS(FAB) 762 (M+1), 662. Anal. calcd. for $C_{39}H_{63}N_3O_{10}Si$: C, 61.47; H, 8.33; N, 5.51. C, 61.68; H, 8.57; N, 5.14.

Macrocycle 108. The following procedure for macrocyclization and subsequent deprotection and coupling to BocPhe is illustrated for diastereomer 2. Macrocyclization of 280 mg (0.367 mmol) of compound 107 was carried out according to the general procedure (Method A) described above. Purification by flash chromatography (20×150 mm silica gel, 2.5, 5, 7.5% methanol/dichloromethane) gave 115 mg (62%) of the title compound. The NMR was consistent with the desired product. MS(FAB) 504 (M+1). Anal. calcd. for $C_{26}H_{37}N_3O_7$ 3/4$H_2O$: C, 60.39; H, 7.59; N, 8.13. Found: C, 60.16; H, 7.44; N, 8.12.

Macrocycle 109. A solution of 43.3 mg (0.0702 mmol) of macrocycle 108 in methanol was deprotected and then treated with 55.9 mg (0.211 mmol, 3.0 equiv) of BocPhe, 32.3 mg (0.211 mmol, 3.0 equiv) of HOBt, and 40.4 mg (0.211 mmol, 3.0 equiv) of EDC according to the general procedure (Method A). Purification by flash chromatography (20×150 mm silica gel; 2.5 and 5% methanol/dichloromethane) gave 30.7 mg (71%) of the title compound. The NMR was consistent with the desired product. MS(FAB) 617 (M+1), 561, 517. Anal. calcd. for $C_{32}H_{48}N_4O_8$ $H_2O$: C, 60.55; H, 7.94; N, 8.83. Found: C, 60.29; H, 8.03; N, 8.61.

SECTION J: PREPARATION OF MACROCYCLIC RENIN INHIBITORS OF THE FORMULA I, where D=—CONH—, W=—NH—, Z=—OH, Y=—OCO—, and A—B=N-carboxyalkyl derivative Scheme 12 illustrates the preparation of macrocyclic renin inhibitors of the formula I, where D=—CONH—, W=—NH—, Z=—OH, Y=—OCO—, and A—B=N-carboxyalkyl derivative. As shown in Scheme 12, the Cbz group of macrocycle 85 is removed and the resultant amine is reductively alkylated with a 2-ketoester to give compounds such as ester 110. Hydrogenolysis of the benzyl ester followed by coupling with amines using standard coupling conditions yields amides such as macrocycle 111.

SCHEME 12

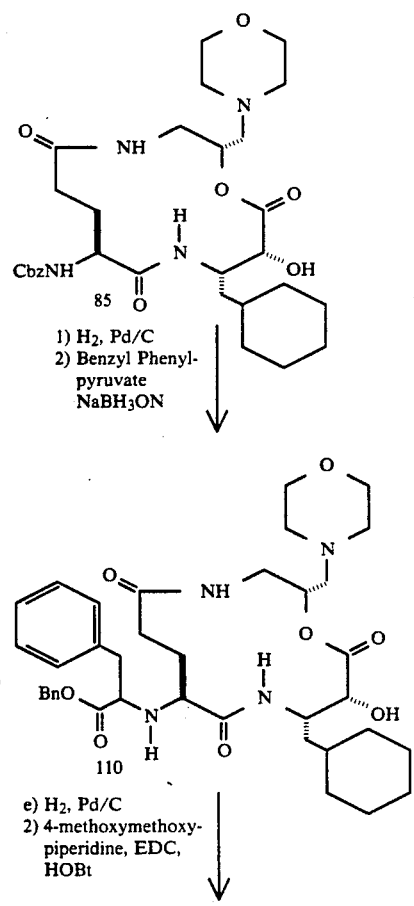

-continued
SCHEME 12

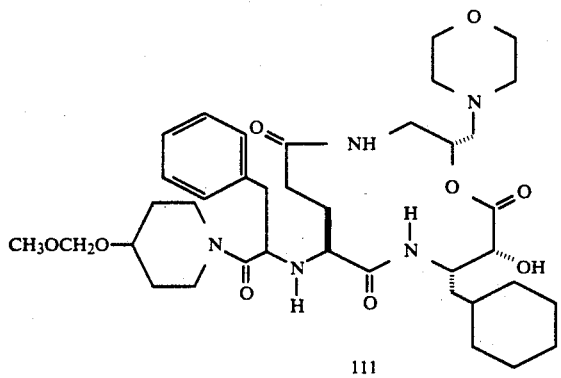

111

SECTION K: PREPARATION OF MACROCYCLIC RENIN INHIBITORS OF THE FORMULA I, where D=—CONH—, W=—NH, Z=—OH, Y=—OCO and A—B=a carboxyalkoxy derivative.

Scheme 13 illustrates the preparation of macrocyclic renin inhibitors of the formula I, where D=—CONH—, W=—NH—, Z=—OH, Y=—OCO— and A—B=a carboxyalkoxy derivative. As shown in Scheme 13, acid 114 (prepared as shown from D-glutamic acid derivative 112) is coupled to aminoalcohol 82 to provide alcohol 115. Coupling of 115 to norACHPA Boc acetonide 3 gives macrocycle precursor 116. This compound is treated with acid and the resultant amino acid is cyclized to provide macrocycle 117. Removal of the benzyl blocking group followed by coupling to amines using standard conditions gives macrocycles such as 118.

SCHEME 13

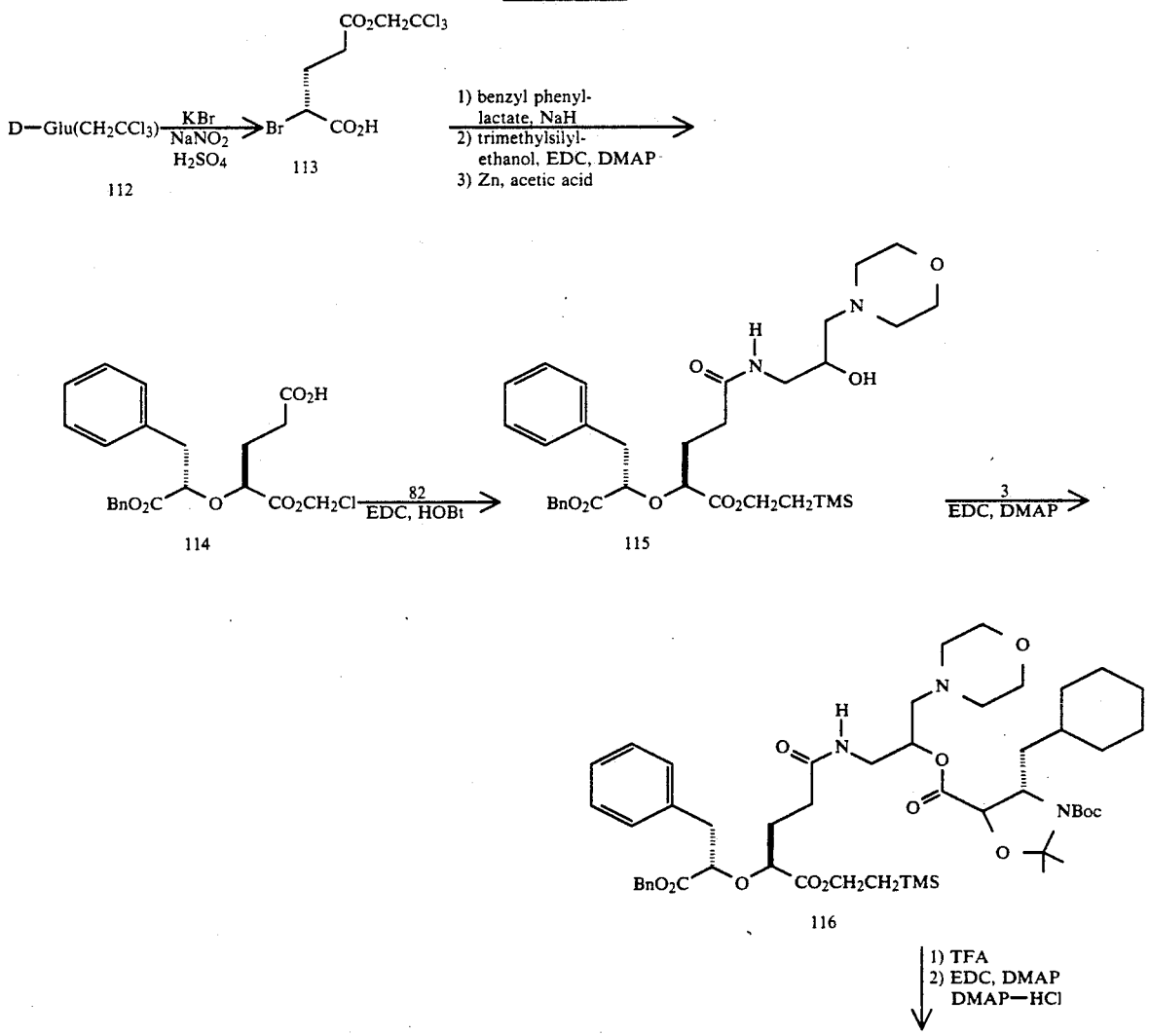

-continued
SCHEME 13

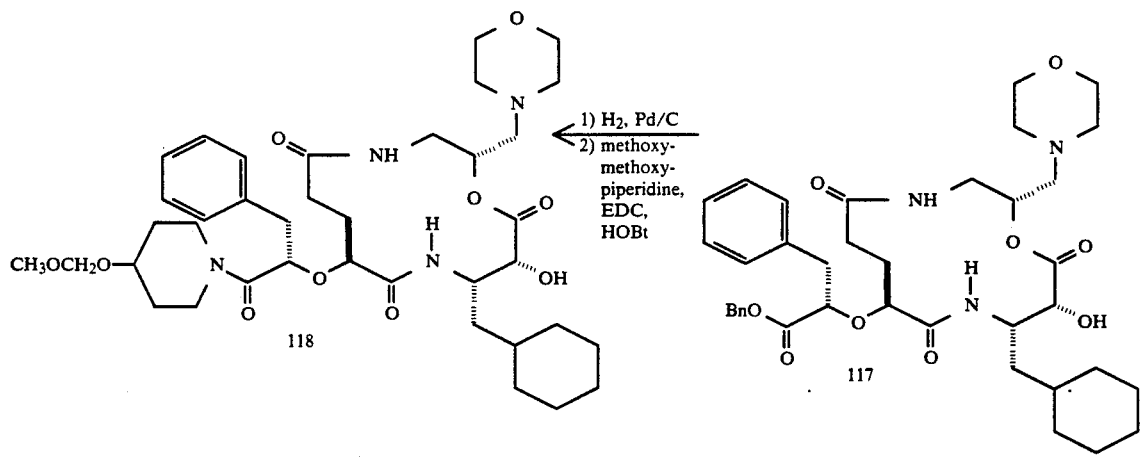

SECTION L: PREPARATION OF MACROCYCLIC RENIN INHIBITORS OF THE FORMULA I, where D=—S—, or —SO, or —SO₂, W=—NH—, Z=—OH, and Y=—OCO Scheme 14 illustrates the preparation of macrocyclic renin inhibitors of the formula I, where D=—S—, or —SO, or —SO₂, W=—NH—, Z=—OH, Y=—OCO. As shown in Scheme 14, Boc-norACHPA acetonide is alkylated with a diiodide to provide iodo-ester 119.

Coupling of 119 with L-cysteine followed by protection of the amino acid with Cbz gives the macrocycle precursor 121. This compound is treated with acid and the resultant amino acid is cyclized to provide macrocycle 122. Removal of the benzyl blocking group followed by coupling with a carboxylic acid or acid chloride or sulfonyl chloride using standard conditions gives macrocycles such as 123. Oxidation of the sulfide to sulfoxide (with sodium periodate) or sulfone (with oxone) yields compound such as 124 and 125.

SCHEME 14

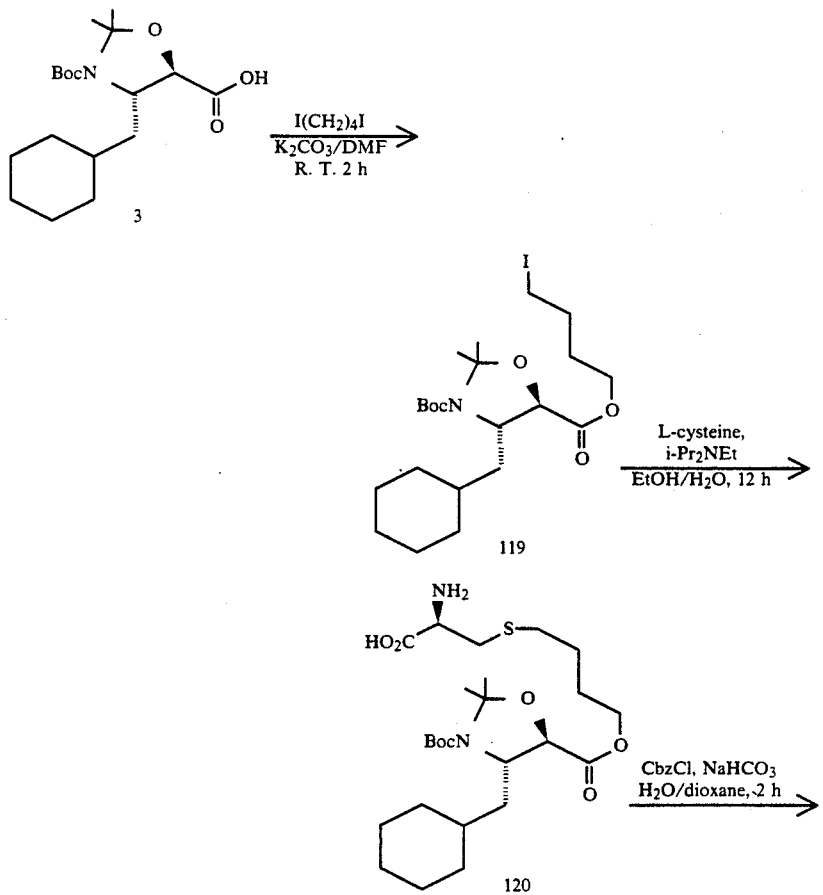

-continued
SCHEME 14

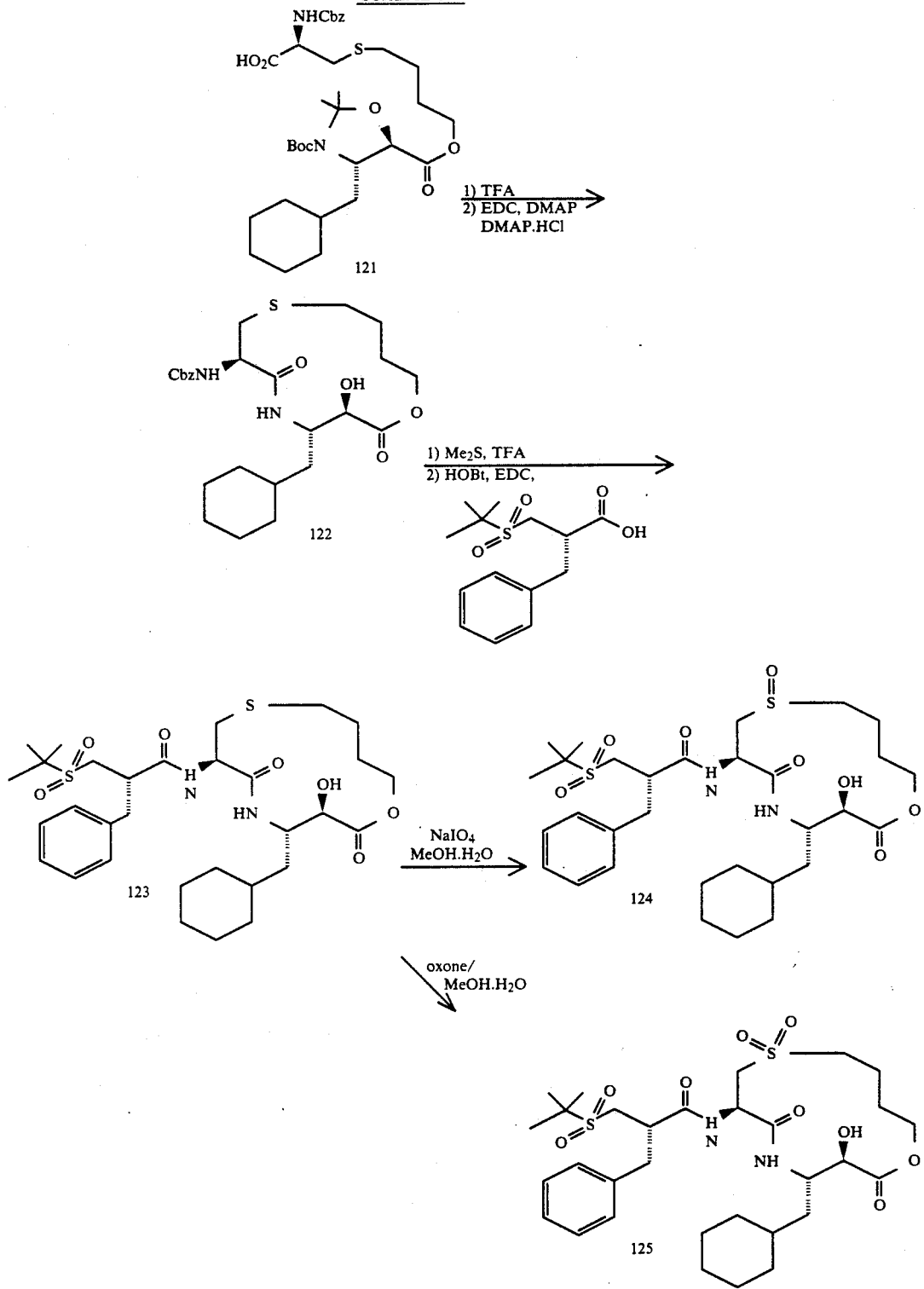

Iodo-ester 119

A suspension of Boc-norACHPA acetonide (3, 1.95 g, 5.7 mmol), 1,4-diiodobutane (6 ml, 8 equiv), potassium carbonate (1.6 g, 2 equiv) in 20 ml of DMF was stirred at room temperature for 3 hours. The reaction mixture was poured to cold water and extracted twice with ethyl acetate and hexanes mixture (1:1). The combined extracts were washed with brine, dried over sodium sulfate, and evaporated. Purification by silica flash chromatography eluting with a solvent gradient of 0–10% ethyl acetate in hexanes gave 2.81 g (94%) of the title compound as a colorless oil which solidified upon standing: Rf=0.37 (10% ethyl acetate in hexanes); MS (FAB) 524 (M+1) 424.

Carboxylic acid 121

To a solution of 119 (1.35 g, 2.58 mmol), L-cysteine (376 mg, 1.2 equiv) in water and ethanol (1:1, 20 ml) under Ar was added diisopropyl ethyl amine (1.8 ml, 4 equiv). The reaction mixture was stirred at room temperature for 1 day and was evaporated to remove solvents to give crude amino acid 120 (3.88 g) which was used without further purification. To a solution of the crude 120 (1.94 g) and sodium bicarbonate (1.08 g, 10 equiv) in 1,4-dioxane and water (1:1, 100 ml) was added benzyl chloroformate (0.19 ml, 1 equiv) dropwise. The reaction was completed in 2 hours. The solution was saturated with sodium chloride and was extracted with ethyl acetate (3 times). The combined extracts were dried over sodium sulfate and evaporated. Silica gel flash column chromatography employing a solvent gradient of 0–10% methanol in dichloromethane afforded 617 mg (73%) of the title compound: MS (FAB) 689 (M+K), 651 (M+1), 551, 481.

Macrocycle 122

Compound 121 (617 mg, 0.95 mmol) was treated with TFA (5 ml) for 1 hour. The mixture was concentrated and trace amounts of acid were removed by azeotropically with THF and toluene. The resulting oil was purified by silica gel flash chromatography eluting with a solvent gradient of 5–20% methanol in dichloromethane to give 714 mg of the deprotected compound. The deprotected compound (416 mg) was cyclized according to general procedure method C. Flash chromatography eluting with 40% ethyl acetate in hexanes afforded the title compound (97 mg, 34% total): Rf=0.56 (60% ethyl acetate in hexanes). MS (FAB) 493 (M+1).

Macrocycle 123

Following the procedure described in general procedure method E, compound 122 was deprotected and acylated with 2-benzyl-3-(tert-butylsulfonyl) propionic acid to afford the title compound in 61% yield: Rf=0.37 (60% ethyl acetate in hexanes); MS (FAB) 625 (M+1).

Sulfone 125

To a solution of 123 (4.0 mg, 0.0064 mmol) in methanol (2 ml) was added a solution of oxone (30 mg, 7 equiv) in water (2 ml) at 0° C. The reaction mixture was stirred at room temperature for 3 hours and partitioned between brine and ethyl acetate. The organic layer was separated, dried, and evaporated. Silica gel column purification eluting with a solvent gradient of 50–90% ethyl acetate in hexanes give 4.0 mg (95%) of the title compound: Rf=0.67 (ethyl acetate), MS (FAB) 657 (M+1).

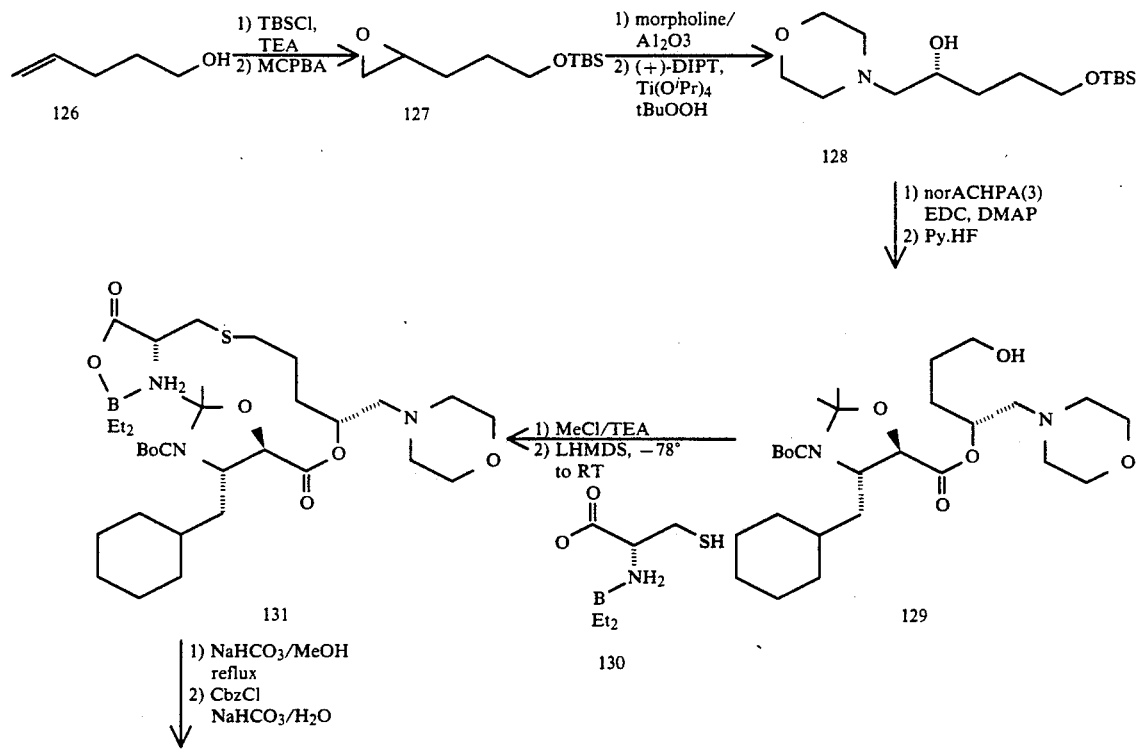

SCHEME 15

-continued
SCHEME 15
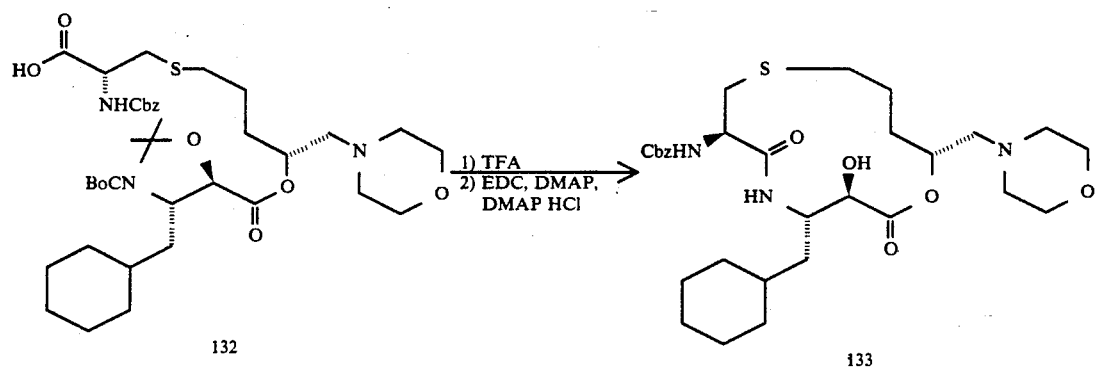
132
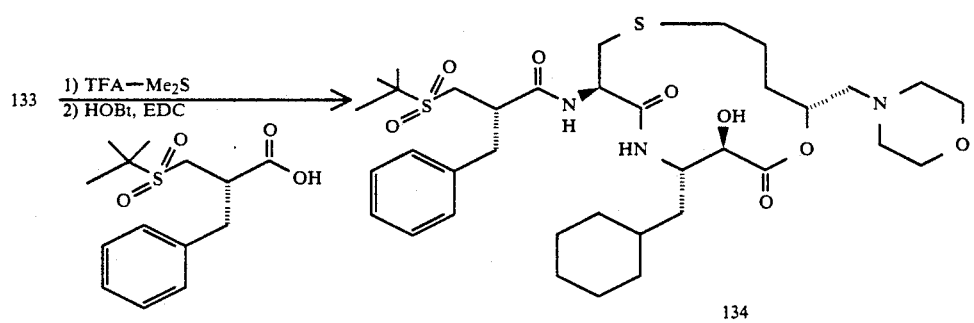
134
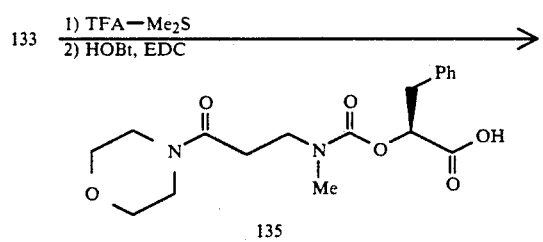
135
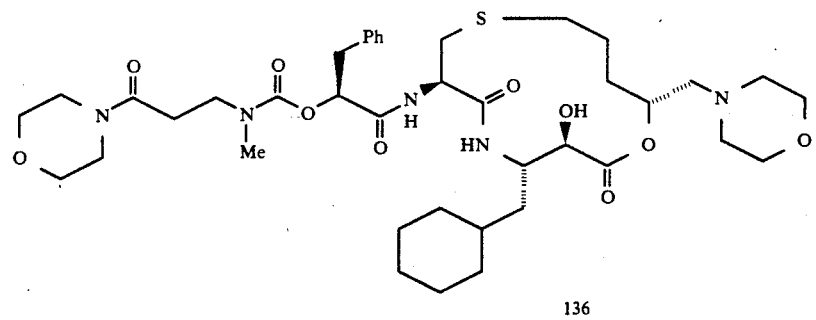
136
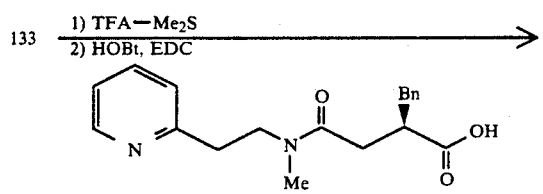
137

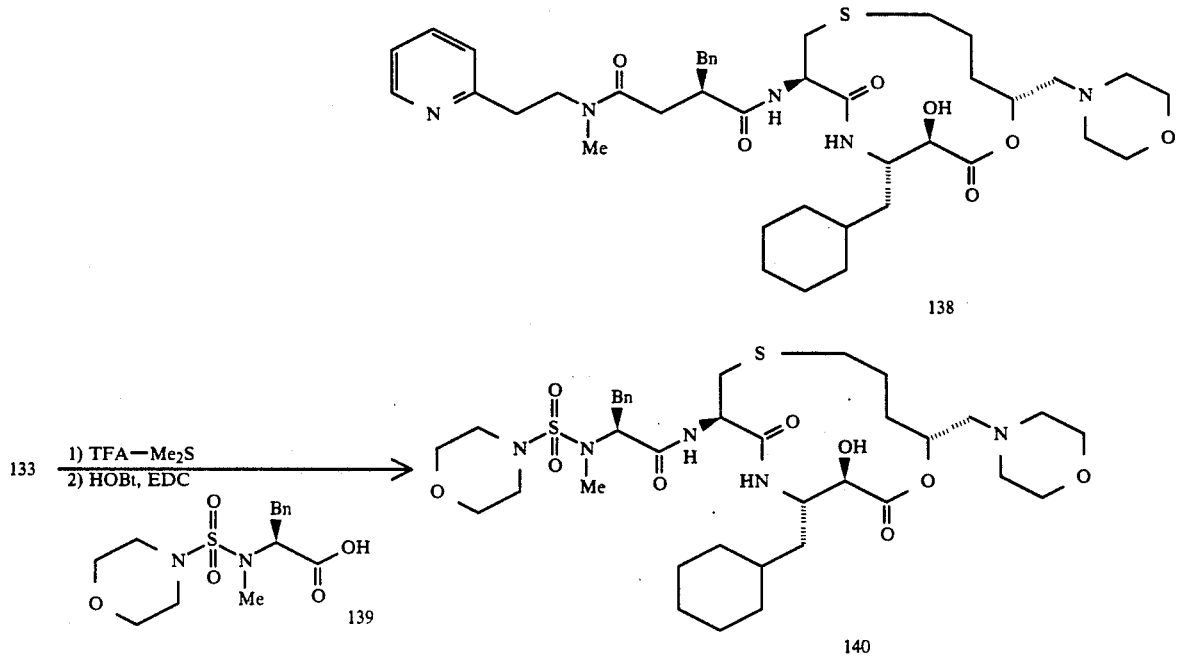

SECTION M: PREPARATION OF MACROCYCLIC RENIN INHIBITORS OF THE FORMULA I, where D=—S—, or —SO, or —SO₂, W=—NH—, Z=—OH, and Y=—OCO Scheme 15 illustrates the preparation of macrocyclic renin inhibitors of the formula I, where D=—S—, or —SO, or —SO₂, W=—NH—, Z=—OH, Y=—OCO. As shown in Scheme 15, Boc-norACHPA acetonide is coupled with the alcohol 128 to afford an ester which was treated with pyridinium hydrofloride to give alcohol 129. The alcohol was converted to its mesylate and then reacted with L-cysteine diethylborane (130) anion to provide compound 131. Deprotection of the borane complex and followed by reprotection of the resultant amino acid with Cbz gives the macrocycle precursor 132. This compound is treated with acid and the resultant amino acid is cyclized to provide macrocycle 133. Removal of the benzyl blocking group gave the TFA amine salt, which was coupled with a carboxylic acid or acid chloride or sulfonyl chloride using standard conditions gives macrocycles such as 134, 136, 138, 140. The sulfide can be oxidized to sulfoxide (with sodium periodate) or sulfone (with oxone).

Epoxide 127

A solution of 4-pentene-1-ol (25 g, 0.29 mol), TBDMSCl (0.32 mol), triethylamine (61 ml, 0.44 ml), and DMAP (100 mg) in dichloromethane (200 ml) was stirred at room temperature for 2 hours. The reaction mixture was evaporated to remove most dichloromethane and partitioned between ethyl acetate and water. The organic layer was dried over magnesium sulfate and evaporated to afford a light yellow oil which was used without further purification.

To a vigorously stirred suspension of the silyl ether and sodium bicarbonate (10 g) in dichloromethane (600 ml) was added MCPBA (55%, 109 g, 0.35 mol) in 5 portions in 20 min. The mixture was stirred at room temperature for five hours and then filtered. The filtrate was concentrated and purified by silica gel chromatography eluting with 10% ethyl acetate in hexanes to afford 45 g (70%) of the epoxide 127.

Amino alcohol 128

A suspension of epoxide 127 (45 g, 0.21 mol), morpholine (25 ml, 0.29 mol) and neutral alumina (50 g) in ether (200 ml) was stirred at room temperature for five days. The reaction mixture was filtered to remove alumina and the filtrate was concentrated. Silica gel flash chromatography eluting with acetone/hexane (1:4) afforded 55 g (87%) of the racemic alcohol 128.

In a flame dried flask was placed the racemic amino alcohol 128 (12.12 g, 40 mmol) and (+)-diisopropyl L-tartrate (11.34 g, 48.4 mmol), and charged with 400 ml of dichloromethane under Argon. Titanium (IV) isopropoxide (25 ml, 0.84 mmol) was added and the mixture was stirred at room temperature for 30 min. The mixture was cooled at −20° and to which t-butyl hydroperoxide (3M in 2,2,4-trimethylpentane 8 ml, 0.24 mmol) was added dropwise over 30 min and the mixture was stirred at −20° for additional 2 hours. Water (16 ml) was added to quich the reaciton, and the saturated sodium potassium tartrate in water (20 ml), and ether (400 ml) was added stirred overnight to break the titanium coplex. The resulting emulsion was filtered through celite and the organic phase was separated, the aquous phase was extracted with ethyl acetate (twice). the extracts were combined and dried over magnesium sulfate. Silica gel flash chromatography eluting with acetone/hexane (4:1) afforded 4.2 g (35%) of the enatiomeric enriched (R)- alcohol 128.

Alcohol 129

To a solution of Boc-norACHPA acetonide (3, 8.0 g, 25.5 mmol), the alcohol 128 (9.0 g, 29.7 mmol), and DMAP (143 mg) in dichloromethane (100 ml) was add EDC in four portions. The mixture was stirred at room temperature for 3 hours and was evaporated to a small volume and partitioned between dilute sodium chloride solution and ethyl acetate. The organic layer was washed with brine, dried over sodium sulfate, and evaporated. Purification by silica flash chromatography eluting with a solvent gradient of 0–15% ethyl acetate in hexanes gave 9.2 g (63%) of the desired compound as a colorless oil. The oil was dissolved in acetonitrile (50 ml) and to which 3 pipets of hydrogen fluoride pyridine was added. The mixture was stirred overnight and evaporated. The concentrate was poured to saturated sodium bicarbonate solution and extracted with ethyl acetate. The extract was washed with sodium chloride and dried over magnesium sulfate. Silica gel flash chromatography eluting with ethyl acetate afforded 7.08 g (59%, two steps) of the title compound 129.

Borane complex 131

To a solution of alcohol 129 (7.08 g, 13.8 mmol), triethylamine (3.9 ml, 27.6 mol) in dichloromethane (100 ml), was added mesyl chloride (1.3 ml, 16.6 mmol) slowly at 0°. The reaction mixture was stirred for 15 minutes and then poured into saturated sodium bicarbonate and extracted with ether. The ether extract was dried and passed through a short silica gel column quickly and washed with ethyl acetate. Evaporation gave the mesylate as a yellow oil which was pumped under high vacuum for 20 minutes and used without further purification. To a solution of cysteine diethylborane complex (4.0 g, 21 mmol) in THF (60 ml) was added LHMDS (1M in toluene, 18 ml, 18 mmol) slowly at −78° followed by the addition of the mesylate in THF (40 ml). The reaction mixture was slowly warmed to room temperature and stirred overnight. The reaction mixture was poured into saturated sodium bicarbonate solution and extracted with ethyl acetate. The extract was washed with brine and dried over magnesium sulfate and evaporated. Silica gel flash column chromatography employing a solvent gradient of 40–100% ethyl acetate in hexanes afford 6 g (64%) of the title compound.

Carboxylic acid 132:

The suspension of the borane complex 131 (2.9 g, 4.2 mmol) and sodium bicarbonate (1.6 g) in 100 ml of methanol was refluxed for 20 minutes. The solvent methanol was removed in vacuo and the residue was dissolved in 60 ml of mixed solvent of water-THF-dioxane (1:1:1). With stirring, benzyl chloroformate (0.72 ml, 5 mmol) was added dropwise. The reaction was completed in 20 minutes. The solution was saturated with sodium chloride and was extracted with ethyl acetate (3 times). The combined extracts were dried over sodium sulfate and evaporated. Silica gel flash column chromatography employing a solvent gradient of 0–10% methanol in ethyl acetate afforded 2.2 g (69%) of the title compound.

Macrocycle 133:

Compound 132 (1.05, 1.4 mmol) was treated with TFA (10 ml) for 1 hour. The mixture was concentrated and trace amounts of acid were removed by azeotropically with THF and toluene (5 times). The deprotected compound (416 mg) was cyclized according to general procedure method C. Flash chromatography eluting with 5% methanol in ethyl acetate afforded the title compound (321 mg 38% total).

Macrocycle 134:

Following the procedure described in general procedure method E, compound 133 was deprotected and acylated with 2-benzyl-3-(tert-butylsulfonyl) propionic acid to afford the title compound in 61% yield.

Acylation with acid 135 afforded macrocycle 136 in 50% yield

Acylation with acid 137 afforded macrocycle 138 in 72% yield

Acylation with acid 139 afforded macrocycle 140.

What is claimed is:

1. A compound of the formula:

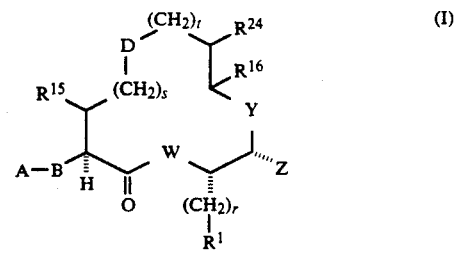

wherein:

A is hydrogen,

Het, where Het is a saturated or unsaturated 5 to 7-membered monocyclic or 7 to 10-membered bicyclic ring which contains at least one and up to two nitrogen atoms (optionally quaternized or in the N-oxide form), where Het may optionally be benzofused, where Het may optionally contain one additonal ring atom chosen from among the list consisting of O or S, in sulfide, sulfoxide or sulfone form, where Het may optionally be substituted with one or two Het substituents independently selected from the group consisting of —OH, $C_1$-$C_4$-alkyl, —$CF_3$, —CN, $C_1$-$C_4$-alkoxy, $C_1$-$C_4$-alkoxy-$C_1$-$C_4$-alkoxy, halo, —$NH_2$, mono-or di-($C_1$-$C_4$-alkyl)amino, —$CO_2H$, —$CO_2$—$C_1$-$C_4$-alkyl, —$CONR^{2a}R^{2b}$, —$SO_3H$, $C_1$-$C_4$-alkyl-CO—, aryl (where aryl is unsubstituted or mono-di-, or trisubstituted phenyl or naphthyl wherein the substitutent(s) is/are independently selected from the group consisting of $C_1$-$C_8$-alkyl, amino, phenyl-$C_1$-$C_4$-alkyl, mono- or di-$C_1$-$C_4$-alkyl amino, amino-$C_1$-$C_4$-alkyl, mono- or di-$C_1$-$C_4$-alkylamino-$C_1$-$C_4$-alkyl, guanidyl, guanidyl-$C_1$-$C_4$-alkyl, —OH, $C_1$-$C_4$-alkoxy, —$CONR^{2a}R^{2b}$, —$CO_2H$, —$CO_2$—$C_1$-$C_4$-alkyl, —$CF_3$, halo, $C_1$-$C_4$-alkyl-CO—, $C_1$-$C_4$-alkyl-CONH—, tri-($C_1$-$C_4$-alkyl)N$^+$ X$^-$, where X$^-$ is a counterion selected from the group consisting of single negatively charged ions, such as chloride, bromide, nitrate, perchlorate, benzoate, maleate, benzenesulfonate, methanesulfonate, tartrate, hemitartrate, and acetate) and mono- or disubstituted $C_1$-$C_4$-alkyl (where the substitutent(s) is/are independently selected from the group consisting of —$CO_2H$, —$CO_2$—$C_1$-$C_5$-alkyl, $C_1$-$C_5$-alkyl-CONH—, —OH, —$SO_3H$, $C_1$-$C_4$-alkyl-$SO_2$—, $C_1$-$C_4$-alkyl-SO—, —$SO_2NHCO$—$C_1$-$C_4$-alkyl, $C_1$-$C_5$-alkyl-OCONH— and aryl as defined above), where if one or both N are quaternized in Het, then each nitrogen atom may be quaternized with a Het substituent cited above selected from the group consisting of —$C_1$-$C_4$-alkyl, —$CF_3$, aryl and mono- or disubstituted $C_1$-$C_4$-alkyl with the corresponding counterion being X$^-$ as defined above, where Het may have in the alternative to the above Het substituents, a Het substituent selected from the group consisting of —$(CH_2)_q$— and —$(CH_2)_2O(CH_2)_2$— which forms a quaternary spirocyclic ring with the N atom wherein q is 3-to-6 and the counterion is $X^-$ as defined above, where Het may be substituted both with one Het substituent chosen from among those listed above and also with up to four Het substituents selected from the group consisting of $C_1$-$C_2$-alkyl substituents and Het-$C_1$-$C_4$-alkyl (where Het is as defined above without optional substitution and where the alkyl group is optionally substituted with one or two substituents independently selected from the group consisting of hydroxyl, —$CO_2H$, —$CO_2$—$C_1$-$C_4$-alkyl, —$SO_3H$, and aryl where aryl is as defined above), aryl, where aryl is defined above, $R^2CO$—, where $R^2$ is unsubstituted or mono- or disubstituted $C_1$-$C_4$-alkyl where the substituent(s) is/are selected from the group consisting of $C_1$-$C_4$-alkyl, —$SO_3H$, aryl or aryl-CO— (where aryl is as defined above), Het or Het-CO— (where Het is as defined above), $R^{2a}O$—, $R^{2a}OCO$—, $R^{2a}R^{2b}N$—, $R^{2a}R^{2b}NCO$—, $R^{2a}R^{2b}NCONH$—, $R^{2a}R^{2b}NSO_2$, $(R^{2a}O)(R^{2b}O)PO$—, $R^{2c}S$—, $R^{2c}SO$—, $R^{2c}SO_2$—, $R^{2c}CONH$—, $R^{2c}OCONH$—, and —$N(R^{17}R^{18}R^{19})+X^-$ (where $R^{2a}$ and $R^{2b}$ are independently hydrogen, $C_1$-$C_4$-alkyl, aryl as defined above, Het as defined above, $R^{2c}$ is $C_1$-$C_4$-alkyl, aryl as defined above or Het as defined above, $R^{19}$ is $C_1$-$C_4$-alkyl, $R^{17}$ and $R^{18}$ are independently aryl as defined above, Het as defined above or $C_1$-$C_4$-alkyl optionally substituted with a substituent chosen from the group consisting of aryl as defined above, Het as defined above, —OH, —$NH_2$, —NH—$C_1$-$C_4$-alkyl, —N($C_1$-$C_4$-alkyl)$_2$, —$CO_2H$, —$CO_2$—$C_1$-$C_4$-alkyl, —$SO_3H$, —CO—NH—$SO_2$—$C_1$-$C_4$-alkyl, or —CO—NH—$SO_2$-aryl, and $X^-$ is as defined above), $R^2$— (where $R^2$ is as defined above), $R^2OCO$— (where $R^2$ is as defined above), $R^2SO_2$— (where $R^2$ is as defined above), Aryl-CO— (where aryl is as defined above), Het-CO— (where Het is as defined above), $R^{2a}R^{2b}N$—CO— (where $R^{2a}$ and $R^{2b}$ are as defined above),

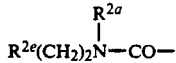

where $R^{2a}$ is as defined above and $R^{2e}$ is het-CO where Het is as defined above or Het $SO_2$—, $R^{2a}R^{2b}N$—$SO_2$— (where $R^{2a}$ and $R^{2b}$ are as defined above) and $C_1$-$C_4$-alkyl-$(OCH_2CH_2)_xOCO$— (where x is 1 to 3);

B is $CH_2$—$CH[(CH_2)_rR^3]CON(R^{11})$—N-$(A^1)CH[(CH_2)_rR^3]CO$—$N(R^{11})$—,

—O—$CH[(CH_2)_rR^3]CO$—$N(R^{11})$—, —N-$(A^1)CH[(CH_2)_rR^3]$—CO—O—,

—O—$CH[(CH_2)_rR^3]CO$—O— or —N-$(A^1)CH[(CH_2)_rR^3]CH(OH)CH_2$—, where r is 0-to-2, $A^1$ is hydrogen or $C_1$-$C_4$-alkyl, $R^3$ is hydrogen, $C_1$-$C_4$-alkyl, $C_3$-$C_7$-cycloalkyl, aryl as defined above, Het as defined above or 4-(morpholin-4-yl)ethoxy phenyl-, and $R^{11}$ is hydrogen or $C_1$-$C_4$-alkyl, A and B together may alternatively be:

G—$CH_2CH[(CH_2)_rR^3]$—Q—$N(R^{11})$—,

G—$CH_2CH[(CH_2)_rR^3]$—CO—O—, Het-S(O)$_m$—$CH[(CH_2)_rR^3]CON(R^{11})$—, (where r, $R^3$, $R^{11}$ and Het are as defined above and Q is —CO— or —$SO_2$—), $R^{2d}CON(R^{11})$—, $R^{2d}OCON(R^{11})$— or $R^{2d}SO_2N(R^{11})$—, $R^{2d}$—CO—O—, (where $R^{2d}$ is Het as defined above, aryl as defined above, or $C_1$-$C_4$-alkyl or $C_2$-$C_4$-alkenyl substituted with Het, Het-O—, aryl, or aryl-O—, each as defined above),

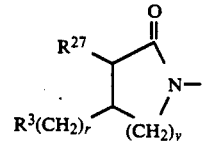

or

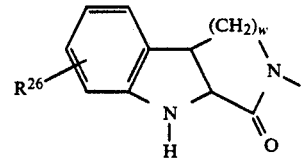

(where v is 1-to-3, w is 1 or 2, $R^3$ and r are as defined above, $R^{27}$ is hydrogen, $C_1$-$C_4$-alkyl or A—N(H)— where A is independently selected from the definitions of A as defined above and $R^{26}$ is $C_1$-$C_4$-alkyl, amino, mono- or di-$C_1$-$C_4$-alkylamino, —OH, $C_1$-$C_4$-alkoxy, —$CO_2H$, —$CO_2$—$C_1$-$C_4$-alkyl, —$CONR^{2a}R^{2b}$, —$CF_3$, halo, —NHCO—O—$C_1$-$C_4$-alkyl, —N($C_1$-$C_4$-alkyl)-CO—O—$C_1$-$C_4$-alkyl, —NHCO—$C_1$-$C_4$-alkyl or —N($C_1$-$C_4$-alkyl)CO—$C_1$-$C_4$-alkyl);

G is $R^{20}$—S(O)$_m$— (where m is 0-to-2 and $R^{20}$ is $C_3$-$C_7$-cycloalkyl, aryl as defined above, Het as defined above or $C_1$-$C_6$-alkyl optionally substituted with one or two substituents chosen from the group consisting of $C_1$-$C_4$-alkoxy, —OH, —$CO_2H$, —$CO_2$—$C_1$-$C_4$-alkyl, —$NH_2$, —NH($C_1$-$C_4$-alkyl), —N($C_1$-$C_4$-alkyl)$_2$, and ($C_1$-$C_5$-alkyl)CO—O—), $R^{17}R^{18}NSO_2$— (where $R^{17}$ and $R^{18}$ are as defined above),

where r, $R^{2a}$ and $R^{2e}$ are as defined above, or

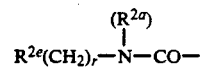

where r, $R^{2a}$ and $R^{2e}$ are as defined above;

$R^{20}CO$— (where $R^{20}$ is as defined above), $R^{20}OCO$— (where $R^{20}$ is as defined above) or —$CH(OH)CH_2$-Het (where Het is defined above);

A and B together may be —J—$CH[(CH_2)_rR^3]$—K—;

K is

—$CH_2$—,

—CH(OH)—,

—CO—,
—NH—,
—O—,
—S—,
—SO—,
—SO$_2$—,
—NO—,
—P(O)O—;

J is
R$^{28}$—CO—(CH$_2$)$_d$ (where d is 0-to-4, R$^{28}$ is —OH, —O—C$_1$-C$_6$-alkyl, —NR$^{18}$R$^{18}$, Het), R$^{29}$—SO$_2$—, where R$^{29}$ is —C$_1$-C$_4$-alkyl, aryl, Het), R$^{30}$ (where R$^{30}$ is aryl, Het), —C$_1$-C$_4$-alkyl, optionally substituted with aryl, Het, —CO$_2$H, —CO$_2$—C$_1$-C$_4$-alkyl, —SO$_2$—C$_1$-C$_4$-alkyl, —SO$_2$Ar, —SO$_2$Het), R$^{30}$—NH—CO, where R$^{30}$ is defined above;

R$^1$ is C$_1$-C$_4$-alkyl, aryl as defined above, unsubstituted, di-, or trisubstituted C$_3$-C$_7$-cycloalkyl (where the substituents is/are selected from the group consisting of C$_1$-C$_4$-alkyl, trifluoromethyl, —OH, C$_1$-C$_4$-alkoxy, or halo) or a 5- or 6-membered ring saturated heterocycle containing one or two heteratoms selected from the group consisting of N, O or S, optionally substituted with one or two substituents (where the substituents is/are selected from among the group consisting of C$_1$-C$_4$-alkyl, C$_1$-C$_4$-alkoxy, halo, —NH$_2$, or —OH);

R$^{15}$ is C$_1$-C$_4$-alkyl, aryl as defined above, imidazol-4-yl, thiazol-4-yl or thiazol-5-yl;

D is
a single bond or is
—CO—O—
—O—
—CH=CH—
—CO— or
—CH(OH)—
(where R$^{25}$ is —H or C$_1$-C$_4$-alkyl and asymmetrical groups are read clockwise into formula I from left to right);

s is 0-to-1;
t is 1-to-4;
W is N-R$^{23}$ or O (where R$^{23}$ is defined below);
R$^{16}$ is
hydrogen or
C$_1$-C$_4$-alkyl optionally substituted with a substituent chosen from among the group consisting of C$_1$-C$_4$-alkyl, C$_3$-C$_7$-cycloalkyl, aryl as defined above, Het as defined above, —OH, —SO$_3$H, —CO$_2$H, CO$_2$—C$_1$-C$_4$-alkyl, —CO—Het, —NR$^{17}$R$^{18}$, —NHR$^{18}$, —N(R$^{17}$R$^{18}$R$^{19}$)+X$^-$ (where X$^-$, R$^{17}$, R$^{18}$ and R$^{19}$ are defined above), —S(O)$_m$—R$^{21}$ (where m is as defined above and R$^{21}$ is Het, aryl or C$_1$-C$_4$-alkyl the alkyl optionally substituted with a substituent chosen from among the group consisting of aryl, Het, —NH$_2$, —OH, —NH—C$_1$-C$_4$-alkyl or N(C$_1$-C$_4$-alkyl)$_2$), —SO$_2$NH$_2$, —SO$_2$NR$^{17}$R$^{18}$ (where R$^{17}$ and R$^{18}$ are as defined above), —SO$_2$NHR$^{18}$ (where R$^{18}$ is as defined above) and —CH$_2$(OCH$_2$CH$_2$)$_x$—O—C$_1$-C$_4$-alkyl, (where x is as defined above);

Y is —OCO—, —CH$_2$CO— or —CH$_2$CH(OH)— (where Y is inserted into formula I clockwise from left to right);

Z is —NH$_2$, —OH —OPO$_3$H$_2$, —OCOR$^{22}$, —O—CO—OR$^{22}$ (where R$^{22}$ is 5-indanyl or C$_1$-C$_6$-alkyl optionally substituted with Ph, —SO$_3$H, —CO$_2$H, —PO$_3$H$_2$, —NH$_2$, —NH(C$_1$-C$_4$-alkyl), —N(C$_1$-C$_4$-alkyl)$_2$, —N(C$_1$-C$_4$-alkyl)$_3$$^+$ X$^-$ where X$^-$ is defined above), —OCHR$^{22a}$—OCOR$^{22b}$ (where R$^{22a}$ and R$^{22b}$ are C$_1$-C$_4$-alkyl), or —O—COCH$_2$O—(CH$_2$CH$_2$O)$_x$—C$_1$-C$_4$-alkyl or —O—CO—O(CH$_2$CH$_2$O)$_x$—C$_1$-C$_4$-alkyl (where x is as defined above);

R$^{23}$ is hydrogen or C$_1$-C$_4$-alkyl; and
R$^{24}$ is hydrogen or C$_1$-C$_4$-alkyl.

2. A compound according to claim 1 in which Het is selected from the group consisting of piperidine, pyrryl, pyrrolinyl, quinuclidinyl, isoquinuclidinyl, pyrrolidinyl, pyrazolyl, pyrazolinyl, pyrazolidinyl, imidazolyl, imidazolinyl, imidazolidinyl, pyridyl, piperidinyl, pyrazinyl, piperazinyl, pyrimidinyl, pyridazinyl, oxazolyl, oxazolidinyl, isoxazolyl, isoxazolidinyl, morpholinyl, thiazolyl, thiazolidinyl isothiazolyl, isothiazolidinyl, indolyl, quinolinyl, isoquinolinyl, benzimidazolyl, benzothiazolyl, benzoxazolyl, furyl, thienyl or benzothienyl.

3. A compound according to claim 1 where A is selected from the group consisting of:

EtOC—, i-PrSO$_2$—, CH$_3$(OCH$_2$CH$_2$)$_3$OCO—,

-continued
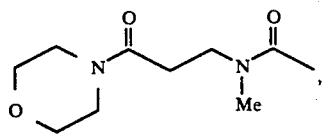
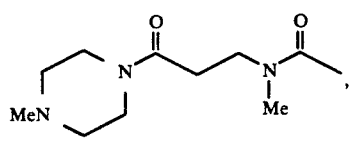
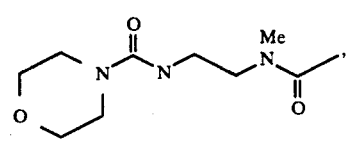
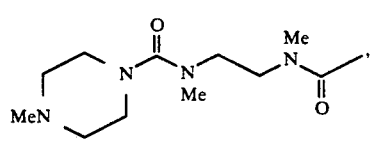
or
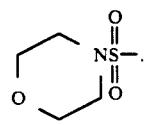
4. A compound according to claim 1 where B is selected from the group consisting of:
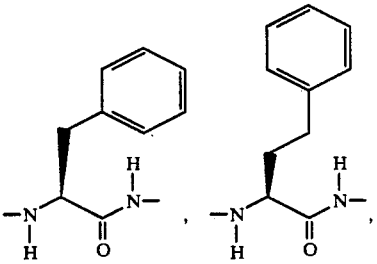
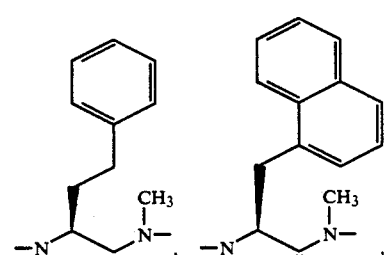
-continued
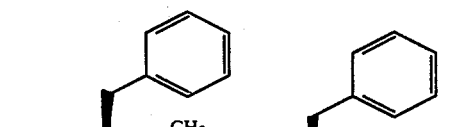
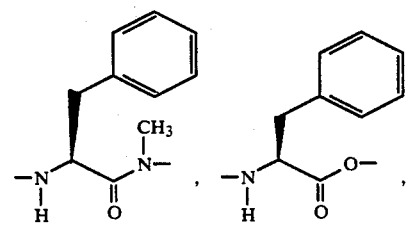
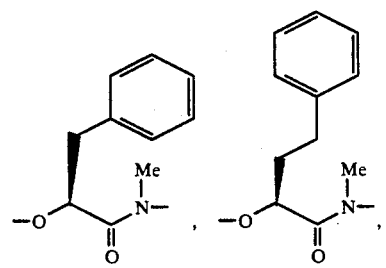
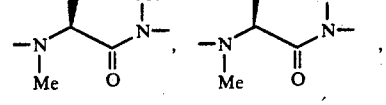
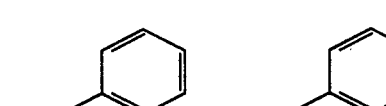
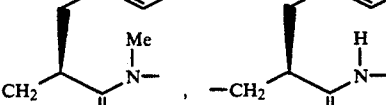
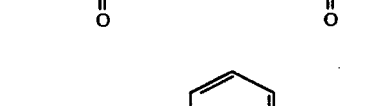
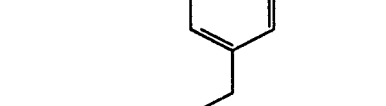
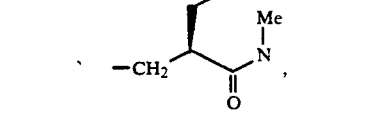
or 5. A compound according to claim 1 where A and B together are selected from the group consisting of:

131
-continued

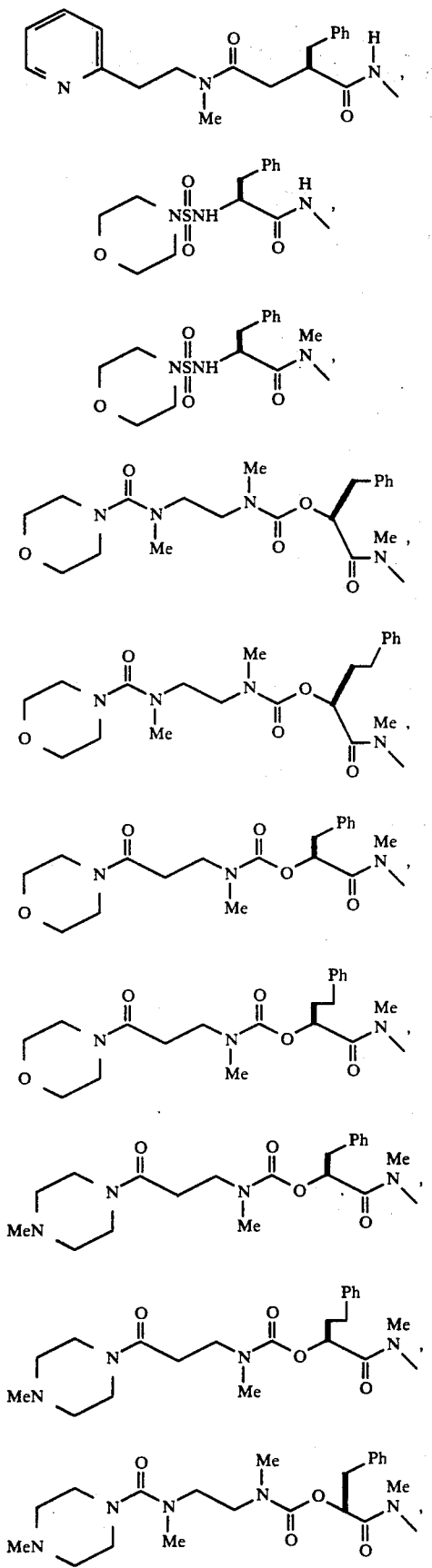

132
-continued

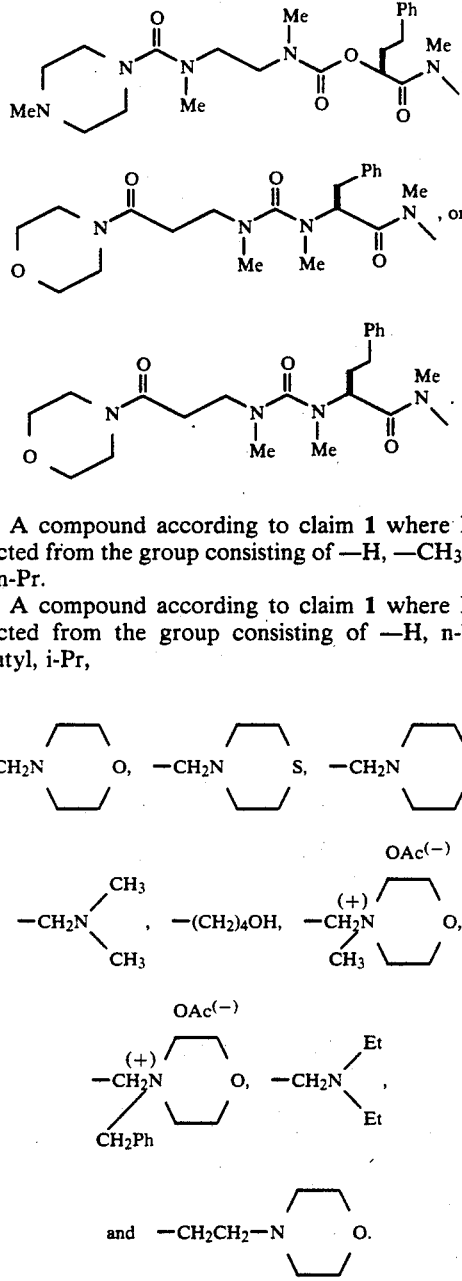

6. A compound according to claim 1 where $R^{15}$ is selected from the group consisting of —H, —CH$_3$, -i-Pr or -n-Pr.

7. A compound according to claim 1 where $R^{16}$ is selected from the group consisting of —H, n-butyl, -i-butyl, i-Pr,

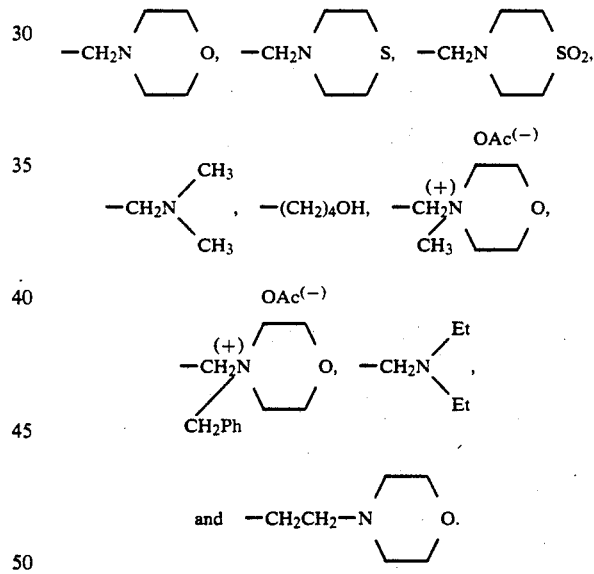

8. A compound according to claim 1 where $R^{23}$ is selected from the group consisting of —H or —CH$_3$.

9. A compound according to claim 1 where $R^{24}$ is selected from the group consisting of —H, —CH$_3$ or —Et.

10. A compound according to claim 1 where $R^{25}$ is selected from the group consisting of —H or —CH$_3$.

11. A compound according to claim 1 where r is 1.

12. A compound according to claim 1 where Z is selected from the group consisting of —OH, —OCO(CH$_2$)$_2$CO$_2$H, —OCOCH$_2$N(C$_1$-C$_4$-alkyl)$_2$, —OCOCH$_2$NH$_2$, —OCOCH$_2$CH$_2$NH$_2$, —OCO(C$_1$-C$_4$-alkyl), —NH$_2$, —OCOCH(n-Bn)—NH$_2$, —OCOCH(i-Pr)NH$_2$, —OPO$_3$H$_2$, —OCOCH$_2$CH$_2$PO$_3$H$_2$ or —O-CO—O(CH$_2$CH$_2$O)$_3$CH$_3$.

13. A compound according to claim 1 where formula I is selected from the group consisting of:

14. A compound of the formula:

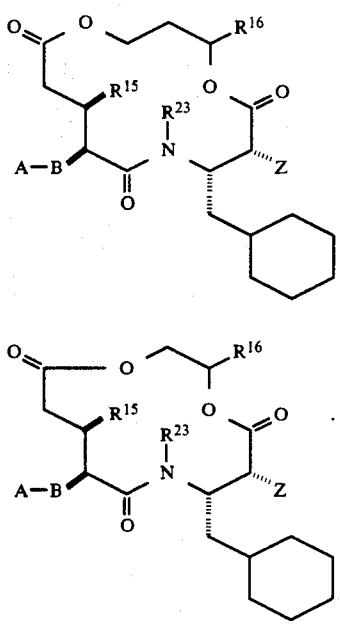

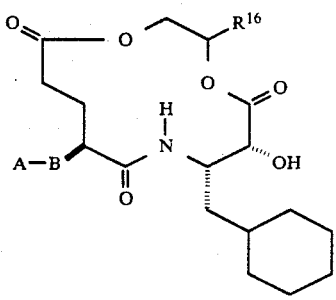

where A-B and R¹⁶ are selected from the group consisting of:

| A—B | R¹⁶(configuration) |
|---|---|
| BocPhe—NH— | H |
| tBuCH₂CONH(CH₂)₂COPhe—NH— | H |
| BocPhe—NH— | —CH₂—N○O(1) |
| BocPhe—NH— | —CH₂—N○O(2) |
| BocPhe—NH— | -n-Bu(1) |
| BocPhe—BH— | -n-Bu(2) |
| 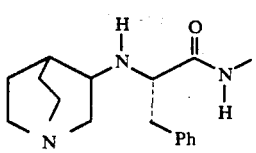 | —H |
| (quinuclidinyl-NH-CH(CH₂Ph)-C(O)NH-) | —CH₂—N○O(1) |
| (quinuclidinyl-NH-CH(CH₂Ph)-C(O)NH-) | —CH₂—N○O(2) |
| (N⁺-(CH₂)₄OH Cl⁻ quinuclidinium-NH-CH(CH₂Ph)-C(O)NH-) | -i-Bu(1) |
| (N⁺-(CH₂)₄OH Cl⁻ quinuclidinium-NH-CH(CH₂Ph)-C(O)NH-) | -i-Bu(2) |
| (tBu-SO₂-CH₂-CH(CH₂Ph)-C(O)NH-) | -i-Bu(1) |
| (tBu-SO₂-CH₂-CH(CH₂Ph)-C(O)NH-) | -i-Bu(2) |
| CH₃OCH₂O-piperidinyl-N-C(O)-CH(OCH₂Ph)- with OMe | —CH₂—N○O(1) |
| CH₃OCH₂O-piperidinyl-N-C(O)-CH(OCH₂Ph)- with OMe | —CH₂—N○O(2) |
| CH₃OCH₂O-piperidinyl-N-C(O)-CH(NHCH₂Ph)- | —CH₂—N○O(1) |
| CH₃OCH₂O-piperidinyl-N-C(O)-CH(NHCH₂Ph)- | —CH₂—N○O(2) |

15. A compound according to claim 1, wherein D is —CH=CH—, —CHOH—, —CO—, —O— or —CO—O—; and W is N.

* * * * *